US009463045B2

(12) United States Patent
Cresina et al.

(10) Patent No.: US 9,463,045 B2
(45) Date of Patent: Oct. 11, 2016

(54) POLYAXIAL PIVOT HOUSING FOR EXTERNAL FIXATION SYSTEM

(71) Applicant: Biomet Manufacturing, LLC, Warsaw, IN (US)

(72) Inventors: Jeffery T. Cresina, Warsaw, IN (US); Paul Slagle, Fort Wayne, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/212,596

(22) Filed: Mar. 14, 2014

(65) Prior Publication Data

US 2014/0276816 A1 Sep. 18, 2014

Related U.S. Application Data

(60) Provisional application No. 61/789,429, filed on Mar. 15, 2013, provisional application No. 61/788,414, filed on Mar. 15, 2013.

(51) Int. Cl.
| | |
|---|---|
| *A61B 17/00* | (2006.01) |
| *A61F 4/00* | (2006.01) |
| *A61F 5/05* | (2006.01) |
| *A61B 17/62* | (2006.01) |

(Continued)

(52) U.S. Cl.
CPC ............ *A61B 17/62* (2013.01); *A61B 17/645* (2013.01); *A61B 17/6416* (2013.01); *A61B 17/6458* (2013.01); *A61B 17/66* (2013.01); *A61B 2017/0042* (2013.01)

(58) Field of Classification Search
CPC .. A61B 17/62; A61B 17/66; A61B 17/6466; A61B 17/6416; A61B 17/645; A61B 17/6458; A61B 17/60; A61B 17/6425

USPC ...................................... 606/53–60
See application file for complete search history.

(56) References Cited

U.S. PATENT DOCUMENTS 259,957 A * 6/1882 White .............................. 403/90
2,238,870 A * 4/1941 Haynes ........................... 606/59

(Continued)

FOREIGN PATENT DOCUMENTS

| CA | 1193506 A1 | 9/1985 |
| DE | 102007005479 A1 | 7/2008 |

(Continued)

OTHER PUBLICATIONS

International Search Report and Written Opinion from PCT/IB2014/001009 dated Feb. 20, 2015, 14 pages.

(Continued)

*Primary Examiner* — Eduardo C Robert
*Assistant Examiner* — Michelle C Eckman
(74) *Attorney, Agent, or Firm* — Schwegman Lundberg & Woessner, P.A.

(57) ABSTRACT

A polyaxial pivot housing for an external fixation system, comprising a first plate; a second plate substantially parallel to the first plate; a spherical member positioned between the first and second plates, the spherical member having a threaded post that is configured to attach to a support member of an external fixation frame; and a pivotably rotatable locking arm, the locking arm being configured to orientationally lock the threaded post with respect to the external fixation frame by compressing the first and second plates against the spherical member.

19 Claims, 47 Drawing Sheets

(51) Int. Cl.
  *A61B 17/64* (2006.01)
  *A61B 17/66* (2006.01)

(56) References Cited

U.S. PATENT DOCUMENTS

| | | | | |
|---|---|---|---|---|
| 2,652,221 A * | 9/1953 | Kampa | | 248/276.1 |
| 3,154,331 A | 10/1964 | Engelhardt et al. | | |
| 3,405,587 A * | 10/1968 | Meazzi et al. | | 84/421 |
| 4,135,505 A * | 1/1979 | Day | | 606/59 |
| 4,265,561 A | 5/1981 | Heckele | | |
| 4,273,116 A * | 6/1981 | Chiquet | | 606/54 |
| 4,299,212 A * | 11/1981 | Goudfrooy | | 606/54 |
| 4,312,336 A * | 1/1982 | Danieletto et al. | | 606/57 |
| 4,331,150 A | 5/1982 | Braun et al. | | |
| 4,349,018 A | 9/1982 | Chambers | | |
| 4,453,446 A * | 6/1984 | Hoshino | | 84/421 |
| 4,483,334 A | 11/1984 | Murray | | |
| 4,502,473 A * | 3/1985 | Harris et al. | | 606/58 |
| 4,541,422 A * | 9/1985 | de Zbikowski | | 606/59 |
| 4,602,497 A * | 7/1986 | Wallis | | 72/462 |
| 4,608,970 A | 9/1986 | Marck et al. | | |
| 4,621,627 A * | 11/1986 | DeBastiani et al. | | 606/57 |
| 4,693,240 A * | 9/1987 | Evans | | 606/54 |
| 4,714,076 A * | 12/1987 | Comte et al. | | 606/57 |
| 4,796,508 A * | 1/1989 | Hoshino | | 84/421 |
| 4,827,918 A * | 5/1989 | Olerud | | 606/258 |
| 4,838,891 A | 6/1989 | Branemark et al. | | |
| 4,911,721 A | 3/1990 | Andergaten et al. | | |
| 4,919,119 A | 4/1990 | Jonsson et al. | | |
| 4,978,350 A | 12/1990 | Wagenknecht | | |
| 4,988,349 A * | 1/1991 | Pennig | | 606/58 |
| 5,002,542 A * | 3/1991 | Frigg | | 606/264 |
| 5,007,909 A | 4/1991 | Rogozinski | | |
| 5,087,258 A * | 2/1992 | Schewior | | 606/56 |
| 5,160,335 A | 11/1992 | Wagenknecht | | |
| 5,207,676 A | 5/1993 | Canadell et al. | | |
| 5,261,590 A | 11/1993 | Tsai | | |
| 5,314,425 A * | 5/1994 | Shpigel | | 606/53 |
| 5,320,622 A * | 6/1994 | Faccioli et al. | | 606/58 |
| 5,323,664 A * | 6/1994 | Fairfield et al. | | 74/551.3 |
| 5,385,536 A | 1/1995 | Burkhead et al. | | |
| 5,443,464 A * | 8/1995 | Russell et al. | | 606/54 |
| 5,451,226 A * | 9/1995 | Pfeil et al. | | 606/59 |
| 5,454,810 A * | 10/1995 | Pohl et al. | | 606/59 |
| 5,480,442 A | 1/1996 | Bertagnoli | | |
| 5,496,319 A * | 3/1996 | Allard et al. | | 606/56 |
| 5,499,986 A | 3/1996 | Dimarco | | |
| 5,507,827 A | 4/1996 | Grundei et al. | | |
| 5,507,835 A | 4/1996 | Jore | | |
| 5,520,694 A | 5/1996 | Dance et al. | | |
| 5,527,309 A | 6/1996 | Shelton | | |
| 5,540,697 A | 7/1996 | Rehmann et al. | | |
| 5,549,612 A * | 8/1996 | Yapp et al. | | 606/293 |
| 5,562,737 A | 10/1996 | Graf | | |
| 5,584,831 A | 12/1996 | McKay | | |
| 5,653,707 A | 8/1997 | Taylor et al. | | |
| 5,683,389 A * | 11/1997 | Orsak | | 606/59 |
| 5,702,389 A * | 12/1997 | Taylor et al. | | 606/56 |
| 5,707,370 A | 1/1998 | Berki et al. | | |
| 5,725,526 A * | 3/1998 | Allard et al. | | 606/57 |
| 5,728,095 A * | 3/1998 | Taylor et al. | | 606/54 |
| 5,743,898 A * | 4/1998 | Bailey et al. | | 606/54 |
| 5,752,954 A | 5/1998 | Mata et al. | | |
| 5,769,851 A * | 6/1998 | Veith | | 606/57 |
| 5,782,572 A | 7/1998 | Thiem | | 403/90 |
| 5,788,695 A * | 8/1998 | Richardson | | 606/57 |
| 5,797,908 A * | 8/1998 | Meyers et al. | | 606/54 |
| 5,803,642 A | 9/1998 | Sassmannshausen | | 403/90 |
| 5,803,924 A * | 9/1998 | Oni et al. | | 606/54 |
| 5,827,282 A | 10/1998 | Pennig | | 606/54 |
| 5,846,245 A * | 12/1998 | McCarthy et al. | | 606/105 |
| 5,879,386 A | 3/1999 | Jore | | |
| 5,891,144 A | 4/1999 | Mata et al. | | |
| 5,897,555 A * | 4/1999 | Clyburn et al. | | 606/54 |
| 5,902,302 A | 5/1999 | Berki et al. | | |
| 5,971,984 A * | 10/1999 | Taylor et al. | | 606/54 |
| 5,984,922 A | 11/1999 | McKay | | |
| 6,007,534 A * | 12/1999 | Gonzalez et al. | | 606/54 |
| 6,030,387 A | 2/2000 | Ballier | | |
| 6,080,153 A | 6/2000 | Mata et al. | | |
| 6,168,345 B1 | 1/2001 | Legge | | |
| 6,170,598 B1 * | 1/2001 | Furukawa | | 180/334 |
| 6,176,860 B1 * | 1/2001 | Howard | | 606/54 |
| 6,217,577 B1 * | 4/2001 | Hofmann | | 606/57 |
| 6,221,072 B1 * | 4/2001 | Termaten | | 606/54 |
| 6,245,071 B1 * | 6/2001 | Pierson | | 606/58 |
| 6,277,118 B1 * | 8/2001 | Grant et al. | | 606/54 |
| 6,342,054 B1 | 1/2002 | Mata | | |
| 6,361,537 B1 * | 3/2002 | Anderson | | 606/86 B |
| 6,468,276 B1 | 10/2002 | McKay | | |
| 6,613,049 B2 | 9/2003 | Winquist et al. | | |
| 6,616,664 B2 | 9/2003 | Walulik et al. | | |
| 6,623,483 B1 * | 9/2003 | Kazakov et al. | | 606/57 |
| 6,623,485 B2 | 9/2003 | Doubler et al. | | |
| 6,709,433 B1 | 3/2004 | Schoenefeld | | |
| 6,948,878 B1 * | 9/2005 | Smith et al. | | 403/110 |
| 7,004,943 B2 | 2/2006 | Ferrante et al. | | |
| 7,048,735 B2 * | 5/2006 | Ferrante et al. | | 606/59 |
| 7,094,241 B2 | 8/2006 | Hodorek et al. | | |
| 7,241,074 B2 | 7/2007 | Thomke et al. | | |
| 7,276,069 B2 | 10/2007 | Biedermann et al. | | |
| 7,320,555 B2 * | 1/2008 | Chang et al. | | 403/122 |
| 7,384,268 B2 | 6/2008 | Browne-Wilkinson | | |
| 7,422,593 B2 | 9/2008 | Cresina et al. | | |
| 7,597,694 B2 | 10/2009 | Lim et al. | | |
| 7,601,154 B2 | 10/2009 | Kuczynski et al. | | |
| 7,608,074 B2 * | 10/2009 | Austin et al. | | 606/54 |
| 7,611,526 B2 | 11/2009 | Carl et al. | | |
| 7,658,753 B2 | 2/2010 | Carl et al. | | |
| 7,686,809 B2 | 3/2010 | Triplett et al. | | |
| 7,708,765 B2 | 5/2010 | Carl et al. | | |
| 7,730,563 B1 | 6/2010 | Sklar et al. | | |
| 7,736,307 B2 * | 6/2010 | Hu et al. | | 600/210 |
| 7,758,582 B2 | 7/2010 | Ferrante et al. | | |
| 7,758,652 B2 | 7/2010 | Engh et al. | | |
| 7,776,067 B2 | 8/2010 | Jackson | | |
| 7,799,054 B2 | 9/2010 | Kwak et al. | | |
| 7,799,057 B2 | 9/2010 | Hudgins et al. | | |
| 7,842,039 B2 | 11/2010 | Hodorek et al. | | |
| 7,842,073 B2 | 11/2010 | Richelsoph et al. | | |
| 7,887,537 B2 | 2/2011 | Ferrante et al. | | |
| 7,887,541 B2 | 2/2011 | Runco et al. | | |
| 7,914,531 B1 | 3/2011 | Geller et al. | | |
| 7,931,650 B2 | 4/2011 | Winquist et al. | | |
| 7,951,173 B2 | 5/2011 | Hammill, Sr. et al. | | |
| 7,967,850 B2 | 6/2011 | Jackson | | |
| 8,002,801 B2 | 8/2011 | Carl et al. | | |
| 8,012,181 B2 | 9/2011 | Winslow et al. | | |
| 8,016,860 B2 | 9/2011 | Carl et al. | | |
| 8,016,861 B2 | 9/2011 | Mitchell et al. | | |
| 8,043,345 B2 | 10/2011 | Carl et al. | | |
| 8,048,125 B2 | 11/2011 | Mitchell et al. | | |
| 8,057,478 B2 | 11/2011 | Kuczynski et al. | | |
| 8,070,783 B2 | 12/2011 | Kwak et al. | | |
| 8,114,158 B2 | 2/2012 | Carl et al. | | |
| 8,118,847 B2 * | 2/2012 | Wallenstein et al. | | 606/286 |
| 8,172,840 B2 | 5/2012 | Murner et al. | | |
| 8,187,274 B2 | 5/2012 | Schulze | | |
| 8,241,285 B2 | 8/2012 | Mullaney | | |
| 8,267,938 B2 * | 9/2012 | Murphy | | 606/91 |
| 8,409,259 B1 | 4/2013 | Bedor | | 606/289 |
| 8,419,777 B2 * | 4/2013 | Walker et al. | | 606/289 |
| 8,439,914 B2 | 5/2013 | Ross et al. | | |
| 8,568,456 B2 * | 10/2013 | Black | | 606/250 |
| 8,747,418 B2 * | 6/2014 | Qureshi et al. | | 606/130 |
| 8,832,910 B2 | 9/2014 | Lah | | 24/457 |
| 8,882,814 B2 * | 11/2014 | Suh | | 606/289 |
| 8,906,077 B2 * | 12/2014 | Bush et al. | | 606/296 |
| 9,087,498 B2 * | 7/2015 | Sato et al. | | |
| 2001/0051806 A1 * | 12/2001 | Ballier | | 606/54 |
| 2002/0115998 A1 * | 8/2002 | Schoenefeld | | 606/59 |
| 2002/0166935 A1 | 11/2002 | Carnevali | | |
| 2003/0004511 A1 * | 1/2003 | Ferree | | 606/61 |
| 2003/0009167 A1 | 1/2003 | Wozencroft | | |

(56) References Cited

U.S. PATENT DOCUMENTS

| | | | |
|---|---|---|---|
| 2003/0073996 A1 | 4/2003 | Doubler et al. | |
| 2003/0114853 A1 | 6/2003 | Burgess et al. | |
| 2003/0125736 A1* | 7/2003 | Venturini et al. | 606/59 |
| 2003/0139744 A1* | 7/2003 | Berki et al. | 606/57 |
| 2003/0149429 A1 | 8/2003 | Ferrante et al. | |
| 2003/0149430 A1 | 8/2003 | Ferrante et al. | |
| 2003/0153910 A1* | 8/2003 | Janowski et al. | 606/56 |
| 2003/0155180 A1* | 8/2003 | Liew et al. | 182/186.8 |
| 2004/0102785 A1 | 5/2004 | Hodorek et al. | |
| 2004/0138659 A1 | 7/2004 | Austin et al. | |
| 2005/0075633 A1* | 4/2005 | Ross | 606/61 |
| 2005/0095058 A1* | 5/2005 | Biba et al. | 403/56 |
| 2005/0119656 A1 | 6/2005 | Ferrante et al. | |
| 2005/0135874 A1* | 6/2005 | Baylis et al. | 403/76 |
| 2005/0171540 A1 | 8/2005 | Lim et al. | |
| 2005/0187551 A1* | 8/2005 | Orbay et al. | 606/69 |
| 2005/0191124 A1* | 9/2005 | Watanabe | 403/373 |
| 2005/0203511 A1 | 9/2005 | Wilson-MacDonald et al. | |
| 2005/0216020 A1 | 9/2005 | Orton | |
| 2005/0234466 A1 | 10/2005 | Stallings | |
| 2005/0240197 A1 | 10/2005 | Kmiec, Jr. | |
| 2005/0245939 A1 | 11/2005 | Ferrante et al. | |
| 2005/0261690 A1* | 11/2005 | Binder et al. | 606/69 |
| 2006/0004460 A1 | 1/2006 | Engh et al. | |
| 2006/0036246 A1 | 2/2006 | Carl et al. | |
| 2006/0036256 A1 | 2/2006 | Carl et al. | |
| 2006/0036259 A1 | 2/2006 | Carl et al. | |
| 2006/0036323 A1 | 2/2006 | Carl et al. | |
| 2006/0036324 A1 | 2/2006 | Sachs et al. | |
| 2006/0051728 A1 | 3/2006 | Browne-Wilkinson | |
| 2006/0052785 A1 | 3/2006 | Augostino et al. | |
| 2006/0053689 A1* | 3/2006 | Smith | 47/45 |
| 2006/0095043 A1 | 5/2006 | Martz et al. | |
| 2006/0149241 A1 | 7/2006 | Richelsoph et al. | |
| 2006/0158109 A1 | 7/2006 | Takahashi et al. | |
| 2006/0229604 A1* | 10/2006 | Olsen et al. | 606/54 |
| 2006/0229605 A1* | 10/2006 | Olsen | 606/54 |
| 2006/0241637 A1 | 10/2006 | Hodorek et al. | |
| 2006/0241639 A1 | 10/2006 | Kuczynski et al. | |
| 2006/0247629 A1* | 11/2006 | Maughan et al. | 606/61 |
| 2006/0259018 A1 | 11/2006 | Shilkrut | |
| 2006/0271046 A1 | 11/2006 | Kwak et al. | |
| 2006/0276789 A1 | 12/2006 | Jackson | |
| 2007/0017139 A1* | 1/2007 | Larue | 42/75.1 |
| 2007/0055236 A1 | 3/2007 | Hudgins et al. | |
| 2007/0088358 A1 | 4/2007 | Yuan et al. | |
| 2007/0100338 A1* | 5/2007 | Deffenbaugh et al. | 606/54 |
| 2007/0123856 A1* | 5/2007 | Deffenbaugh et al. | 606/54 |
| 2007/0123857 A1* | 5/2007 | Deffenbaugh et al. | 606/54 |
| 2007/0147829 A1* | 6/2007 | Teratani | 396/428 |
| 2007/0161983 A1* | 7/2007 | Cresina et al. | 606/54 |
| 2007/0161984 A1* | 7/2007 | Cresina et al. | 606/54 |
| 2007/0162142 A1 | 7/2007 | Stone | |
| 2007/0213597 A1* | 9/2007 | Wooster | 600/234 |
| 2007/0233256 A1 | 10/2007 | Ohrt et al. | |
| 2007/0255280 A1 | 11/2007 | Austin et al. | |
| 2007/0281283 A1 | 12/2007 | Lundgren | |
| 2007/0288011 A1 | 12/2007 | Logan | |
| 2008/0015585 A1 | 1/2008 | Berg et al. | |
| 2008/0077136 A1 | 3/2008 | Triplett et al. | |
| 2008/0125787 A1 | 5/2008 | Doubler et al. | |
| 2008/0161853 A1 | 7/2008 | Arnold et al. | |
| 2008/0195153 A1 | 8/2008 | Thompson | |
| 2008/0286736 A1 | 11/2008 | Browne-Wilkinson | |
| 2008/0312656 A1* | 12/2008 | Vasta | 606/60 |
| 2008/0315479 A1 | 12/2008 | Fayollas et al. | |
| 2009/0024166 A1 | 1/2009 | Carl et al. | |
| 2009/0030419 A1 | 1/2009 | Runco et al. | |
| 2009/0030420 A1 | 1/2009 | Runco et al. | |
| 2009/0062866 A1 | 3/2009 | Jackson | |
| 2009/0088751 A1 | 4/2009 | Mullaney | |
| 2009/0210062 A1* | 8/2009 | Thalgott et al. | 623/17.16 |
| 2009/0287062 A1 | 11/2009 | Farley | |
| 2009/0287212 A1 | 11/2009 | Hirata et al. | |
| 2009/0306670 A1 | 12/2009 | Kuczynski et al. | |
| 2010/0030271 A1 | 2/2010 | Winslow et al. | |
| 2010/0030273 A1 | 2/2010 | Mitchell et al. | |
| 2010/0036426 A1 | 2/2010 | Mitchell et al. | |
| 2010/0100130 A1 | 4/2010 | Carl et al. | |
| 2010/0100133 A1 | 4/2010 | Carl et al. | |
| 2010/0137920 A1 | 6/2010 | Hammill, Sr. et al. | |
| 2010/0145389 A1 | 6/2010 | Triplett et al. | |
| 2010/0178100 A1* | 7/2010 | Fricke et al. | 403/90 |
| 2010/0191288 A1 | 7/2010 | Carl et al. | |
| 2010/0191291 A1* | 7/2010 | Phan et al. | 606/301 |
| 2010/0191293 A1 | 7/2010 | Jackson | |
| 2010/0211114 A1 | 8/2010 | Jackson | |
| 2010/0234844 A1* | 9/2010 | Edelhauser et al. | 606/56 |
| 2010/0262160 A1 | 10/2010 | Boyden et al. | |
| 2010/0262195 A1 | 10/2010 | Jackson | |
| 2010/0262239 A1 | 10/2010 | Boyden et al. | |
| 2010/0280624 A1 | 11/2010 | Engh et al. | |
| 2010/0312283 A1 | 12/2010 | Kwak et al. | |
| 2011/0015749 A1 | 1/2011 | Engh et al. | |
| 2011/0034924 A1 | 2/2011 | Tan | |
| 2011/0034961 A1 | 2/2011 | Runco et al. | |
| 2011/0098706 A1 | 4/2011 | Mullaney | |
| 2011/0098707 A1 | 4/2011 | Mullaney | |
| 2011/0112533 A1 | 5/2011 | Venturini et al. | |
| 2011/0118737 A1* | 5/2011 | Vasta et al. | 606/56 |
| 2011/0178552 A1 | 7/2011 | Biscup et al. | |
| 2011/0208187 A1* | 8/2011 | Wong | 606/59 |
| 2011/0218579 A1 | 9/2011 | Jackson | |
| 2011/0245876 A1 | 10/2011 | Brumfield | |
| 2011/0290360 A1* | 12/2011 | Robinson | 138/99 |
| 2011/0307012 A1 | 12/2011 | Mir et al. | |
| 2011/0316212 A1* | 12/2011 | Jones et al. | 269/181 |
| 2011/0319939 A1* | 12/2011 | Kretzer et al. | 606/264 |
| 2012/0029517 A1 | 2/2012 | Tan | |
| 2012/0035657 A1* | 2/2012 | Kirschman | 606/246 |
| 2012/0089186 A1 | 4/2012 | Carl et al. | |
| 2012/0109197 A1 | 5/2012 | Carl et al. | |
| 2012/0141196 A1* | 6/2012 | Lin | 403/322.4 |
| 2012/0179212 A1 | 7/2012 | Jackson et al. | |
| 2012/0197297 A1 | 8/2012 | Bootwala et al. | |
| 2012/0203225 A1* | 8/2012 | Mingozzi et al. | 606/59 |
| 2012/0209264 A1 | 8/2012 | Zandona et al. | |
| 2012/0209335 A1 | 8/2012 | Termyna et al. | |
| 2012/0296335 A1 | 11/2012 | Mullaney | |
| 2012/0321373 A1* | 12/2012 | Chang | 403/106 |
| 2012/0324682 A1* | 12/2012 | Ballentine | 24/535 |
| 2013/0060291 A1* | 3/2013 | Petersheim | 606/305 |
| 2013/0085342 A1* | 4/2013 | Stefanchik et al. | 600/232 |
| 2014/0039564 A1* | 2/2014 | Hess et al. | 606/294 |
| 2014/0058389 A1 | 2/2014 | Singh et al. | |
| 2014/0066931 A1* | 3/2014 | Myers et al. | 606/59 |
| 2014/0135766 A1* | 5/2014 | Mingozzi et al. | 606/59 |
| 2014/0148860 A1* | 5/2014 | Rinner | 606/289 |
| 2014/0172022 A1* | 6/2014 | Suh | 606/291 |
| 2014/0257287 A1* | 9/2014 | Chang et al. | 606/58 |
| 2014/0257288 A1* | 9/2014 | Chang | 606/59 |
| 2014/0276815 A1* | 9/2014 | Riccione | 606/54 |
| 2014/0276819 A1 | 9/2014 | Cresina et al. | |
| 2014/0276820 A1 | 9/2014 | Cresina et al. | |
| 2014/0276822 A1* | 9/2014 | Cresina et al. | 606/57 |
| 2014/0276824 A1* | 9/2014 | Cresina et al. | 606/59 |
| 2014/0303621 A1* | 10/2014 | Gerold et al. | 606/59 |
| 2014/0350558 A1* | 11/2014 | Triplett et al. | 606/59 |
| 2014/0356049 A1* | 12/2014 | Lin et al. | 403/59 |
| 2014/0370793 A1* | 12/2014 | Barth et al. | 451/359 |
| 2015/0094774 A1* | 4/2015 | Swann et al. | 606/291 |

FOREIGN PATENT DOCUMENTS

| | | |
|---|---|---|
| EP | 0146872 A2 | 7/1985 |
| EP | 2085038 A1 | 8/2009 |
| GB | 1418017 | 12/1975 |
| WO | WO 90/11055 A1 | 10/1990 |
| WO | WO 94/21187 A1 | 9/1994 |
| WO | WO 97/03620 A1 | 2/1997 |
| WO | WO 97/16128 A1 | 5/1997 |
| WO | WO 02/054965 A1 | 7/2002 |
| WO | WO 02/094112 A1 | 11/2002 |
| WO | WO 2009/100459 A1 | 8/2009 |

(56) References Cited

FOREIGN PATENT DOCUMENTS

| WO | 2011055252 A1 | 5/2011 |
| --- | --- | --- |
| WO | WO-2014140831 A2 | 9/2014 |
| WO | WO-2014140844 A2 | 9/2014 |
| WO | WO-2014140855 A2 | 9/2014 |

OTHER PUBLICATIONS

Stryker Osteosynthesis, "Hoffmann II: External Fixation System", Brochure, 2009, 20 pages.

Stryker Trauma, "Hoffmann II: External Fixation System", Brochure, 2001, 24 pages.

International Search Report & Written Opinion from PCT/IB2014/000921 dated Oct. 14, 2014.

International Search Report & Written Opinion from PCT/IB2014/001083 dated Oct. 23, 2014.

International Search Report & Written Opinion from PCT/IB2014/000973 dated Oct. 14, 2014.

Dolphix product brochure, The Essential for Temporary External Fixation—Citieffe, Feb. 2011, 2 pages.

"U.S. Appl. No. 14/212,083, Response filed Dec. 7, 2015 to Restriction Requirement mailed Oct. 5, 2015", 5 pgs.

"U.S. Appl. No. 14/212,083, Restriction Requirement mailed Oct. 5, 2015", 7 pgs.

"U.S. Appl. No. 14/212,183, Non Final Office Action mailed Sep. 9, 2015", 8 pgs.

"U.S. Appl. No. 14/212,183, Response filed Feb. 8, 2016 to Non Final Office Action mailed Sep. 9, 2015", 11 pgs.

"U.S. Appl. No. 14/212,183, Restriction Requirement mailed Jul. 13, 2015", 6 pgs.

"U.S. Appl. No. 14/212,679, Response filed Nov. 19, 2015 to Restriction Requirement mailed Oct. 2, 2015", 7 pgs.

"U.S. Appl. No. 14/212,679, Restriction Requirement mailed Oct. 2, 2015", 8 pgs.

"U.S. Appl. No. PCT/IB2014/000973, International Preliminary Report on Patentability mailed Sep. 24, 2015", 5 pgs.

"U.S. Appl. No. PCT/IB2014/001009, International Preliminary Report on Patentability mailed Sep. 24, 2015", 10 pgs.

"U.S. Appl. No. PCT/IB2014/001083, International Preliminary Report on Patentability mailed Sep. 24, 2015", 8 pgs.

"International Application Serial No. PCT/IB2014/000921, International Preliminary Report on Patentability mailed Sep. 24, 2015", 9 pgs.

\* cited by examiner

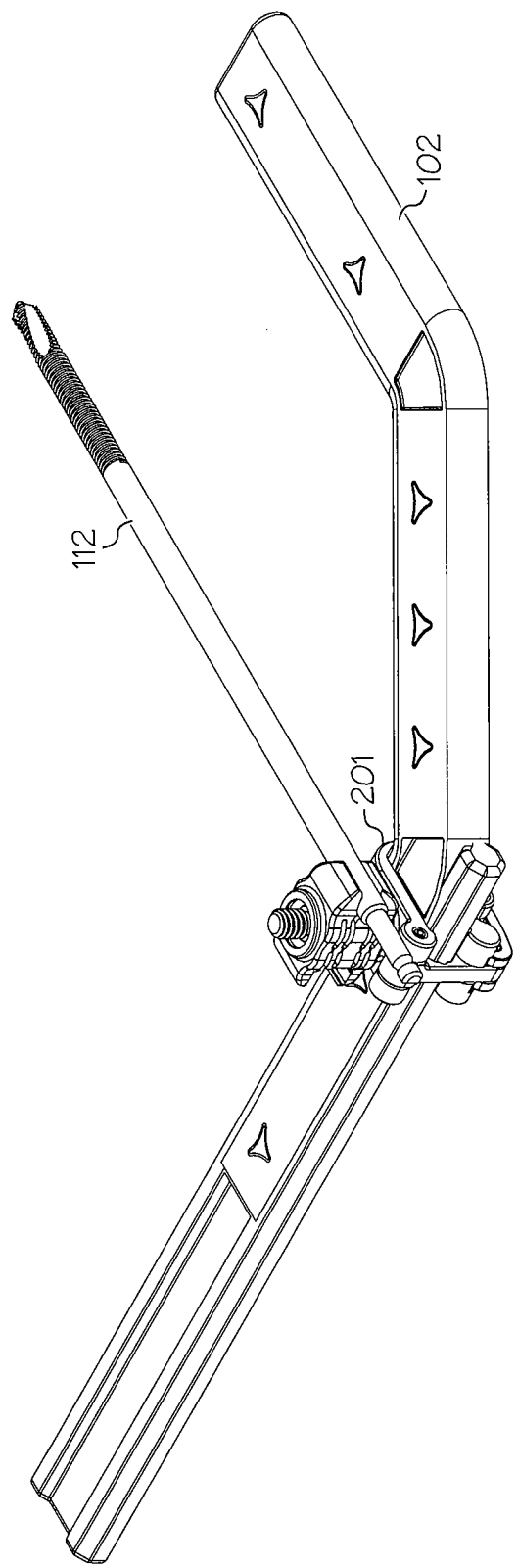

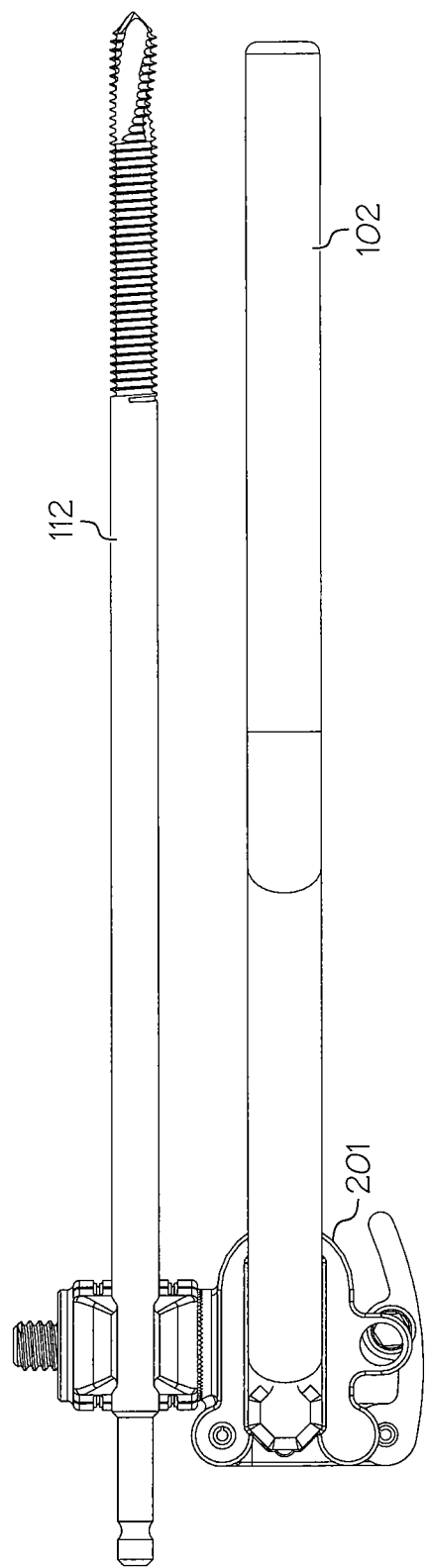

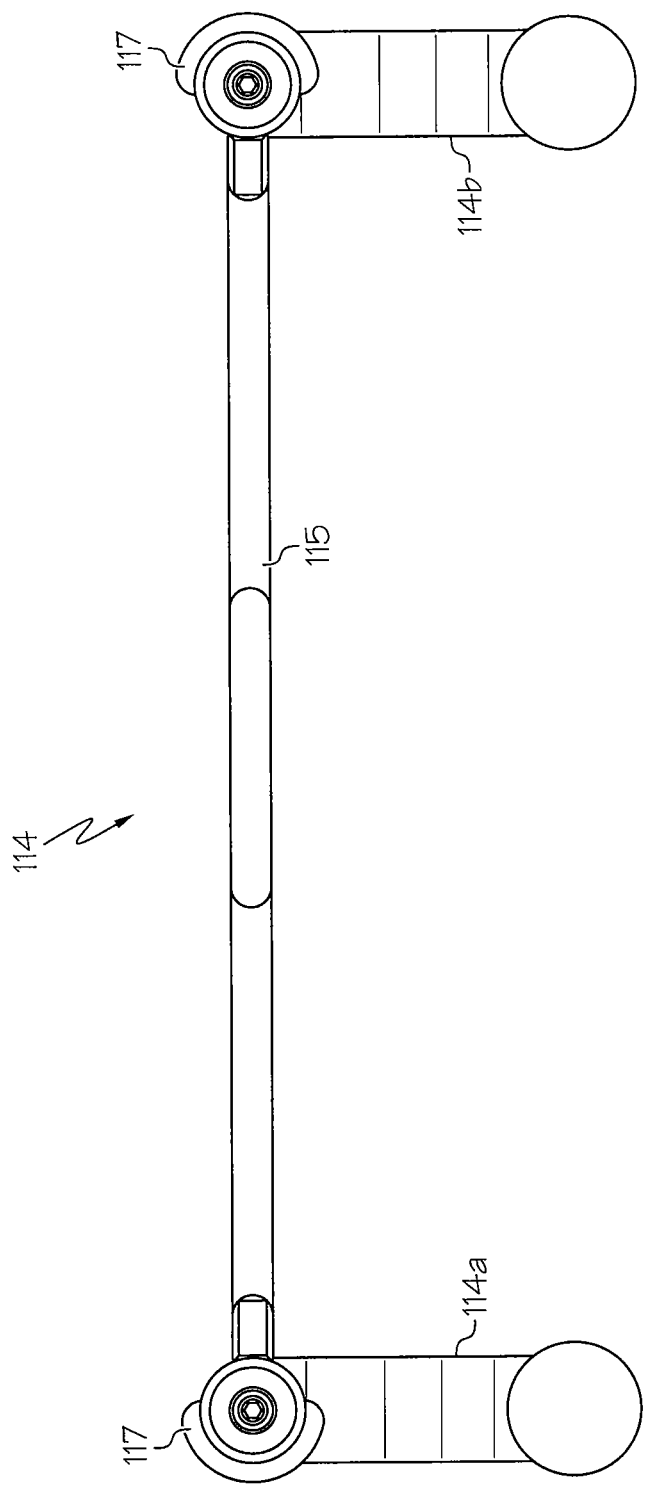

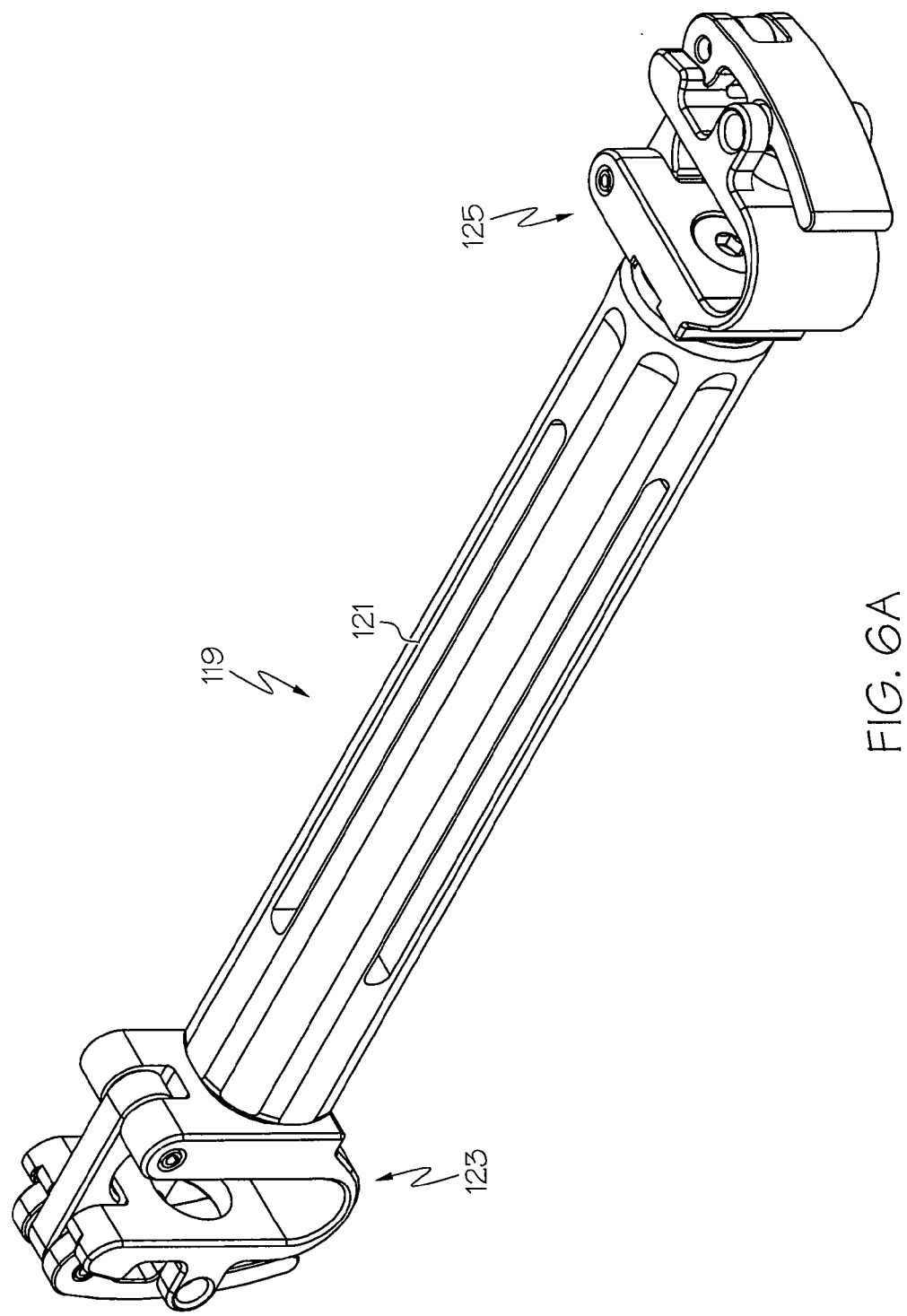

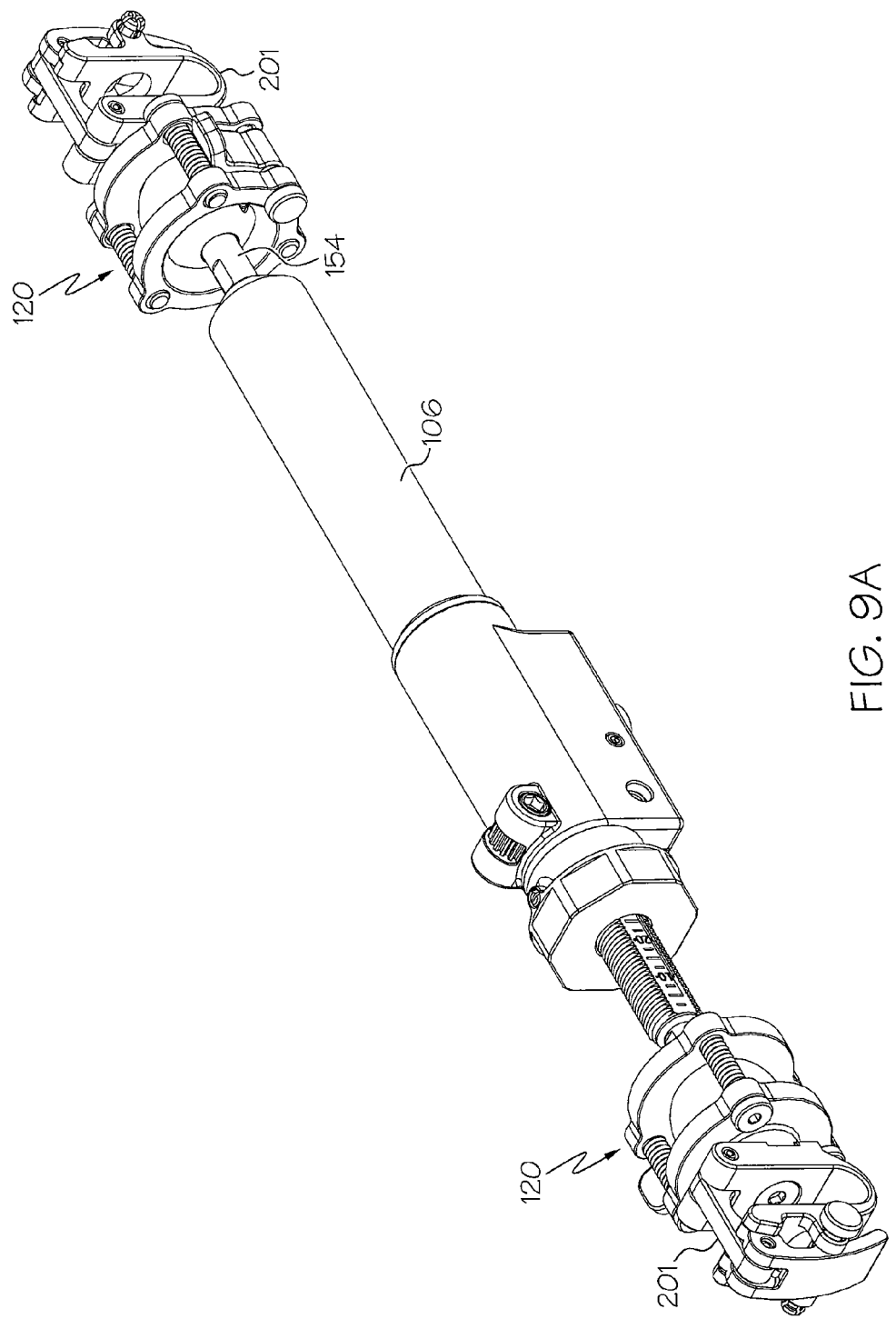

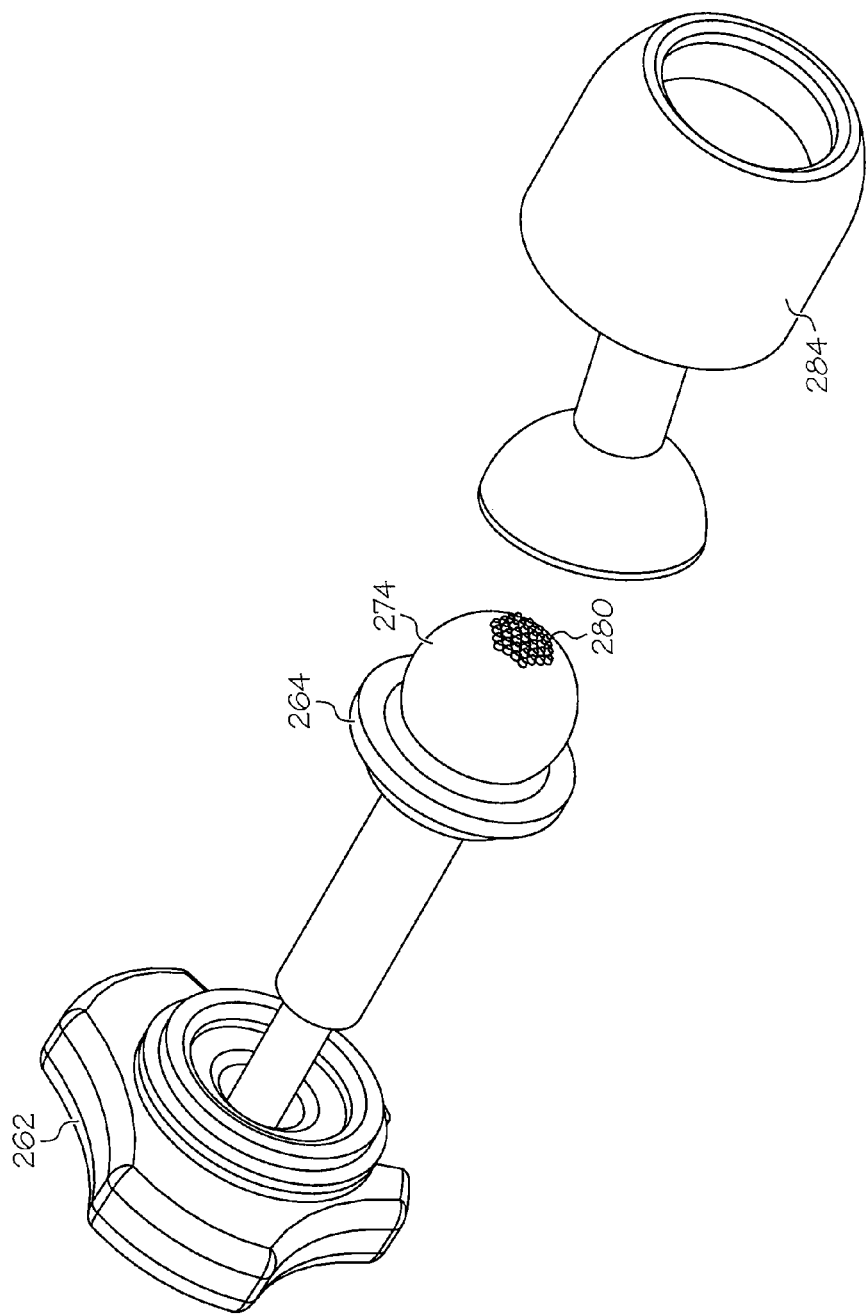

POLYAXIAL PIVOT HOUSING FOR EXTERNAL FIXATION SYSTEM

CROSS-REFERENCE TO RELATED APPLICATIONS

This application is related to and claims priority to U.S. Provisional Patent Application Ser. Nos. 61/789,429 and 61/788,414, each of which were filed on Mar. 15, 2013, the complete and entire disclosures of which are hereby expressly incorporated by reference herein.

TECHNICAL FIELD

The present teachings are related to an orthopedic external fixation system, and more particularly to an external fixation system having universal articulation units for positioning fixation components, including rings, pins, rods, bars and posts relative to a patient's anatomy.

BACKGROUND OF THE DISCLOSURE

The statements in this section merely provide background information related to the present disclosure and should not be construed as constituting prior art.

In various orthopedic surgical procedures, it is often necessary to secure or stabilize two or more portions of bone or soft tissue relative to one another. This need is often the result of a bone or soft tissue injury, such as an acute fracture of the bone. To ensure that the damaged bone fragments are capable of properly regenerating, it is important that the bone fragments be adequately stabilized during the regeneration process. To adequately stabilize the injured bone fragments and/or soft tissue, a bone distraction frame is typically installed onto the patient.

Once a distraction frame has been installed onto a patient, it is sometimes necessary to further adjust the frame to fine tune the alignment of the damaged bone fragments or soft tissue. This process, which is referred to as "fracture reduction," is typically performed under the guidance of a C-arm (X-ray) and involves the surgeon manually pulling on the transfixation pin until the bones are aligned in a desired orientation. Once the surgeon is satisfied with this alignment, the clamps of the distraction frame can then be tightened.

While many external fixation devices have proven generally effective for stabilizing bones, these conventional systems are often difficult and time consuming to adjust once assembled, particularly as the surgeon may need to manually loosen and retighten the clamps several times during the fracture reduction process. Not only is the adjustment process time consuming, but the health and safety of the surgeon is also potentially compromised, particularly as the surgeon must expose his hands to the X-ray field during the reduction process. Thus, it would be useful to have an external fixation framing system that is not only easy to assemble, but also provides the surgeon with a greater degree of flexibility in terms of safely adjusting the frame once it has been assembled.

The present application is intended to improve upon and resolve some of these known deficiencies of the art.

SUMMARY OF THE DISCLOSURE

According to a first aspect of the present teachings, a polyaxial pivot housing for an external fixation system is provided and comprises a first plate; a second plate substantially parallel to the first plate; a spherical member positioned between the first and second plates, the spherical member having a threaded post that is configured to attach to a support member of an external fixation frame; and a pivotably rotatable locking arm, the locking arm being configured to orientationally lock the threaded post with respect to the external fixation frame by compressing the first and second plates against the spherical member.

According to another aspect of the present teachings, a polyaxial pivot housing for an external fixation system is provided and comprises a first plate; a second plate substantially parallel to the first plate; a locking screw connecting the first and second plates; a spherical member positioned between the first and second plates, the spherical member having a threaded post that is configured to attach to a support member of an external fixation frame; and a pivotably rotatable locking arm, the locking arm being configured to orientationally lock the threaded post with respect to the external fixation frame by compressing the first and second plates against the spherical member; wherein the polyaxial pivot housing has a provisional locking feature and a definitive locking feature, each locking feature being manually actuatable without the use of a tool.

Other objects and benefits of the disclosure will become apparent from the following written description along with the accompanying figures.

BRIEF DESCRIPTION OF THE DRAWINGS

The above-mentioned aspects of the present disclosure and the manner of obtaining them will become more apparent and the disclosure itself will be better understood by reference to the following description of the embodiments of the disclosure taken in conjunction with the accompanying drawings, wherein:

FIG. 4A is a perspective view of the illustrative external fixation clamping assembly of FIG. 3A shown clamped to a ring frame in accordance with the teachings of the present disclosure;

FIG. 4C is a side view of the illustrative external fixation clamping assembly and ring frame of FIG. 4A;

FIG. 5C is a top view of the illustrative external fixation distraction handle assembly of FIG. 5A;

FIG. 6A is a perspective view of an illustrative external fixation distraction handle assembly extension arm in accordance with the teachings of the present disclosure;

FIG. 9A is a perspective view of a pair of external fixation polyaxial pivot housings and clamping assemblies connected to a ratcheting strut in accordance with the teachings of the present disclosure.

FIG. 19A is an exploded perspective view of another external fixation polyaxial pivot housing having a series of mating protrusions for preventing rotation in accordance with the present teachings;

DETAILED DESCRIPTION

The above-mentioned aspects of the present application and the manner of obtaining them will become more apparent and the teachings of the present application itself will be better understood by reference to the following description of the embodiments of the present application taken in conjunction with the accompanying drawings.

The embodiments of the present application described below are not intended to be exhaustive or to limit the teachings of the present application to the precise forms disclosed in the following detailed description. Rather, the embodiments are chosen and described so that others skilled in the art may appreciate and understand the principles and practices of the present application.

Unless defined otherwise, all technical and scientific terms used herein have the same meaning as commonly understood by one of ordinary skill in the art to which this application belongs. Although any method and materials similar or equivalent to those described herein can be used in the practice or testing of the present application, the specific methods and materials are now described.

Figure 1A:
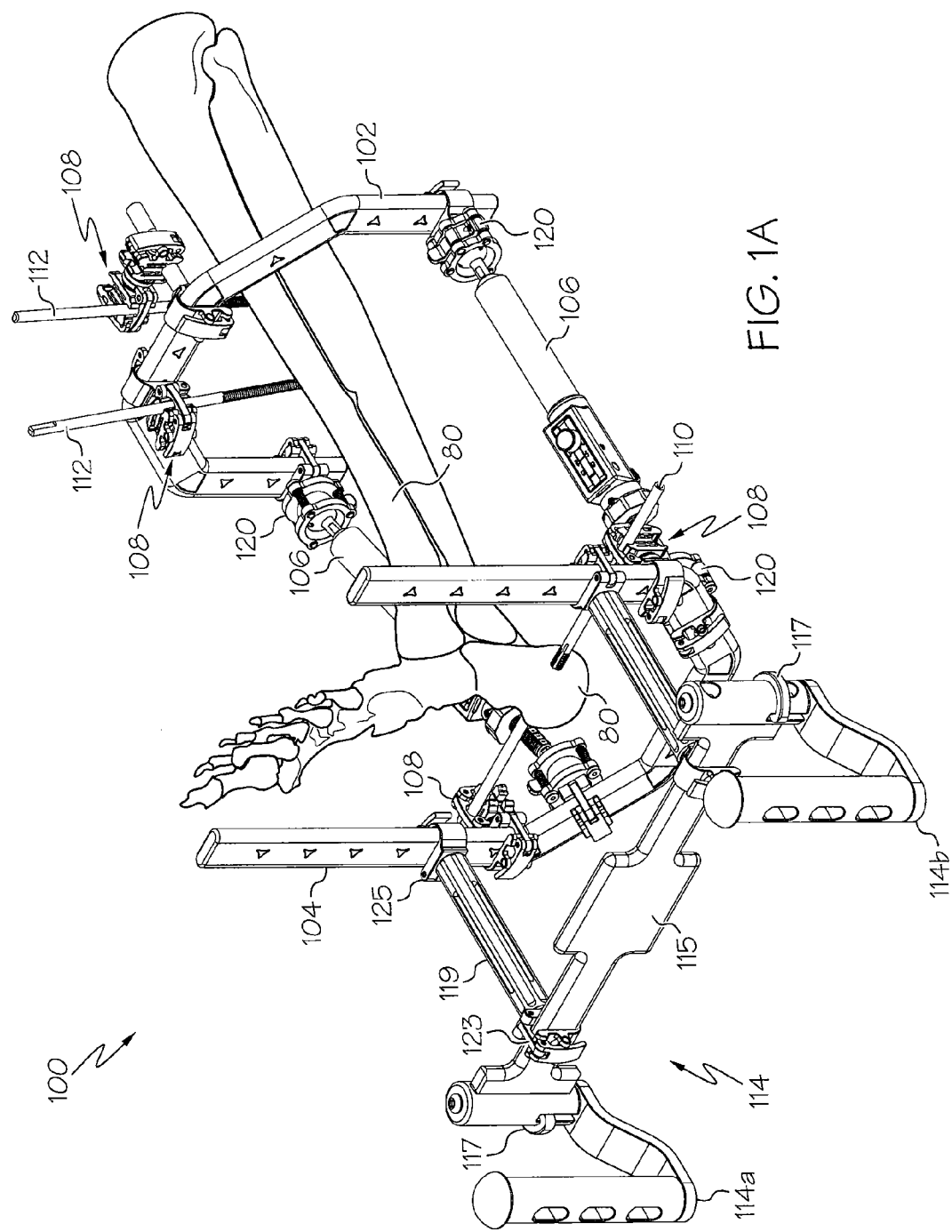
FIG. 1A is a perspective view of an ankle spanning external fixation system in accordance with the teachings of the present disclosure.

Referring to FIG. 1A, an illustrative ankle spanning external fixation frame system 100 for fixating various bones or bone portions 80 in accordance with the teachings of the present disclosure is illustrated in an environmental view. While this illustrative embodiment depicts the external fixation system 100 associated with a patient's lower extremity, it should be understood and appreciated herein that the teachings of the present disclosure may similarly be utilized on any skeletal portions of the human anatomy, including portions of the human anatomy beyond a patient's lower extremity. Moreover, while the illustrative embodiment depicted in FIG. 1A depicts an ankle spanning external fixation frame, it should be understood and appreciated herein that other lower extremity frame configurations can also be used in accordance with the teachings of the present disclosure. Such other lower extremity frames include, but are not limited to, a mid-shaft tibia spanning frame (such as frame 101 shown in FIG. 1B) and a knee spanning frame (such as frame 103 shown in FIG. 1C).

Figure 1B:
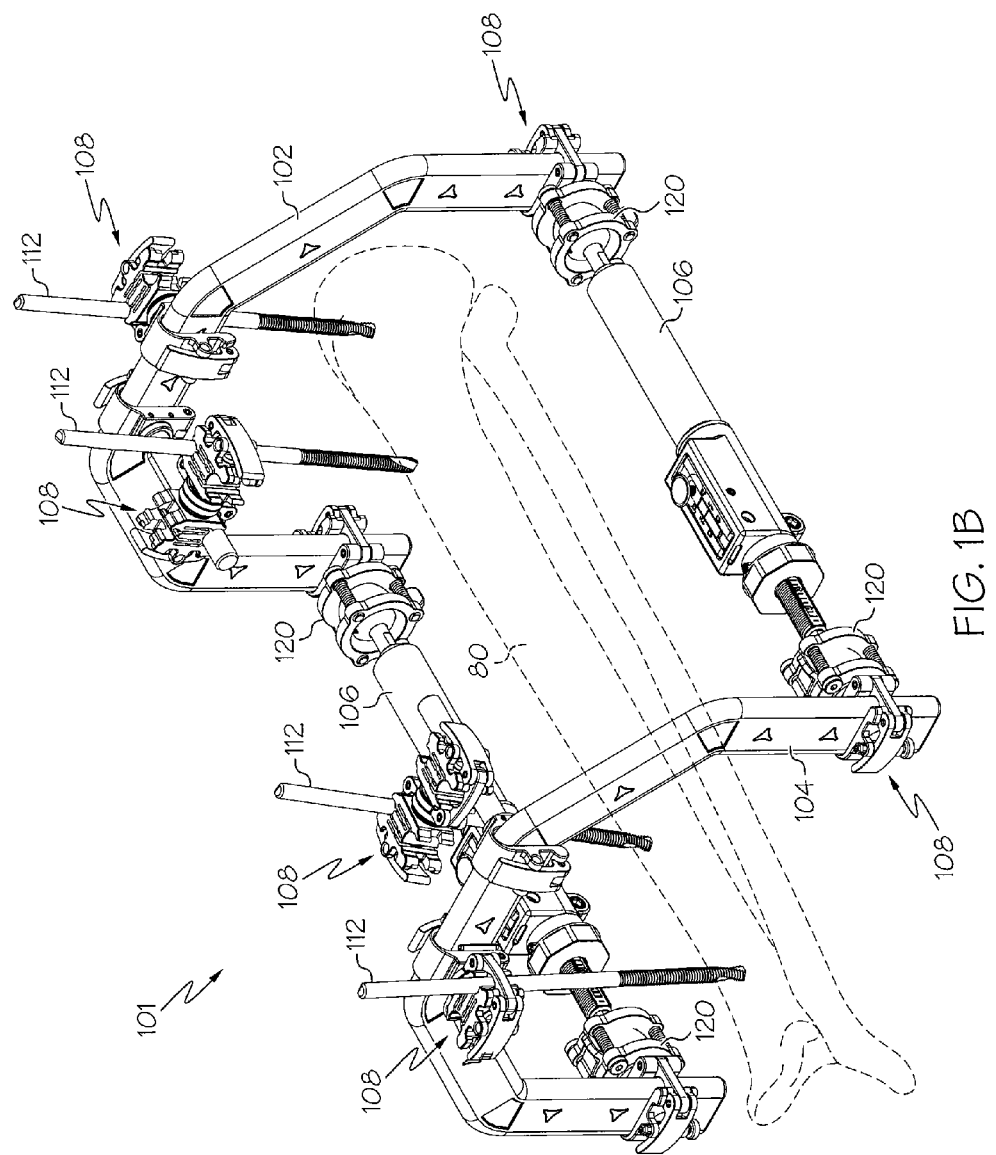
FIG. 1B is a perspective view of a mid-shaft tibia spanning external fixation system in accordance with the teachings of the present disclosure.
Figure 1C:
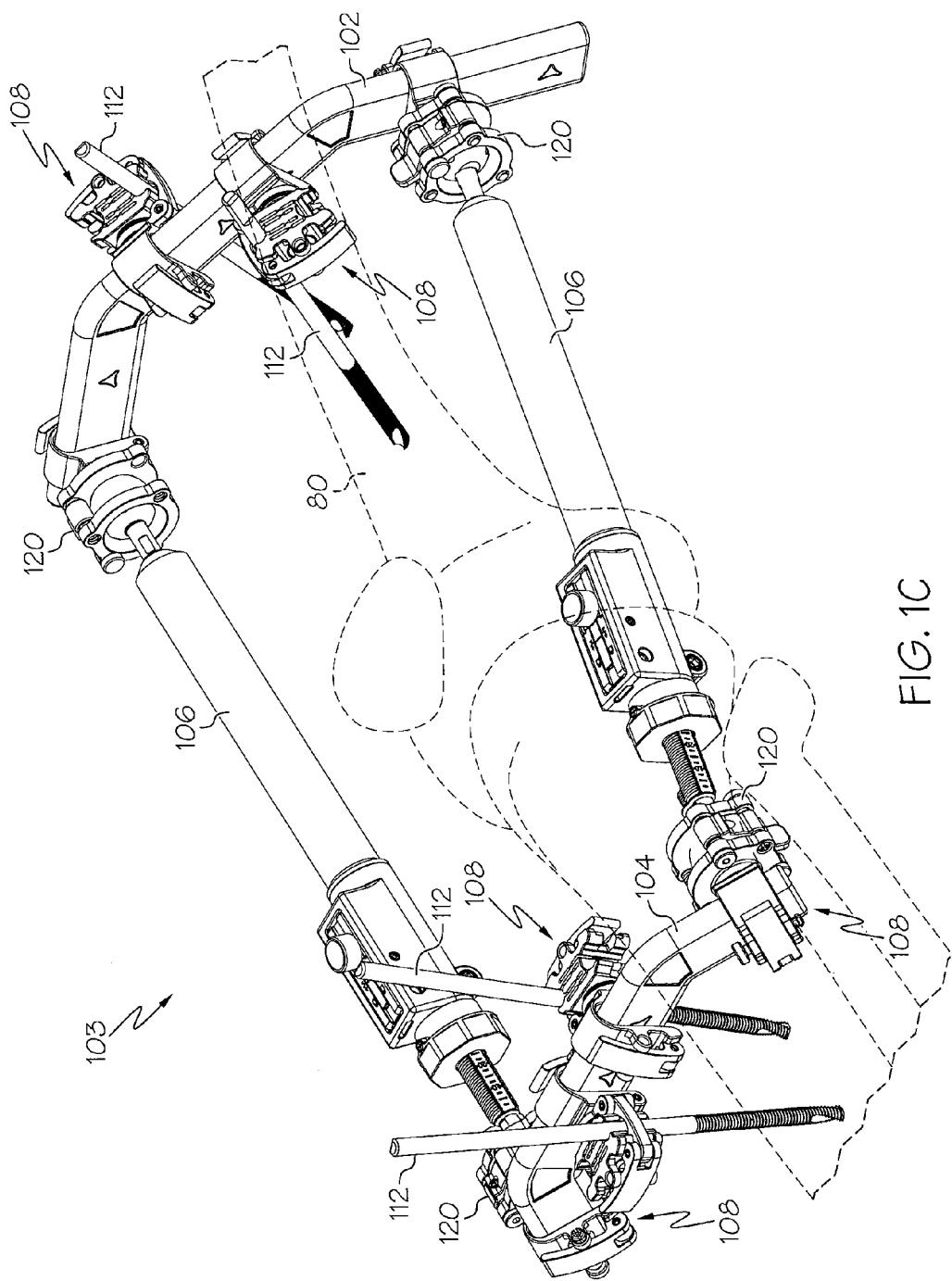
FIG. 1C is a perspective view of a knee-spanning external fixation system in accordance with the teachings of the present disclosure.

Referring specifically to FIGS. 1A, 1B and 1C, the external fixation frame systems 100, 101 and 103 each include a proximal ring frame 102 and a distal ring frame 104 positioned on opposite sides of a fracture/fusion site of a patient's bones 80. The proximal and distal ring frames 102, 104 are connected to each other by one or more frame connectors or struts (e.g., ratcheting struts) 106, which can be selected from various sizes and configurations as needed. Illustrative frame connecting struts 106 that may be used in accordance with the teachings of the present disclosure include, but are not limited to, those described in commonly assigned U.S. patent application Ser. No. 13/464,502, which was filed on May 4, 2012, and published as U.S. Patent Publication No. 2013/0296857 on Nov. 7, 2013. The entire disclosure of this application is hereby incorporated in its entirety by this reference.

Various clamps or clamping assemblies 108, which will be described in more detail below, can be used with the frame connectors 106 or independently of the frame connectors 106 for attaching bone pins or wires (e.g., transfixing pins, such as indicated by reference numeral 110), and/or rods, bars, or other fixation devices (e.g., bone screws, such as indicated by reference numeral 112) as desirable for a particular fixation procedure. While not necessarily required herein, the proximal and distal frames 102, 104, the frame connectors 106, the clamping assemblies 108, or any portions thereof, can be radiographically translucent such that the fixation system 100, 101 and 103, when installed, can allow viewing of a fracture/fusion site of the bones 80 on X-ray film. The radiolucent components (or portions thereof) can be formed of, for example, carbon, composite, carbon fiber, or other radiolucent materials.

As will be explained in detail below, various different kinds of clamping assemblies 108 may be used with the external fixation systems 100, 101 and 103 of the present teachings. The type, number, size and order of the various clamping assemblies used to assemble the external fixation frame will not only depend on what type of fixation procedure is being performed, but will also depend on the amount of rotational and translational degrees of freedom desired between the interconnected components. Some of the components that may be interconnected by the clamping assemblies of the present disclosure include, but are not necessarily limited to, proximal and distal ring frames 102, 104, frame connector struts 106, bone screws 112, pins 110, wires, rods, bars, shafts, and other such fixation devices.

Figure 2A:
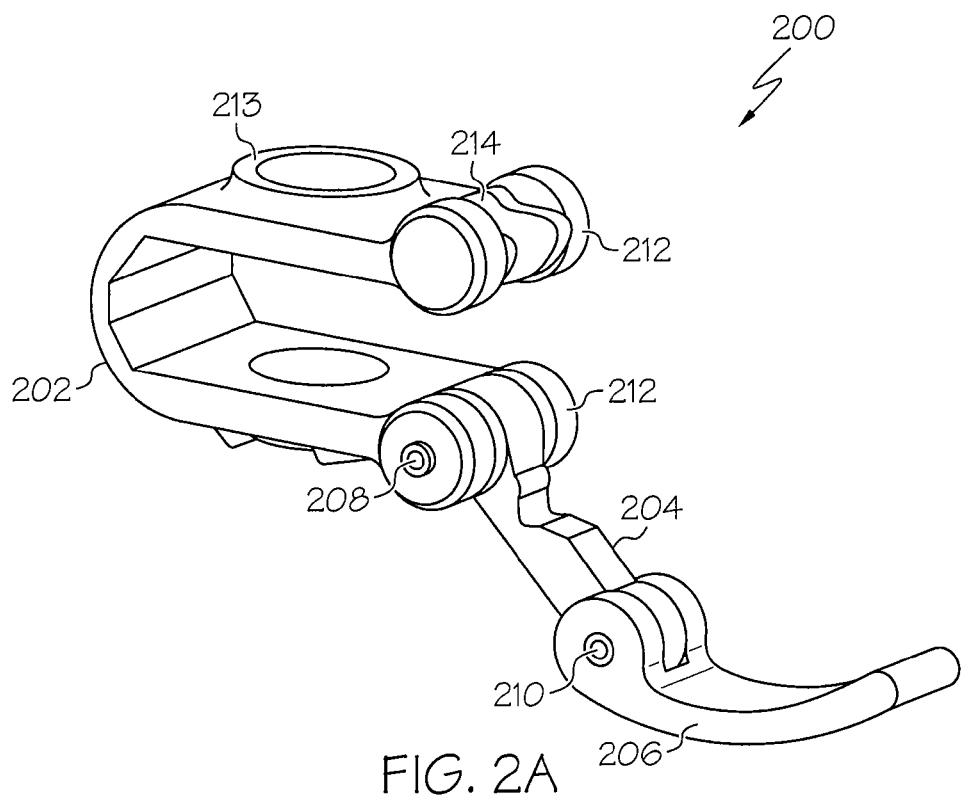
FIG. 2A is a perspective view of an illustrative external fixation clamping assembly having its locking arm in the open position in accordance with the teachings of the present disclosure.
Figure 2B:
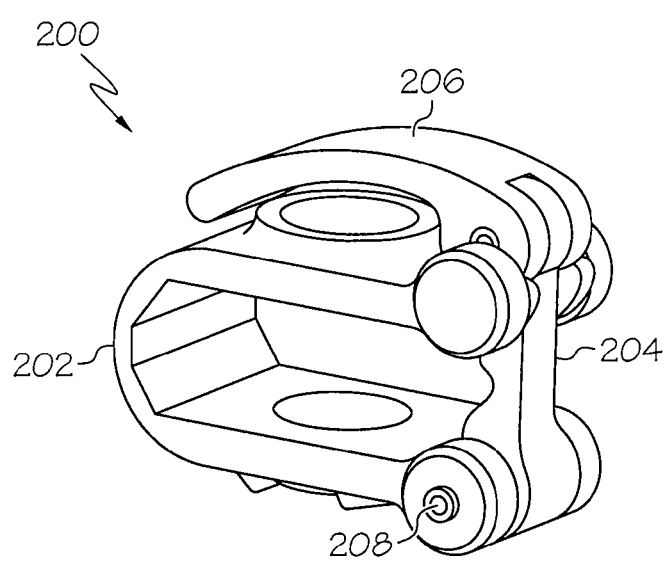
FIG. 2B is a perspective view of the illustrative external fixation clamping assembly of FIG. 2A having the locking arm in the closed position.
Figure 4B:
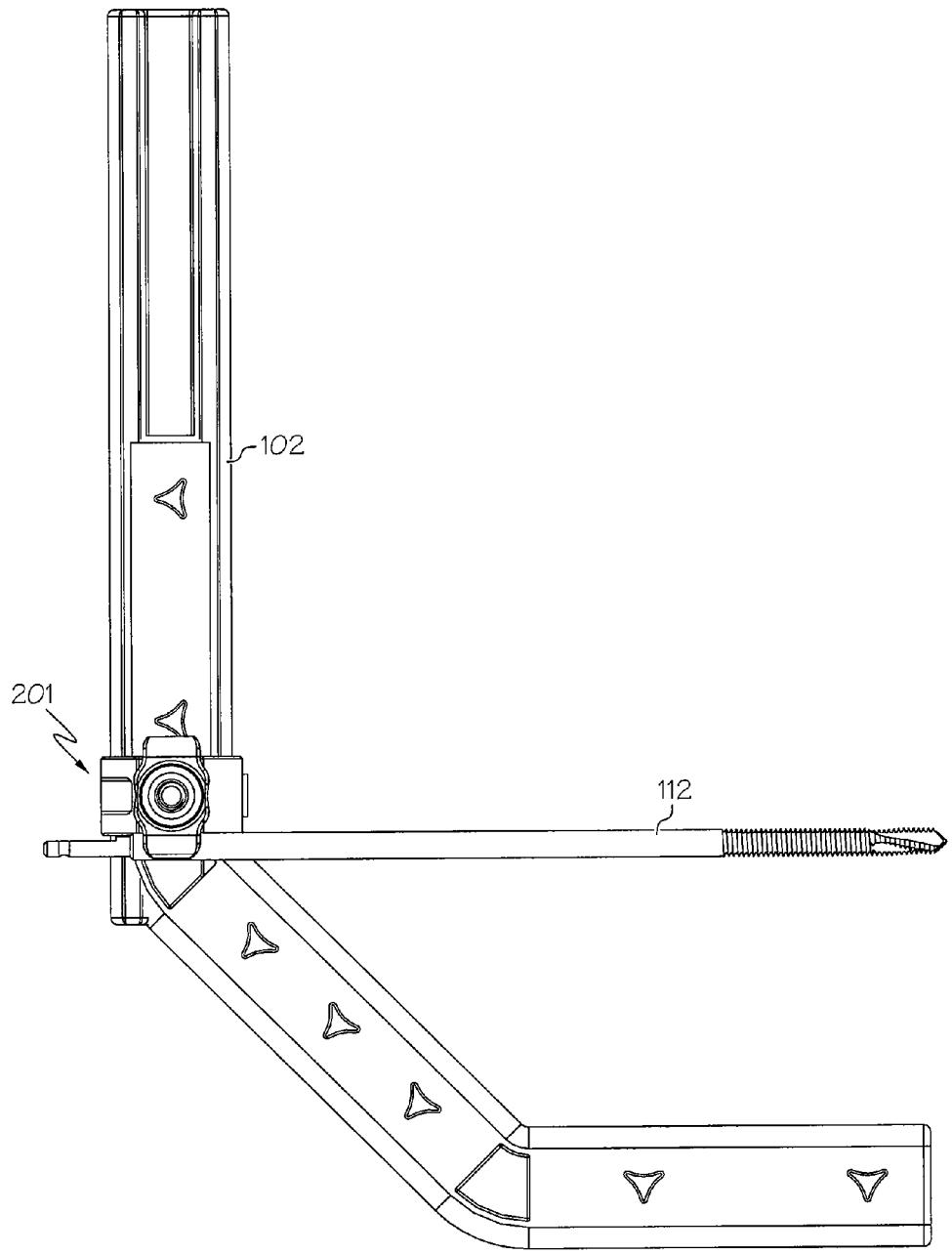
FIG. 4B is a top view of the illustrative external fixation clamping assembly and ring frame of FIG. 4A.
Figure 5A:
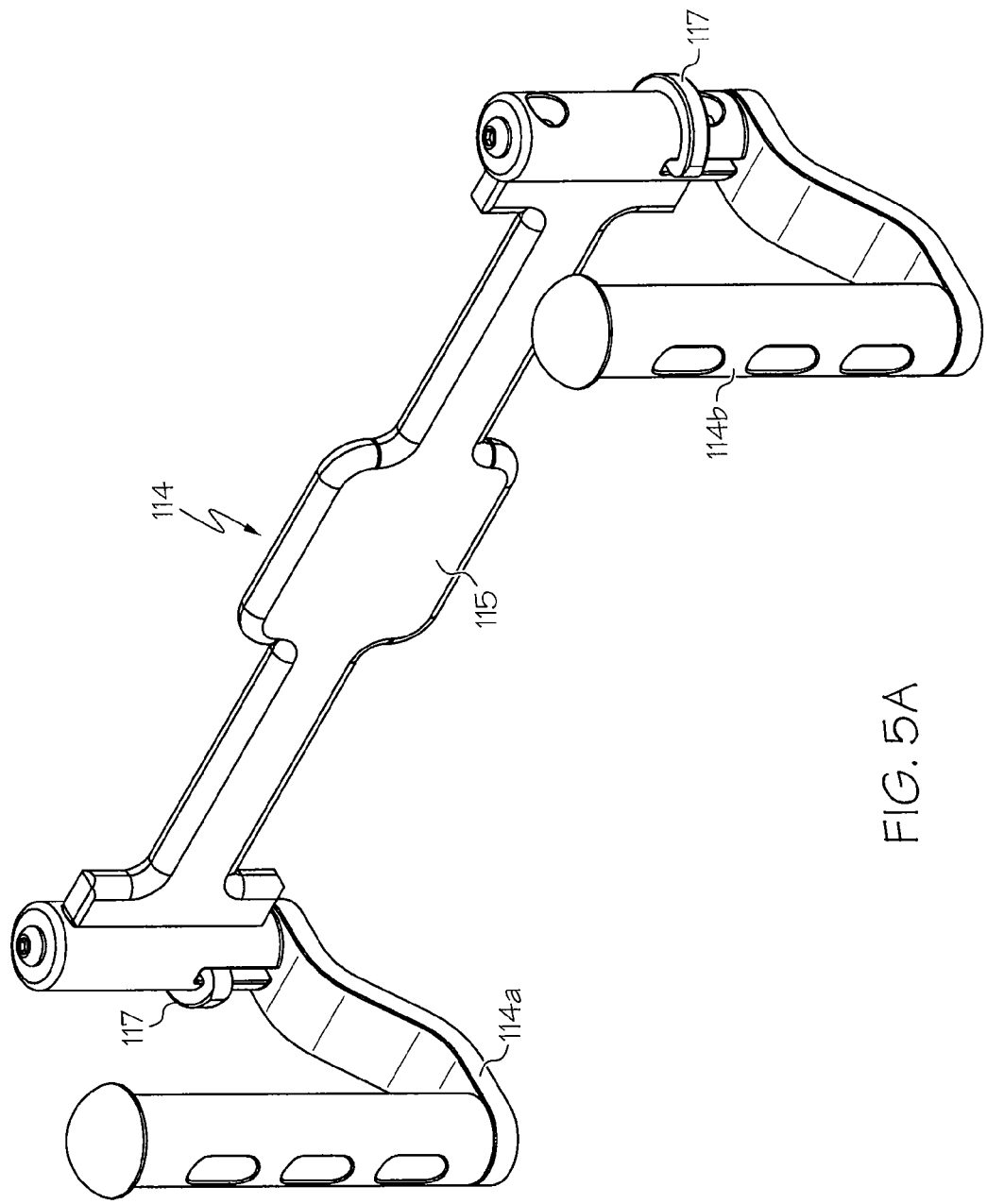
FIG. 5A is a perspective view on an illustrative external fixation distraction handle assembly in accordance with the teachings of the present disclosure.
Figure 5B:
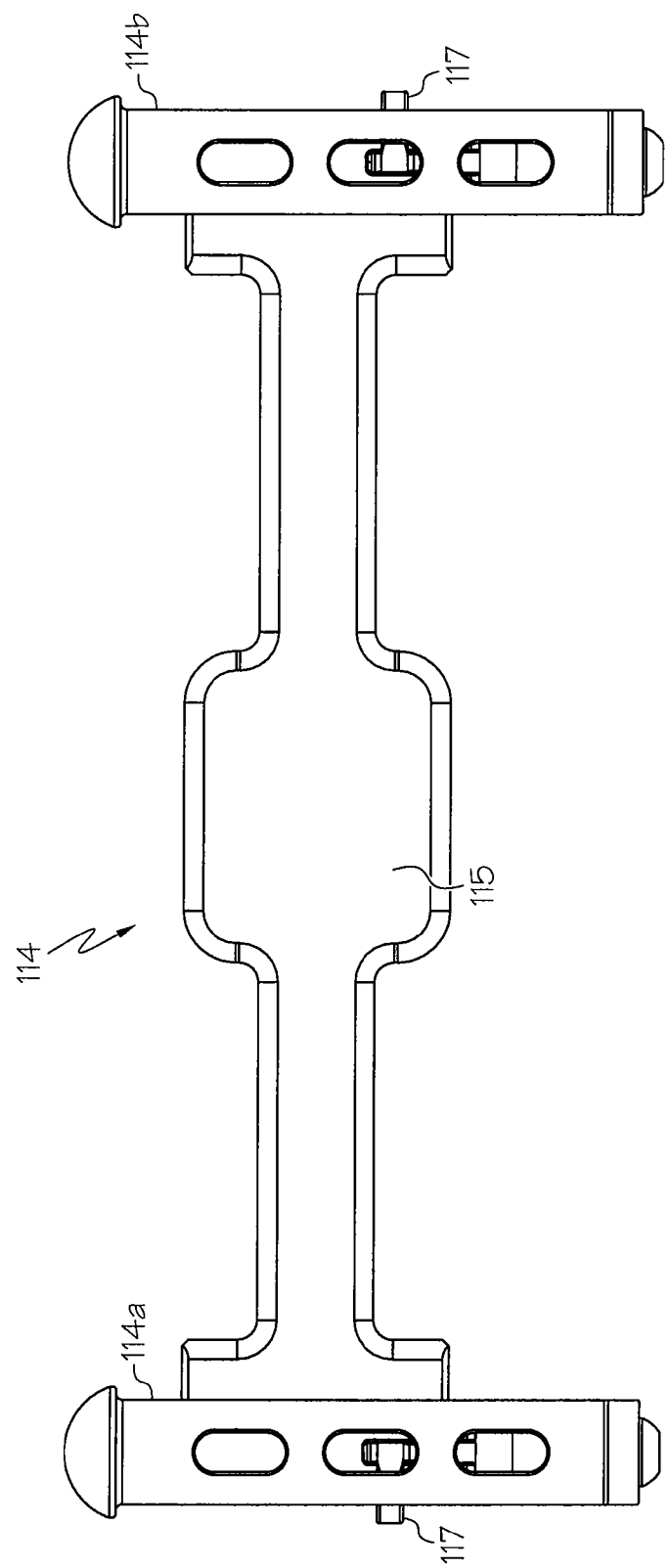
FIG. 5B is a front view of the illustrative external fixation distraction handle assembly of FIG. 5A.
Figure 5D:
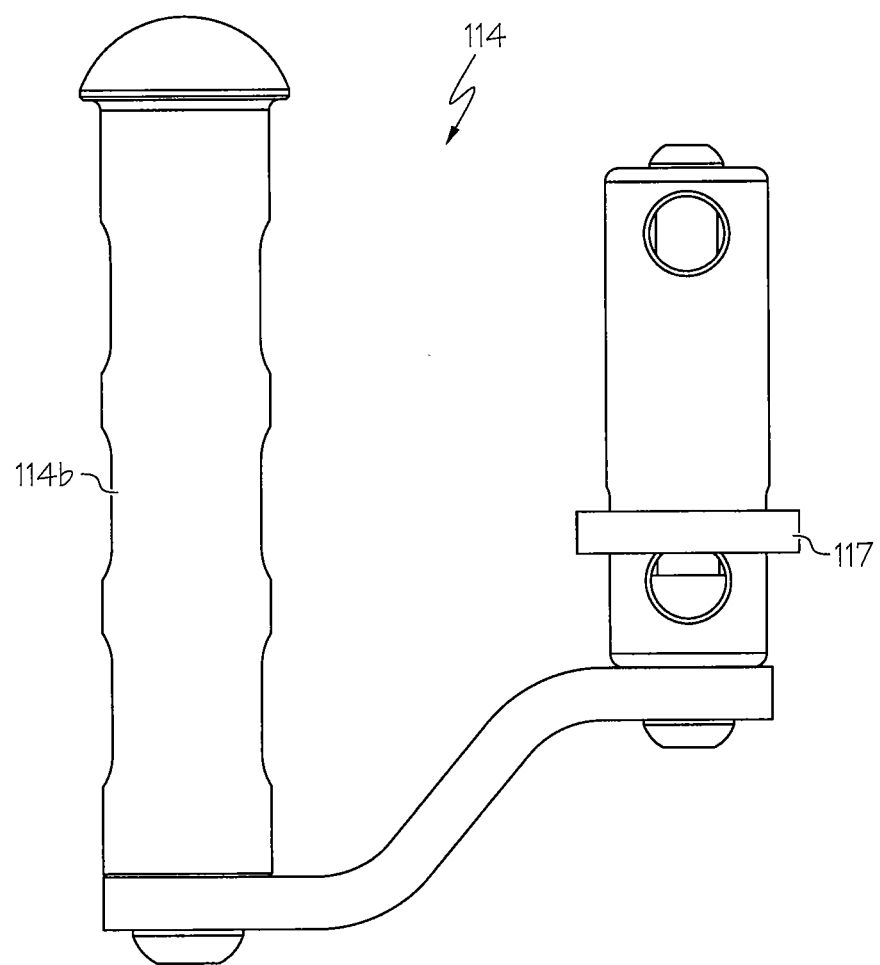
FIG. 5D is a side view of the illustrative external fixation distraction handle assembly of FIG. 5A.

Referring now to various clamping assemblies 108 that may be used in accordance with the present disclosure, FIGS. 2A and 2B depict a first illustrative clamping assembly 200 that includes a clamp body 202, a locking arm 204, a cam arm 206, a locking arm pivot pin 208 and a cam arm pivot pin 210. During assembly of an external fixation frame system 100, 101, 103, the clamping assembly 200 is configured to be snapped onto a ring frame 102, 104 or a rod by positioning the clamp body 202 substantially perpendicular to the ring leg or rod and applying pressure to force end jaws 212 open and over the ring or rod (see FIGS. 4A, 4B and 4C, for instance, which illustrates an illustrative clamping assembly 201 attached to a ring frame 102). Alternatively, the clamping assembly 200 can be snapped onto the ring frame or rod by positioning the clamp body 202 at the end of a ring leg or rod and applying pressure to slide the body onto the ring or rod.

Once positioned on the ring frame 102, 104 or rod, the locking arm 204 is actuatable to compress and center the ring frame or rod inside the clamp body 202. To achieve this, the clamp may be provisionally locked by rotating the locking arm 204 (via the locking arm pivot pin 208) towards and into a cam arm pocket 214. Once the surgeon is satisfied with the position and fixation of the bone fragments 80, the frame or fixator is definitively locked without the use of additional tools or equipment. To achieve the definitive lock, the cam arm 206 is rotated towards the clamp body 202 via the cam arm pivot pin 210 located at the center of the cam arm 206 until it approximates a top surface 213 of the clamp body 202.

Figure 3A:
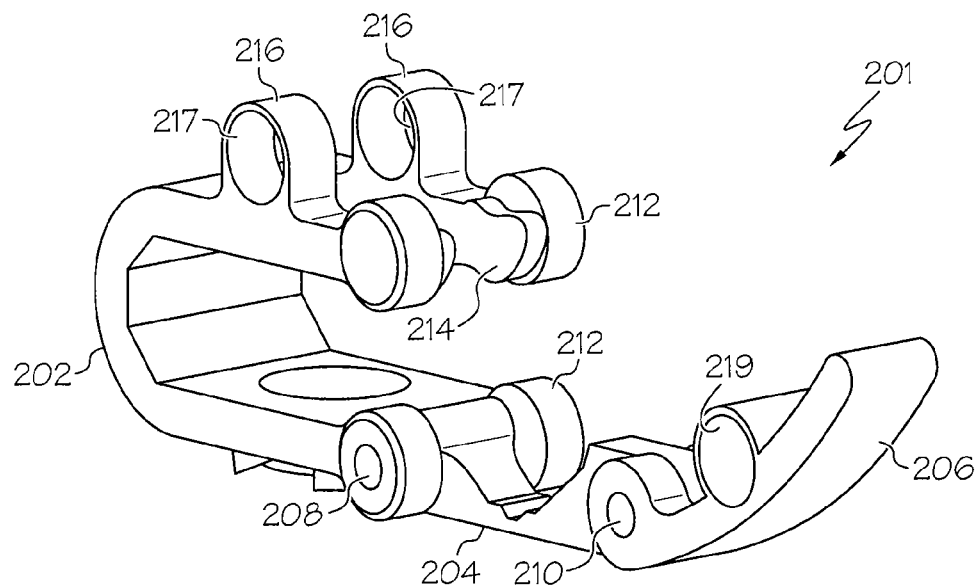
FIG. 3A is a perspective view of another illustrative external fixation clamping assembly having its locking arm in the open position and having a pair of upwardly projecting locking tabs that are configured to secure the locking arm in place in accordance with the teachings of the present disclosure.
Figure 3B:
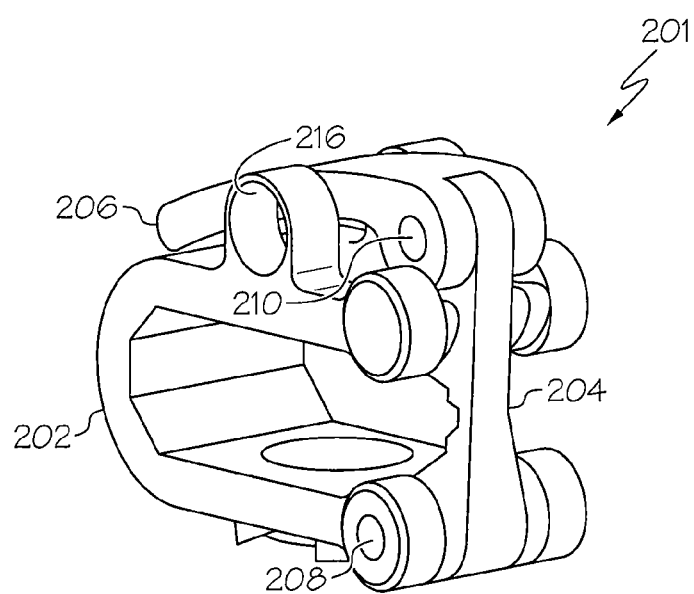
FIG. 3B is a perspective view of the illustrative external fixation clamping assembly of FIG. 3A having the locking arm in the closed position.
Figure 3C:
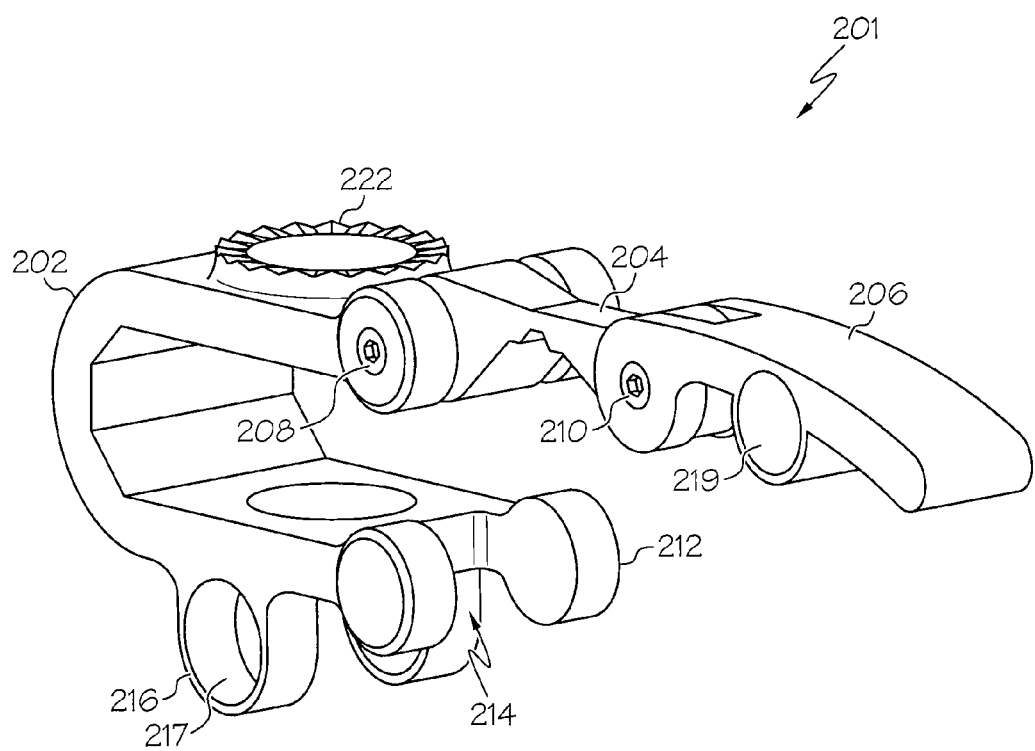
FIG. 3C is an inverted perspective view of the illustrative external fixation clamping assembly of FIG. 3A showing a serrated surface for rotationally locking a stack of clamping assemblies relative to one another.

Once the cam arm 206 is positioned against the clamp body 202 during a definitive locking process, in accordance with certain aspects of the present disclosure, the cam arm 206 can be further locked into place by utilizing a locking pin that is configured to be inserted through the cam arm 206. More particularly, FIGS. 3A, 3B and 3C illustrate a clamping assembly 201 having a pair of upwardly projecting tabs 216 extending from the clamp body 202 and each having a through-hole 217 formed therein. When the cam arm 206 is positioned against the clamp body 202, the through-holes 217 align with a through-hole 219 formed into the cam arm 206 such that a common through-hole is created. The locking pin (such as locking pin 144) can then be inserted through this common through-hole, thereby preventing the cam arm 206 from being lifted away from the clamp body 202 until the locking pin 144 is first removed.

By being able to provisionally lock any of the presently disclosed clamping assemblies, the surgeon is not only able to construct the frame or fixator on the patient as presented (i.e., the frame can adapt to the patient's unique anatomy as opposed to requiring the patient's anatomy to first be adjusted in order to fit the frame), but the surgeon can perform the process without needing to utilize additional tools or equipment. As such, the surgeon will be able to position, align and stabilize the bone fragments with the assistance of a C-arm (X-ray) by directly manipulating the frame itself.

To position, align and stabilize the bone fragments once a clamping assembly (such as clamping assembly 200 or 201, for instance) is provisionally locked to the fixation frame, in accordance with certain aspects of the present disclosure, a distraction handle assembly 114 connected to the distal ring frame 104 can be utilized. In accordance with this aspect of the present disclosure, and specifically referring to FIGS. 5A-5D, the distraction handle assembly 114 includes a pair of distraction handles 114A, 114B that can be manually gripped by the surgeon to adjust the frame during the fracture reduction process as needed. In other words, the surgeon grips the distraction handles 114A, 114B and manipulates (e.g., pulls, pushes, twists) the handles as needed, thereby causing the frame 100, 101 and 103 to respond and change its orientation with respect to the patient's anatomy.

The pair of distraction handles 114A, 114B are connected by a cross bar assembly 115, which provides a gripping feature for the distraction arms. In accordance with certain aspects of the present teachings, the distraction handle assembly 114 may include a handle lock ring 117 that is configured to lock the handle assembly 114 in an open position during its operation. More particularly, in accordance with certain aspects of the present disclosure, the distraction handle assembly 114 is capable of being adjusted between two position—i.e., a first position (open state) where the distraction handles 114A, 114B are at 90° to the cross bar 115 and a second position (closed state) where the handles are collapsed against the cross bar. To rotate the arms from the open state to the closed state, the user pulls up on each of the lock rings 117 located around the handle pivot and rotates the handle assembly towards the cross bar.

Figure 6B:
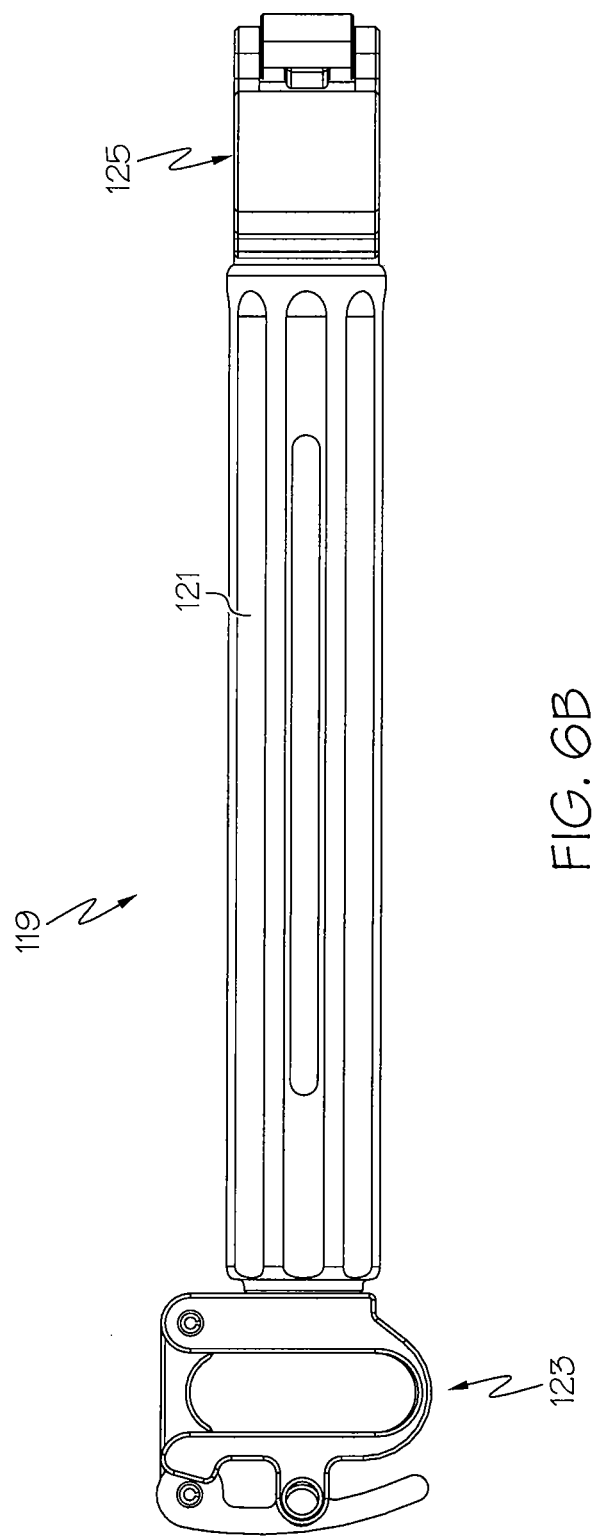
FIG. 6B is a side view of the illustrative external fixation distraction handle assembly extension arm of FIG. 6A.

In addition, and to ensure that the surgeon is able to safely adjust the external fixation assembly frames 100, 101 and 103 without exposing his or her hands to the X-ray field during the adjustment process, the handles 114A, 114B of the distraction handle assembly 114 are extended from the distal ring frame 104 via a pair of distraction extension arms 119 (see FIGS. 1A, 6A and 6B). According to certain aspects herein, each extension arm 119 has a barrel 121 that provides a connection between the cross bar assembly 115 and the distal ring frame 104. A fixed ring/cross bar clamp 123 connects to the ring 104 or cross bar 115 in a fixed position, while a pivoting ring/cross bar clamp 125 connects the ring 104 or cross bar 115 in such a manner that it is rotatable 360°. As those of skill in the art will understand and appreciate herein, the basic concept for the use of the distraction handle assembly 114 is to connect the assembly to the pre-constructed external fixation frame (i.e., frames 100, 101 and 103) via the use of two distraction arm extension assemblies 119. The distraction handle assembly is configured to be used by a surgeon as an instrument to assist in the distraction and alignment of bone fractures which are "provisionally" stabilized by the frame, as well as to protect or reduce the intensity of exposure to imaging radiation by allowing the surgeon to position his or her hands away from the frame during a radiological event.

Unlike traditional external fixation systems that require surgeons to lock and unlock various portions of the frame in order to manually adjust and manipulate the orientation of the fixation frame with respect to a patient's anatomy, the external fixation frame systems 100, 101 and 103 of the present disclosure are capable of being polyaxially adjusted (e.g., adjustment along several different axes) through a range of motion having a 360-degree pattern from a longitudinal axis (without the use of additional tools or equipment) while the frame is provisionally locked into place. To achieve such polyaxial adjustment, an adjustable pivot housing 120 is incorporated into the external fixation frame system 100, 101 and 103 and is applied to the patient's bones prior to reducing the fracture. As used herein, the term "polyaxial" or "polyaxially" refers to the ability of a first element to pivot in multiple planes with respect to a second element to which the first element is coupled. The adjustable locking polyaxial pivot housing 120 can be used with either a bilateral frame system or a unilateral frame system. When incorporated into the external fixation frame system, it allows the surgeon to provisionally position the bone fragments via C-arm (X-ray) to align, stabilize and prevent additional neurovascular damage without the need to definitively lock the frame by means of additional instruments or actions.

Figure 7A:
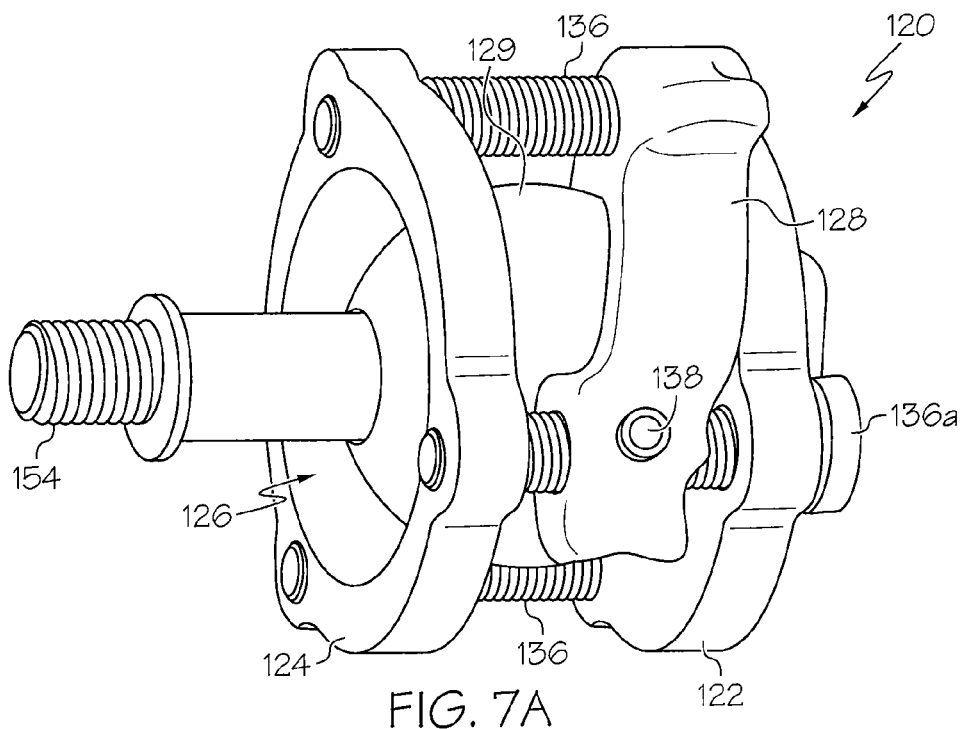
FIG. 7A is a perspective view of an external fixation polyaxial pivot housing in accordance with the teachings of the present disclosure.
Figure 7B:
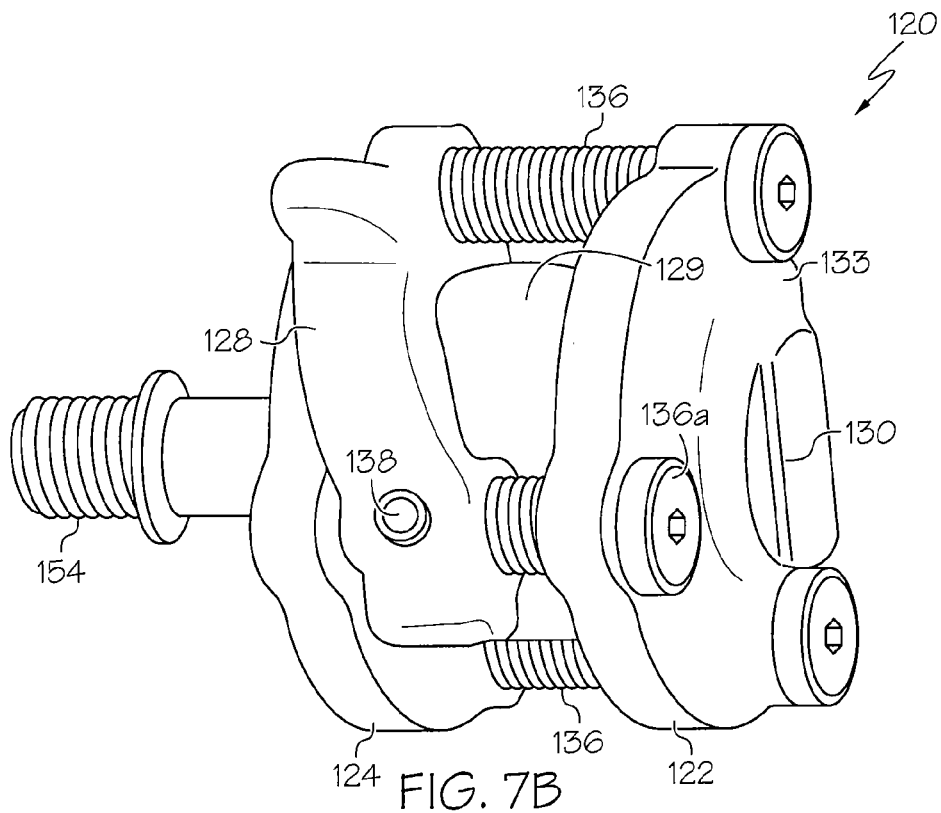
FIG. 7B is another perspective view of the external fixation polyaxial pivot housing of FIG. 7A.
Figure 7C:
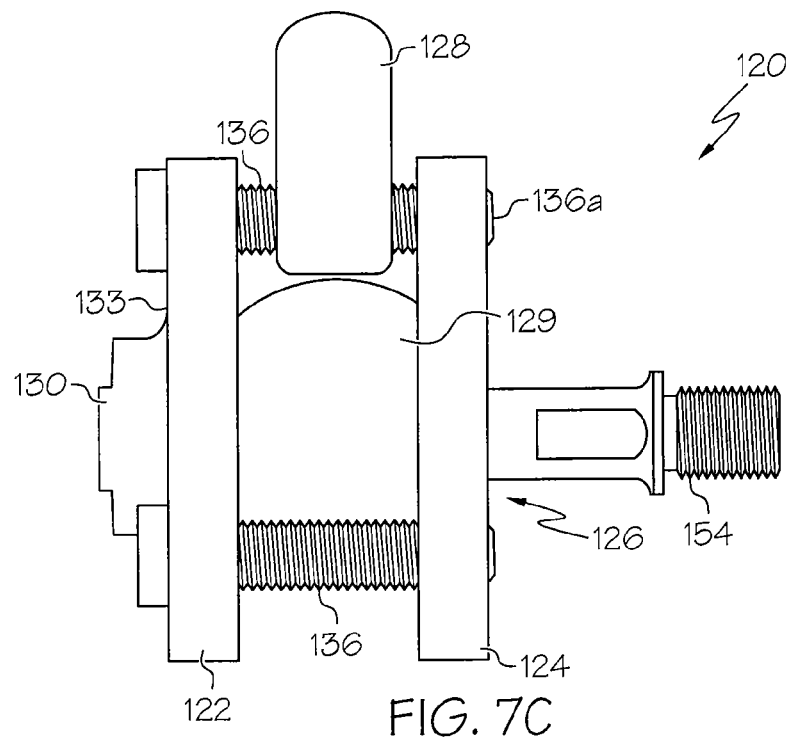
FIG. 7C is a side view of the external fixation polyaxial pivot housing of FIG. 7A.
Figure 7D:
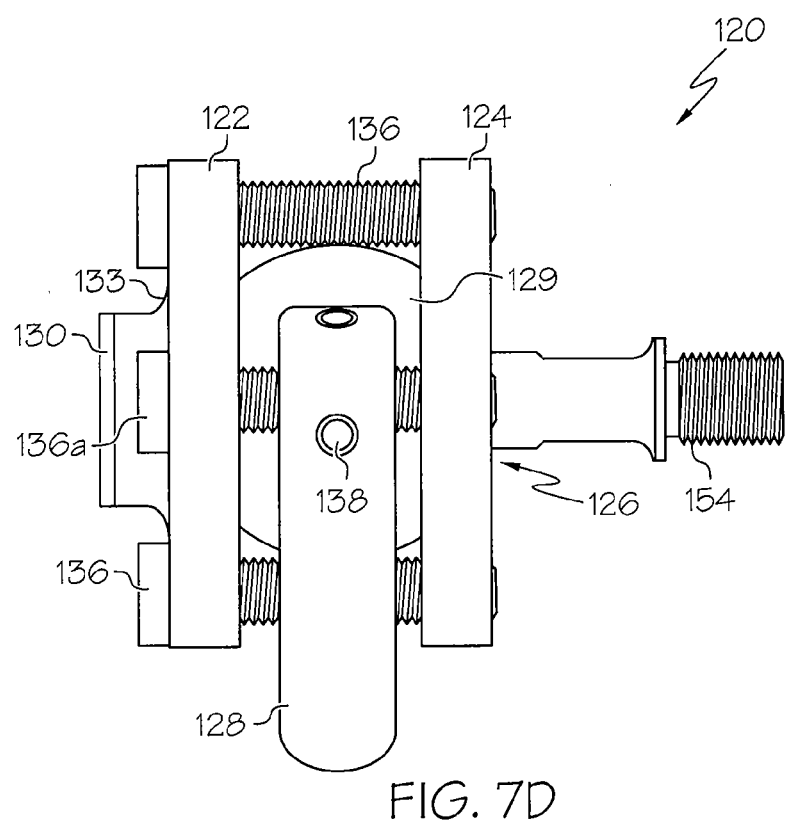
FIG. 7D is another side view of the external fixation polyaxial pivot housing of FIG. 7A.
Figure 7E:
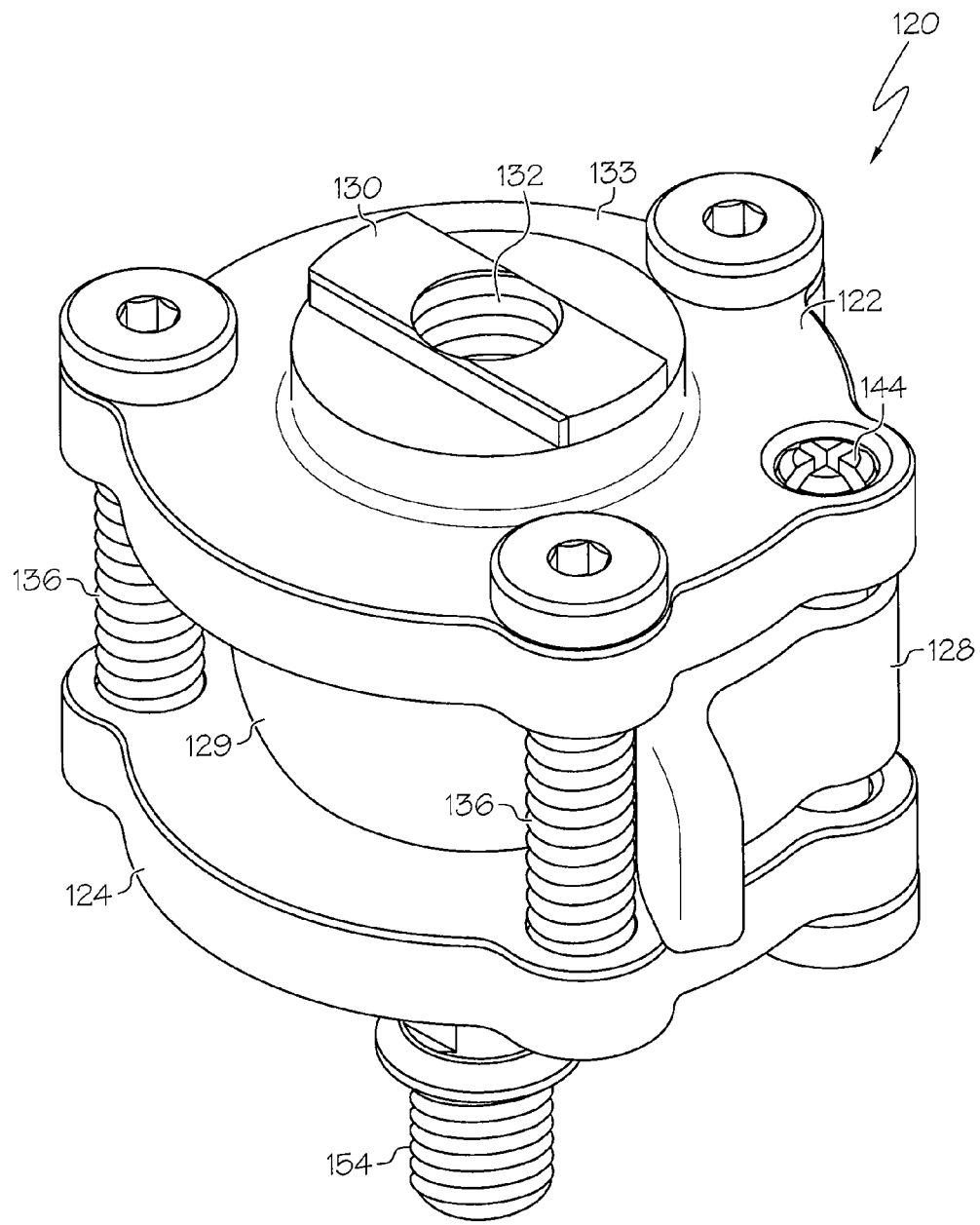
FIG. 7E is another perspective view of the external fixation polyaxial pivot housing of FIG. 7A.
Figure 7F:
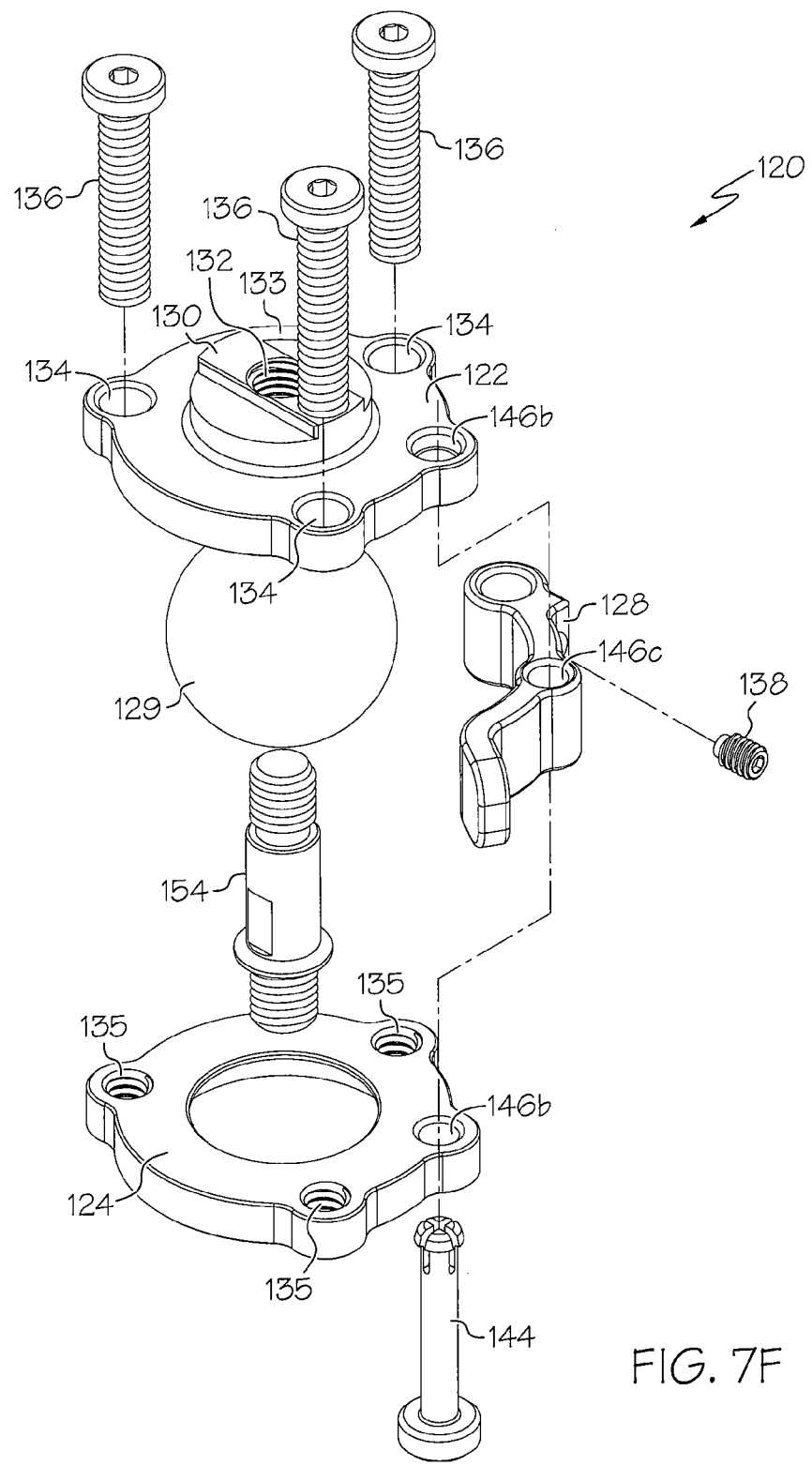
FIG. 7F is an exploded perspective view of the external fixation polyaxial pivot housing of FIG. 7A.
Figure 7G:
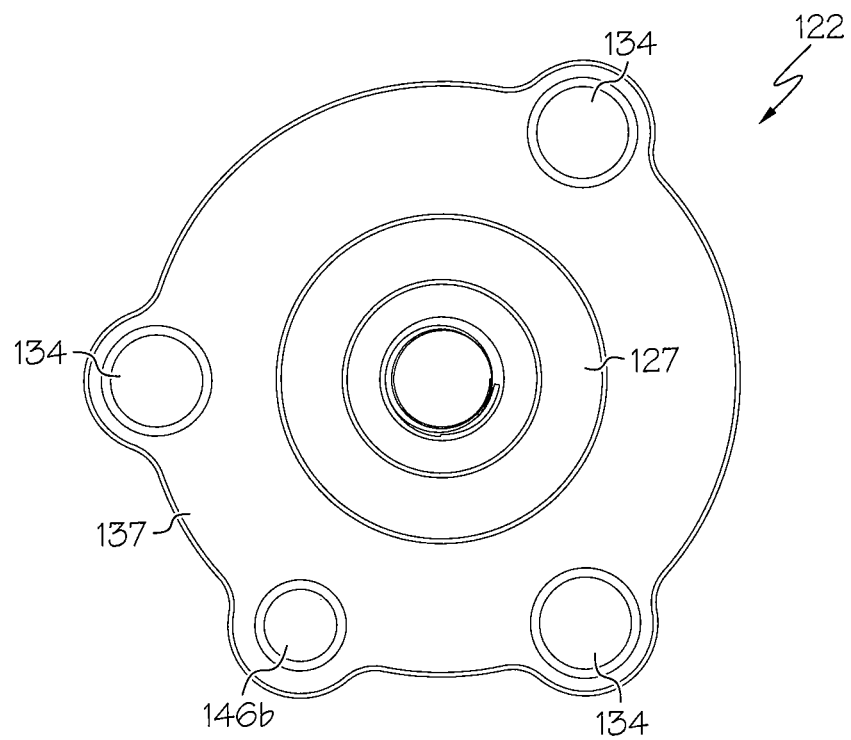
FIGS. 7G-7H are the respective top and bottom housing rings of the polyaxial pivot housing FIG. 7A.
Figure 7H:
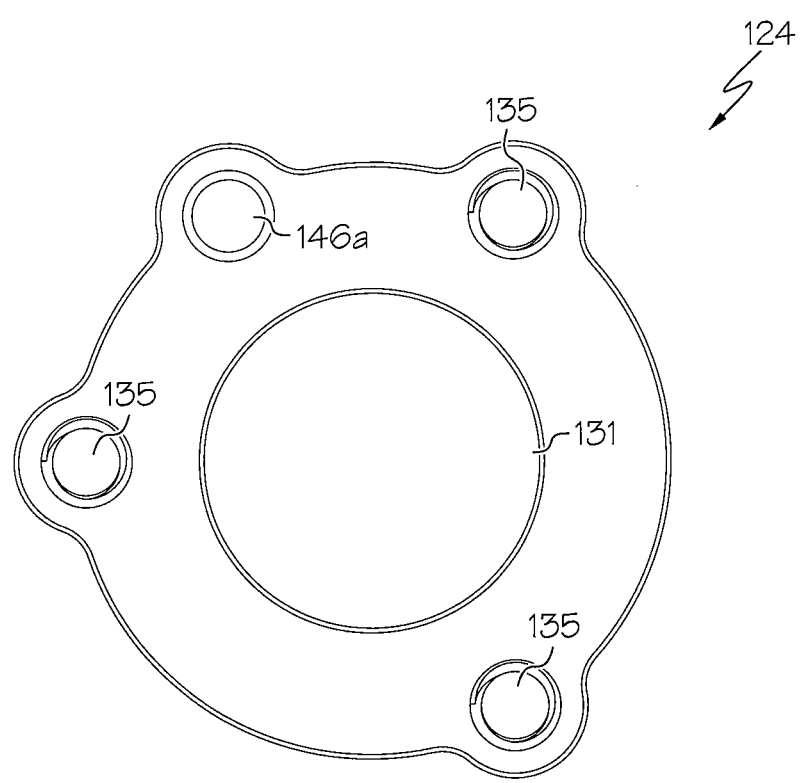

Various views of a polyaxial pivot housing in accordance with one illustrative embodiment of the present disclosure is shown in FIGS. 7A-7H. In accordance with this illustrative embodiment, the polyaxial pivot housing 120 includes a top ring 122, a bottom ring 124, a sphere/post assembly 126 and a locking arm 128. The top ring 122 has a platform 130 extending from its top surface 133 that is configured to connect to a clamping assembly (clamping assembly 200 or 201, for example) by threading the clamp into a threaded bore hole 132 of the platform 130. When the housing 120 is assembled, the top ring 122 provides a compressive loading along with the bottom ring 124 to thereby hold and center the sphere/post assembly's spherical body 129 therebetween. As shown in FIG. 7G, to hold and center the spherical body 129 in response to the compressive loading of the top ring 122, the bottom surface 137 of the top ring 122 includes a substantially circular recessed cavity 127 that is dimensioned to accept the top portion of the spherical body 129 as the pivot housing 120 is locked relative to the frame. Similarly, as shown in FIG. 7H, the bottom ring 124 includes a substantially circular cavity 131 that is dimensioned to accept the bottom portion of the spherical body 129 as the housing is locked into place.

The top ring 122 also includes three clearance holes 134 adapted to receive locking bolts 136 that pass through the top ring 122 and thread into the bottom ring 124 via three corresponding threaded holes 135. Because of the threaded relationship between the locking bolts 136 and the bottom ring 124, when the frame 100, 101 and 103 is initially adjusted by the surgeon by pulling upon the distraction handle assembly 114, the locking bolts 136 allow the polyaxial pivot housing 120 to be provisionally locked into place in response to the compressive forces and tension applied to the spherical body 129 by the top and bottom rings 122, 124 (i.e., it achieves a friction fit). Specifically, the provisional lock is obtained when the top and bottom rings 122, 124 are positioned so that the compressive force is applied to the spherical body 129 to prevent movement by soft-tissue forces. The friction fit and soft tissue tension allows the surgeon to provisionally lock the frame and make minor adjustments to the bone alignment. Once the surgeon is satisfied with the fixation of the bone fragments, the frame can then be definitively locked to maintain the bone fragments within the desired alignment.

To definitively lock the housing 120, in accordance with certain embodiments herein one of the locking bolts 136A is connected to the locking arm 128 by way of a blind set screw 138 that passes through a threaded hole (not shown) of the locking arm 128 and presses against the locking bolt 136A. As the locking cam arm 128 is rotated in a clockwise direction, the set screw 138 prevents the locking bolt from moving independent of the locking arm 128. As a result, as the locking arm 128 is rotated about a longitudinal axis upon being pulled directionally towards the spherical body 129, the bottom ring 124 is caused to move towards the top ring 122, thereby compressing the spherical body 129 between the top and bottom rings 122, 124. This clockwise rotation of the locking arm 128 causes the attached set screw 138 to also turn, thereby compressing the top and bottom rings 122, 124 further against the spherical body 129 to create a "locking fit" that prevents the sphere/post assembly 126 from moving with respect to the fixation frame 100, 101 and 103.

Figure 8:
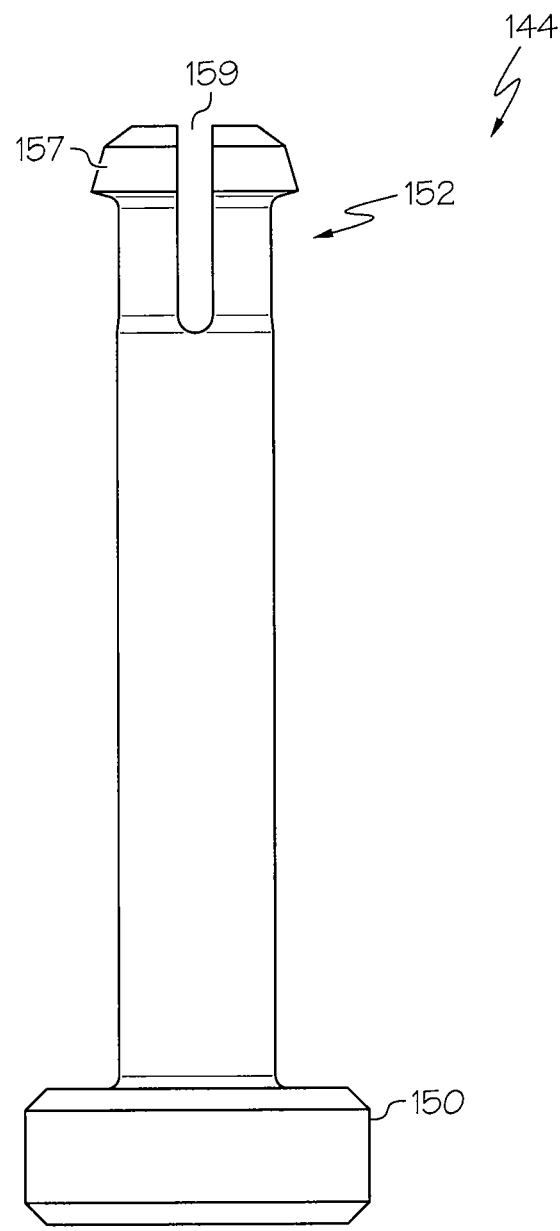
FIG. 8 is an external fixation polyaxial pivot housing locking pin in accordance with the teachings of the present disclosure.

As shown in FIGS. 7E and 8, in accordance with certain aspects of the present disclosure, the pivot housing 120 may further include a locking pin 144 that is configured to hold the locking arm 128 in place once it has been definitively locked. According to this embodiment, the top and bottom rings 122, 124, together with the locking arm 128, include a series of aligned through-holes that are configured to receive the locking pin 144 as it is inserted therethrough. Specifically, the locking pin 144 is inserted into a through-hole 146A of the bottom ring 124 from its outer surface, and particularly in such a manner that the locking pin 144 continues to pass through the through-hole of the locking arm 146c and finally into the through-hole 146B of the top ring 122. As shown in FIG. 8, the locking pin 144 includes a head portion 150 on one end and a locking mechanism 152 on its opposite end. The head portion 150 is dimensioned in such a manner that it is unable to enter the through-hole 146A of the bottom ring 124 as the locking pin is inserted therein. Since the head portion 150 has a circumferential dimension larger than that of the through-hole 146A, when the locking pin 124 is inserted therethrough, the head portion 150 is configured to serve as a stop surface as it flushingly engages the outer surface of the bottom ring 124. The locking mechanism 152 of the locking pin 124 is in turn configured to create a locking engagement with the through-hole 146B of the top ring 122 when the locking pin 124 is fully inserted therein. While various different locking arrangements may be utilized in accordance with the present disclosure, in accordance with certain illustrative aspects herein, the locking mechanism 152 may be shaped in such a manner that it creates a latching engagement with the through-hole. For instance, the locking pin 144 and/or its locking mechanism 152 may be manufactured from a material that is compressible or elastically deformable (e.g., plastic, rubber). In accordance with this illustrative aspect, the locking mechanism 152 may include a slightly flared portion 157 that is configured to compress as it passes through the through-hole 146B, yet expand back to its original dimensions after passing fully therethrough. To accomplish this expansion/retraction, a slot 159 may be formed into the locking mechanism 152 that will allow the flared portion 157 to change its circumferential dimensions by allowing it to move between an expanded and retracted position. Once returning to its original dimensions, the locking mechanism 152 will expand to a size that is slightly larger than the dimensions of the through-hole 146B, thereby locking it into place relative thereto.

Figure 9B:
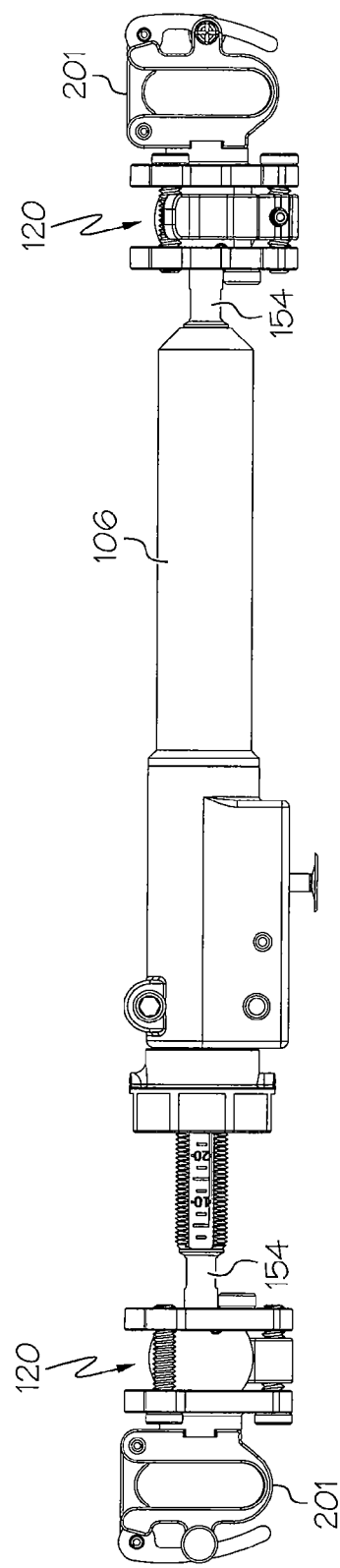
FIG. 9B is a side view of the pair of external fixation polyaxial pivot housings and clamping assemblies connected to the ratcheting strut of FIG. 9A.
Figure 10:
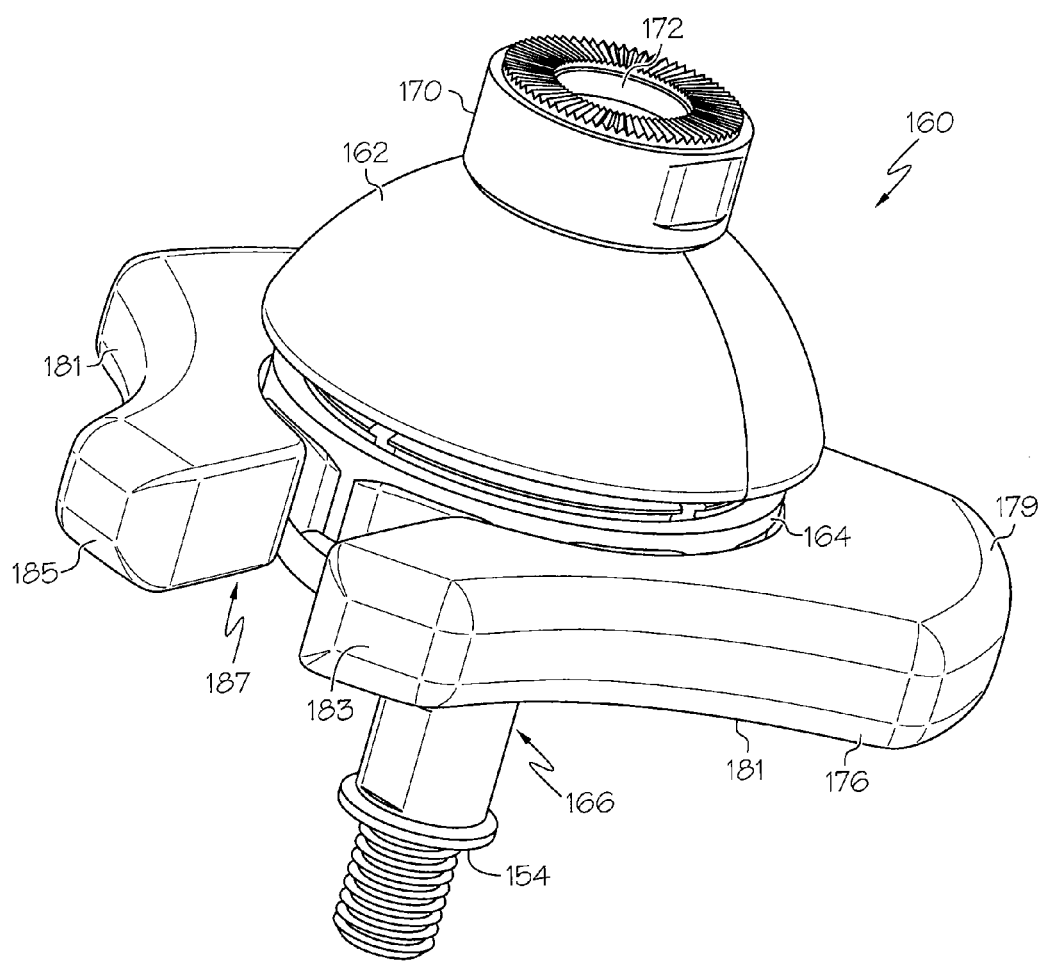
FIG. 10 is a perspective view of another external fixation polyaxial pivot housing in accordance with the teachings of the present disclosure.
Figure 11:
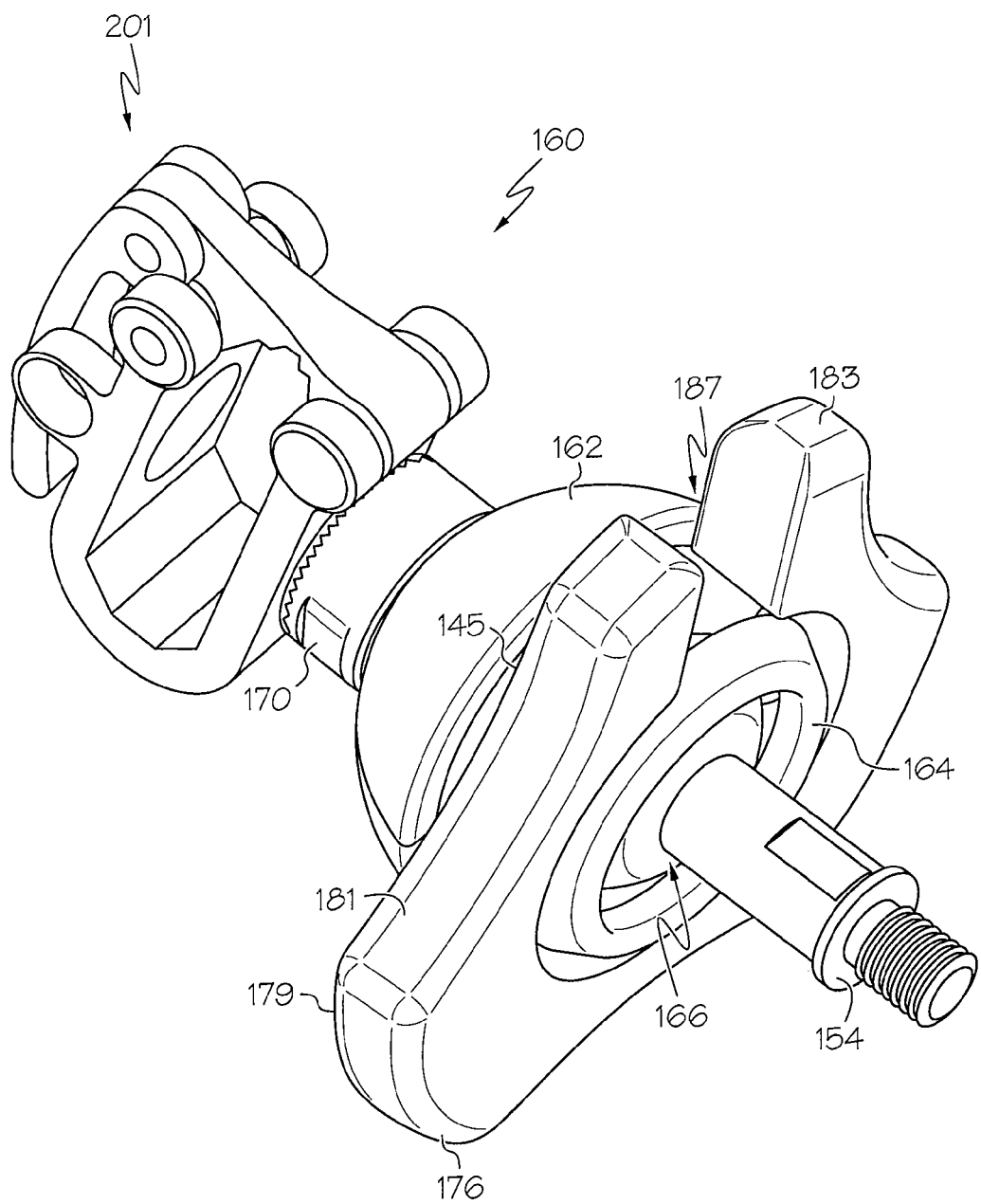
FIG. 11 is a perspective view of the external fixation polyaxial pivot housing of FIG. 10 shown associated with an illustrative external fixation clamping assembly.
Figure 12:
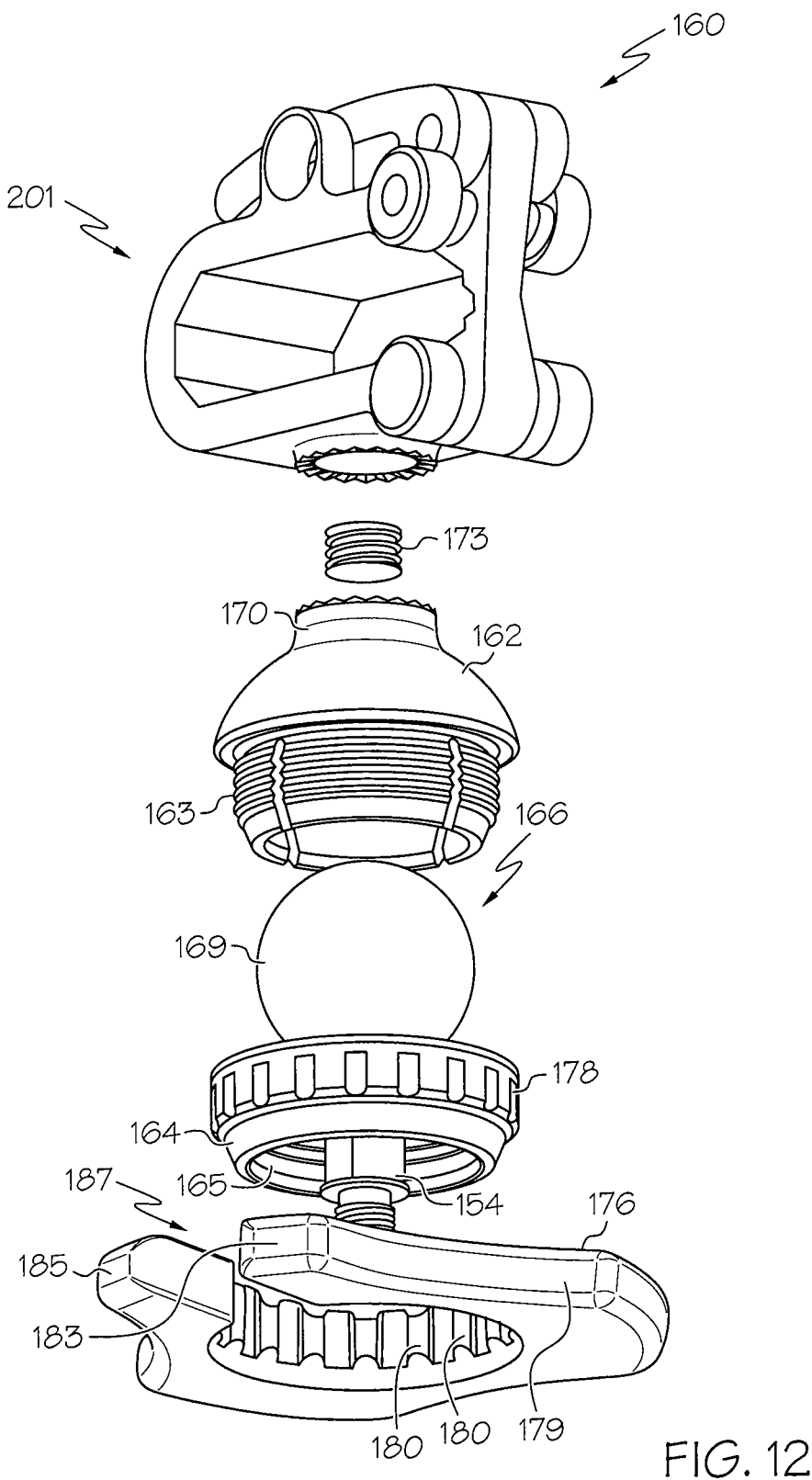
FIG. 12 is an exploded view of the external fixation polyaxial pivot housing and associated clamping assembly of FIG. 11.
Figure 14:
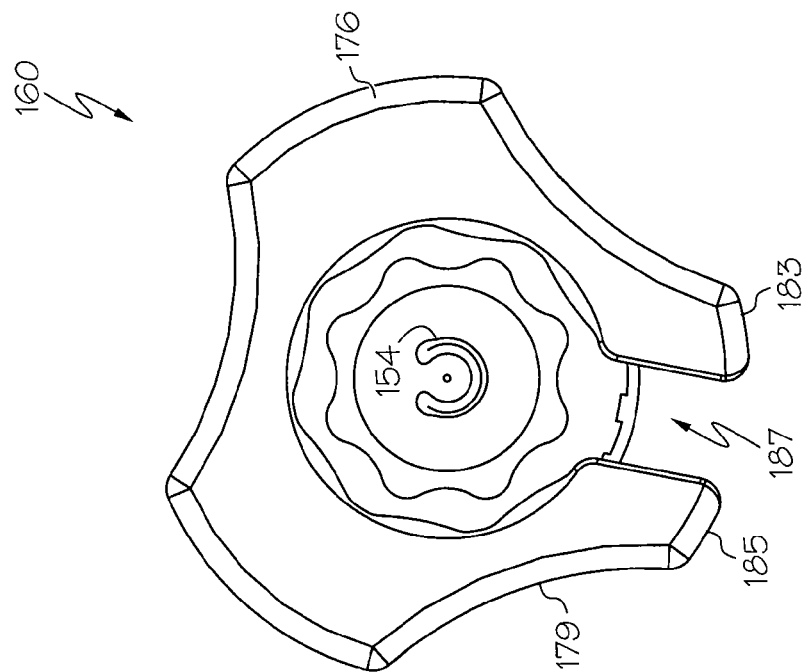
FIG. 14 is a bottom view of the external fixation polyaxial pivot housing and clamping assembly of FIG. 11.
Figure 13:
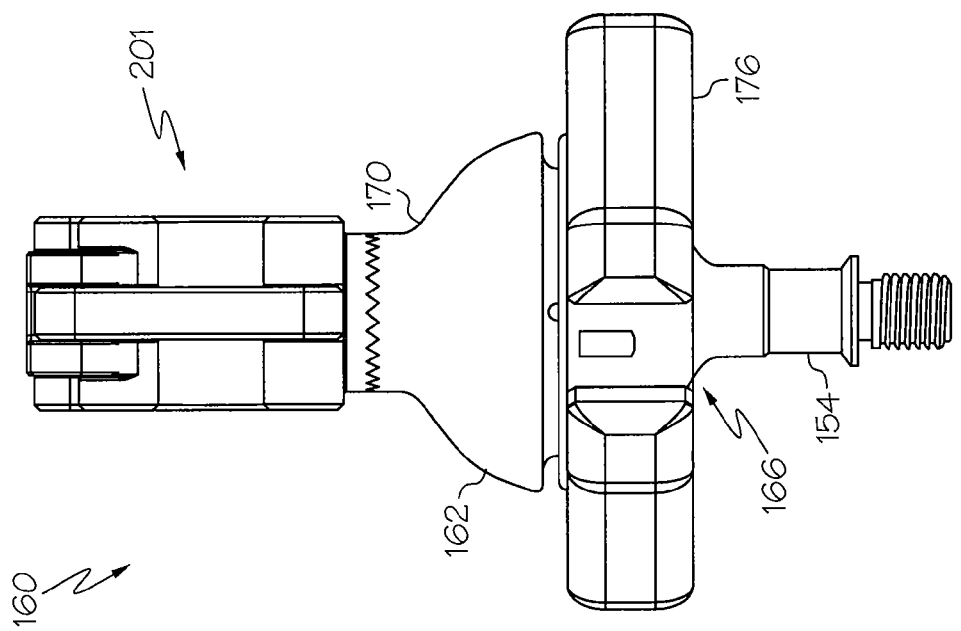
FIG. 13 is a side view of the external fixation polyaxial pivot housing and clamping assembly of FIG. 11.

Extending from the spherical body 129 is an attachment post 154 that is configured to attach the pivot housing 120 to a frame connector or ratcheting strut 106 that bridges the proximal ring frame 102 to the distal ring frame 104 (see FIGS. 9A and 9B, for instance). While the attachment post 154 and the spherical body 129 can be manufactured as a single component or unit (e.g., overmolded into a single unit), in accordance with certain aspects of the present disclosure, the attachment post 154 and the spherical body 129 may be independent of one another. For instance, the spherical body 129 may include a threaded aperture (not shown) that is configured to receive a threaded portion (not shown) of the attachment post 154.

As shown in FIGS. 10-14, another polyaxial pivot housing in accordance with the teachings of the present disclosure is illustrated. According to this embodiment, the polyaxial pivot housing 160 includes an outer collet housing 162, a compression collar or locking nut 164 and a sphere/post assembly 166. The outer collet housing 162 has a platform 170 extending from its top surface that is configured to connect to a clamping assembly (such as clamping assembly 201, for instance) by threading the clamp into a threaded bore hole 172 of the platform 170. While the platform 170 may be integral with the outer collet housing 162 such that the two are formed as a single unit, those of skill in the art will understand and appreciate herein that the platform 170 can also be manufactured as a separate piece that is in turn coupled to the housing (e.g., threaded, fused, welded, etc.).

In accordance with certain aspects of the present disclosure, the threaded bore hole 172 is configured to house a spring mechanism 173 (e.g., a coil spring), such that when the housing is assembled to an external fixation frame 100, 101, 103, the spring 173, together with soft tissue tension, allows the surgeon to provisionally lock the external fixation frame and make minor adjustments to the bone alignment as desired.

Figure 15:
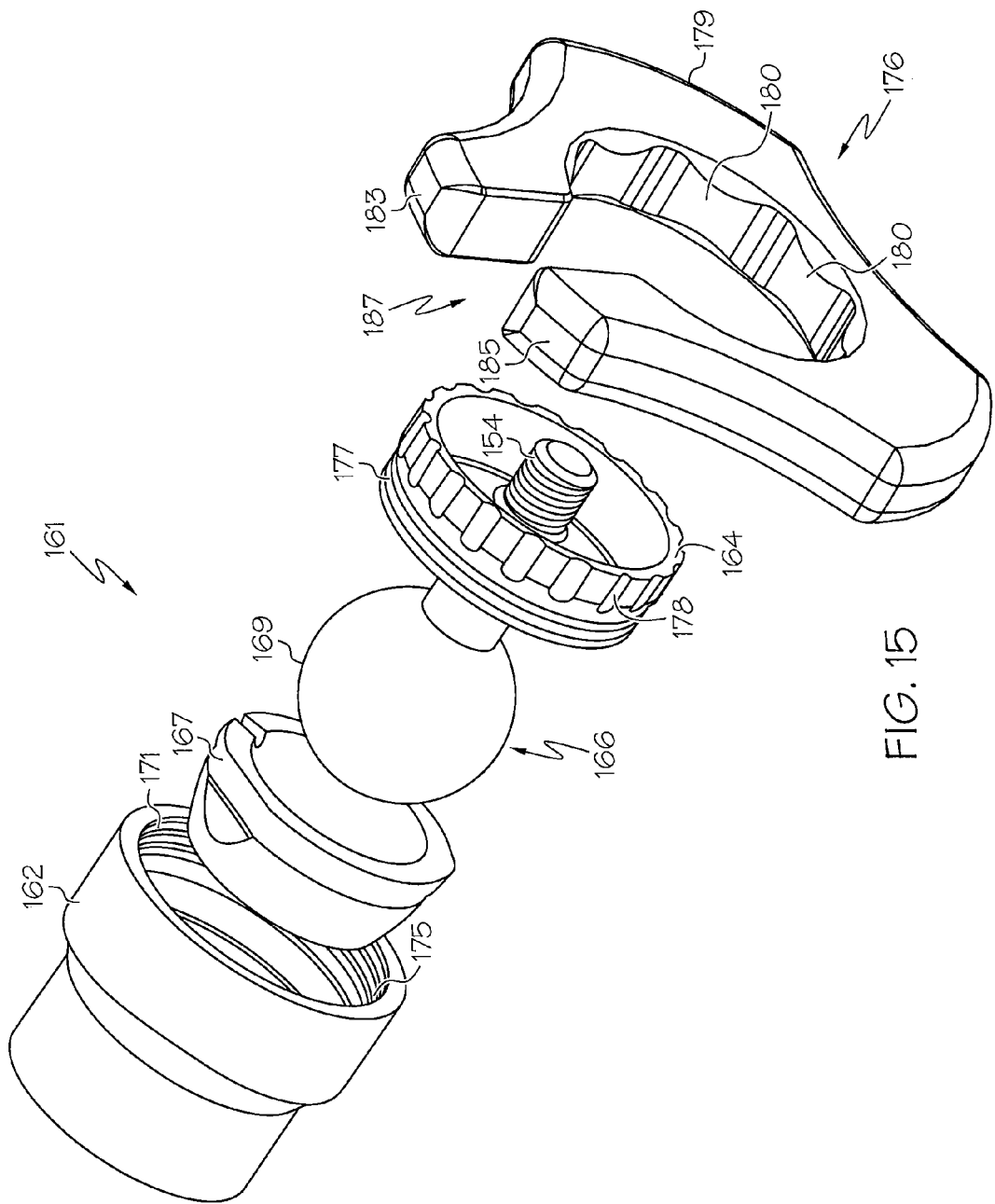
FIG. 15 is an exploded perspective view of yet another embodiment of an external fixation polyaxial pivot housing in accordance with the teachings of the present disclosure.
Figure 16A:
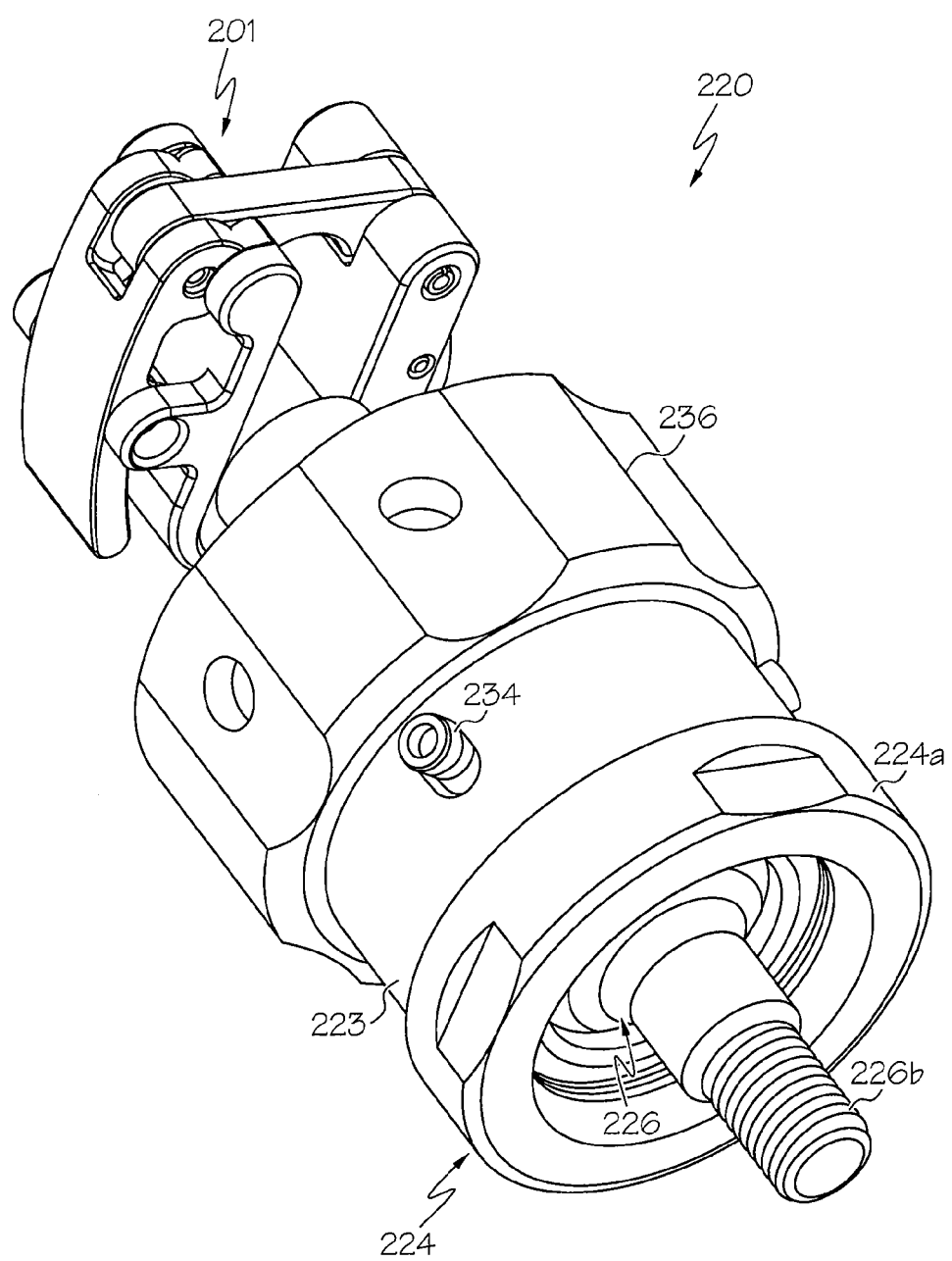
FIG. 16A is a perspective view of still another embodiment of an external fixation polyaxial pivot housing in accordance with the teachings of the present disclosure.
Figure 16C:
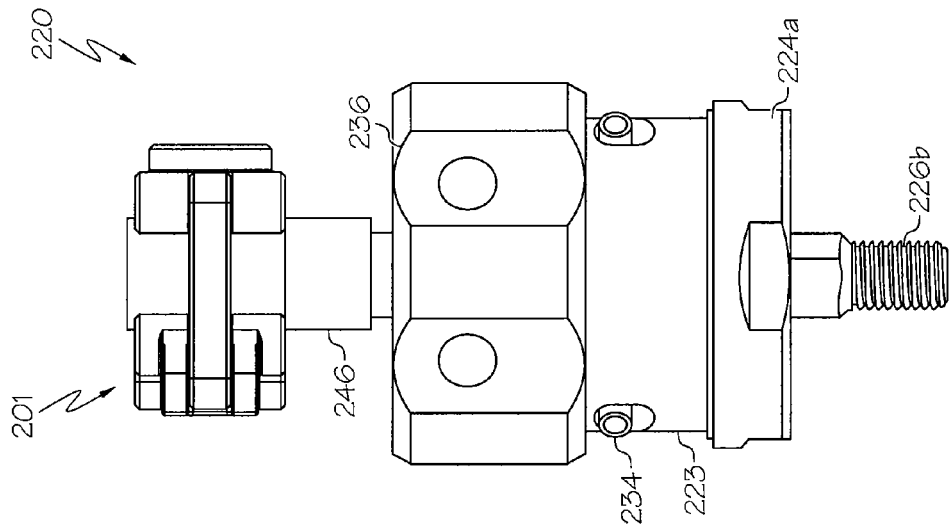
FIG. 16C is another side view of the external fixation polyaxial pivot housing of FIG. 16A.
Figure 16B:
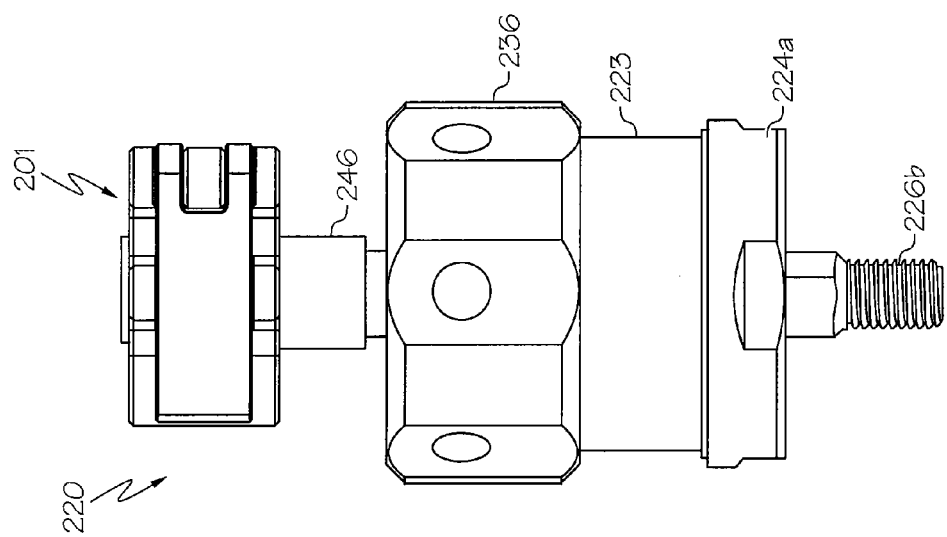
FIG. 16B is a side view of the external fixation polyaxial pivot housing of FIG. 16A.
Figure 16D:
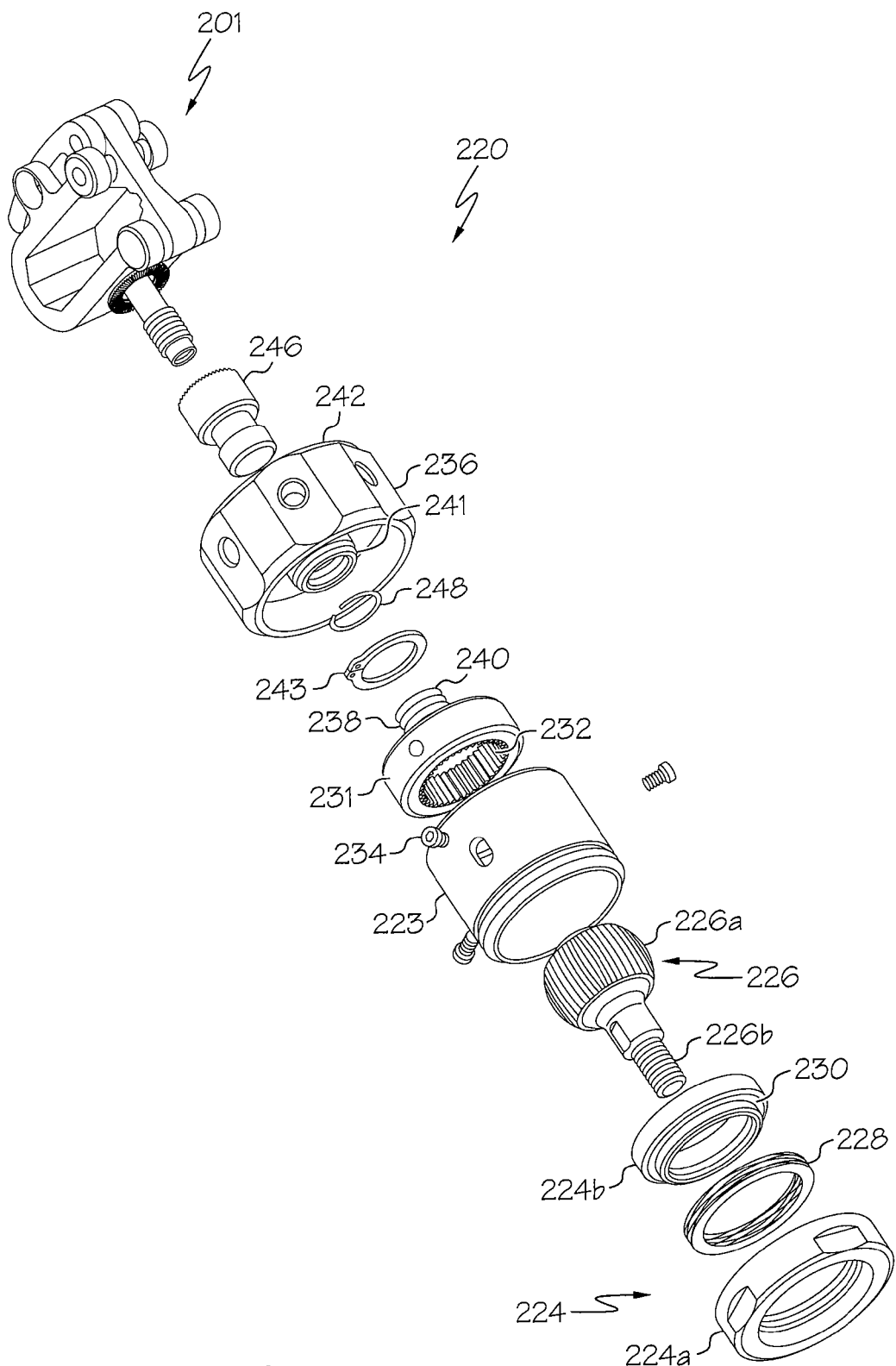
FIG. 16D is an exploded perspective view of the external fixation polyaxial pivot housing of FIG. 16A and associated with a clamping assembly in accordance with the teachings of the present disclosure.

When the pivot housing 160 is assembled, the outer collet housing 162 provides a compressive loading along with the locking nut 164 to thereby hold and center the spherical body 169 of the sphere/post assembly 166 therebetween. To accomplish this, the outer collet housing 162 includes a series of threads 163 that are configured to threadingly mesh with corresponding threads 165 of the locking nut 164. In accordance with certain alternative aspects of the present disclosure, and as specifically shown in FIG. 15, a pivot housing 161 may also include a separate compression collet 167 that is configured to fit inside of an inner periphery 171 of the outer collet housing 162 such that when the threads 175, 177 of the outer collect housing 162 and the locking nut 164 are engaged, the compression collet 167 compresses around the spherical body 169 to provisionally or definitively lock the pivot housing 160 relative to the fixation frame 100, 101, 103. In accordance with this aspect of the present disclosure, the outer collet housing 162 is configured to prevent the compression collet 167 from rotating and guides the compression collet to compress against the spherical body 169 during the locking process.

To provisionally lock the external fixation frame 100, 101, 103, the threaded compression collar or locking nut 164 presses against the outer collet housing 162 (and/or compression collet 167 if optionally used) to provide a friction fit. Specifically, the provisional lock is obtained when the locking nut 164 and outer collet housing 162 (and/or compression collet 167) are caused to provide a compressive force to the spherical body 169, thus preventing movement by soft-tissue forces. The friction fit and soft tissue tension allows the surgeon to provisionally lock the frame and make minor adjustments to the bone alignment. Once the surgeon is satisfied with the fixation of the bone fragments, the frame can then be definitively locked to maintain the bone fragments within the desired alignment.

To definitively lock the pivot housing 160, the threads 165 of the locking nut 164 are threadingly mated with the threads 163 of the outer collet housing 162, thereby compressing the sphere/post assembly 166 therebetween (or by threadingly mating threads 175 and 177 if the compression collet 167 is optionally used as shown with pivot housing 161). A removable nut socket or wrench 176 can also be removably attached to the outer periphery of the locking nut 164 and used to further tighten the threaded relationship between the outer collet housing 162 and the locking nut 164 if desired. To accomplish this, the outer periphery of the locking nut 164 may contain a series of ridges or notches 178 that are configured to matingly correspond to a series of ridges or notches 180 on the inner periphery of the removable nut wrench 176.

As those of skill in the art will understand herein, the removable nut wrench 176 can have an inner peripheral circumference that is slightly smaller than that of the outer peripheral circumference of the locking nut 164. In accordance with this embodiment, the removable nut wrench 176 is defined by a partially cylindrical knob body 179 having one or more hollowed out or concave portions or flutes 181 that are fabricated into its outer periphery to provide an improved gripping surface (i.e., the surface can have an ergonomic contour that fits the user's hand comfortably). The knob body 179 is further defined by two end portions or arms 183, 185 that are positioned substantially adjacent to one another, yet do not touch each other (i.e., they are separated by a gap 187). As the nut wrench 176 is mated with the locking nut 164, the arms 183, 185 are caused to separate (move away) from each other, thereby increasing the size of the gap 187. While those of skill in the art will understand and appreciate herein that forming a gap or a voided region within an otherwise solid object will impart some inherent elasticity to the object, in accordance with certain aspects of the present disclosure, the body 179 may further be formed of a material having elastic deformation properties to further enhance this quality as desired. By causing the removable nut wrench 176 to be elastically deformable, as the wrench 176 is fitted over the locking nut 164, the wrench will return to its original shape once positioned over the locking nut 164, thereby creating a snapping engagement thereto. After the nut wrench 176 is used to further tighten the locking nut 164, it can then be removed from the housing 160, 161 if desired so that the patient (to which the external fixation frame is installed) is unable to tamper with the frame.

Extending from the spherical body 169 is an attachment post 154 that is configured to connect (e.g., thread) the pivot housing 160, 161 to a frame connector or ratcheting strut 106 that bridges the proximal ring frame 102 to the distal ring frame 104. While the attachment post 154 and the spherical body 169 can be manufactured as a single component or unit, in accordance with certain aspects of the present disclosure, the attachment post 154 and the spherical body 169 may be fabricated independently of one another. For instance, the spherical body 169 may include a threaded aperture that is configured to receive a threaded portion of the attachment post 154. Moreover, the outer collet housing 162 and the compression collet 167 (if used) each may be manufactured from single pieces or multiple pieces interconnected if desired. As such, the present disclosure is not intended to be limited herein.

As shown in FIGS. 16A-16D, another illustrative design for a polyaxial pivot housing 220 in accordance with another aspect of the present disclosure is shown. In accordance with this embodiment, the housing 220 includes an outer sleeve 223 that is configured to receive a base assembly 224 and a serrated sphere/post assembly 226, the serrated sphere/post assembly 226 being comprised of a spherical ball portion 226A and a strut attachment post portion 226B. The base assembly 224 is composed of two separate base portions (i.e., a first base portion 224A and a second base portion 224B) that are separated from each other by a wave spring 228 (i.e., the first and second base portions 224A, 224B sandwich the wave spring 228 therebetween). Specifically, the wave spring 228 is configured to be housed within a ridge or shelf 230 of the second base portion 224B. When the housing is assembled, the first and second base portions 224A, 224B mate with each other (via the wave spring 228) and force the serrated sphere/post assembly 226 into the outer sleeve 223. The spherical ball portion 226A of the serrated sphere/post assembly 226 in turn interfaces with a serrated base assembly 231 that has an inner serrated periphery 232 that is configured to matingly receive the outer surface of the spherical ball portion 226A. When the housing 220 is assembled, anti-rotation screws 234 can be inserted into outer sleeve 223 to prevent the serrated base assembly 231 from rotating inside of the outer sleeve 223.

A locking nut portion 236 is in turn configured to be threaded to the serrated base assembly 231 by way of a threaded post 238 that extends from the serrated base assembly 231. In accordance with this aspect of the present disclosure, when the pivot housing 220 is assembled, the serrated base assembly 231 provides a compressive loading along with the locking nut portion 236 to thereby hold and center the serrated spherical ball portion 226A of the sphere/post assembly 226 therebetween. To accomplish this, the threaded post 238 includes a series of threads 240 that are configured to threadingly mesh with corresponding threads 241 within a bore hole 242 of the locking nut portion 236. A retaining ring 243 is held between the top surface of the serrated base assembly 231 and the bottom surface of the locking nut portion 236.

A clamping assembly platform 246 is in turn coupled to the locking nut's bore hole 242 on the side opposite the threaded portion 241. The clamping assembly platform 246 includes a threaded internal aperture (not shown) that is configured to receive a clamping assembly (such as assembly 108). To secure the clamping assembly platform 246 to the locking nut portion 236, a retaining ring 248 is utilized.

As mentioned previously, once the external fixation frame is attached to a patient via percutaneous bone pins, the surgeon will position the bone fragments via C-arm (X-ray) to align, stabilize and prevent additional neurovascular damage. The internal wave spring 228 and soft tissue tension experienced by the presently disclosed pivot housing 220 allows the surgeon to provisionally lock the frame and make minor adjustments to the bone alignment. Once the surgeon is satisfied with the fixation of the bone fragments, the frame may be definitively locked to maintain the bone fragment's alignment. To achieve the definitive lock, the locking nut portion 236 is rotated such that the internal thread moves the serrated base assembly 231 against the serrated surface of the serrated spherical ball portion 226A of the sphere/post assembly 226.

The attachment post portion 226B that extends from the serrated spherical ball is configured to function as an means to connect (e.g., thread) the pivot housing 220 to a frame connector or ratcheting strut 106 that bridges the proximal ring frame 102 to the distal ring frame 104.

Figure 17A:
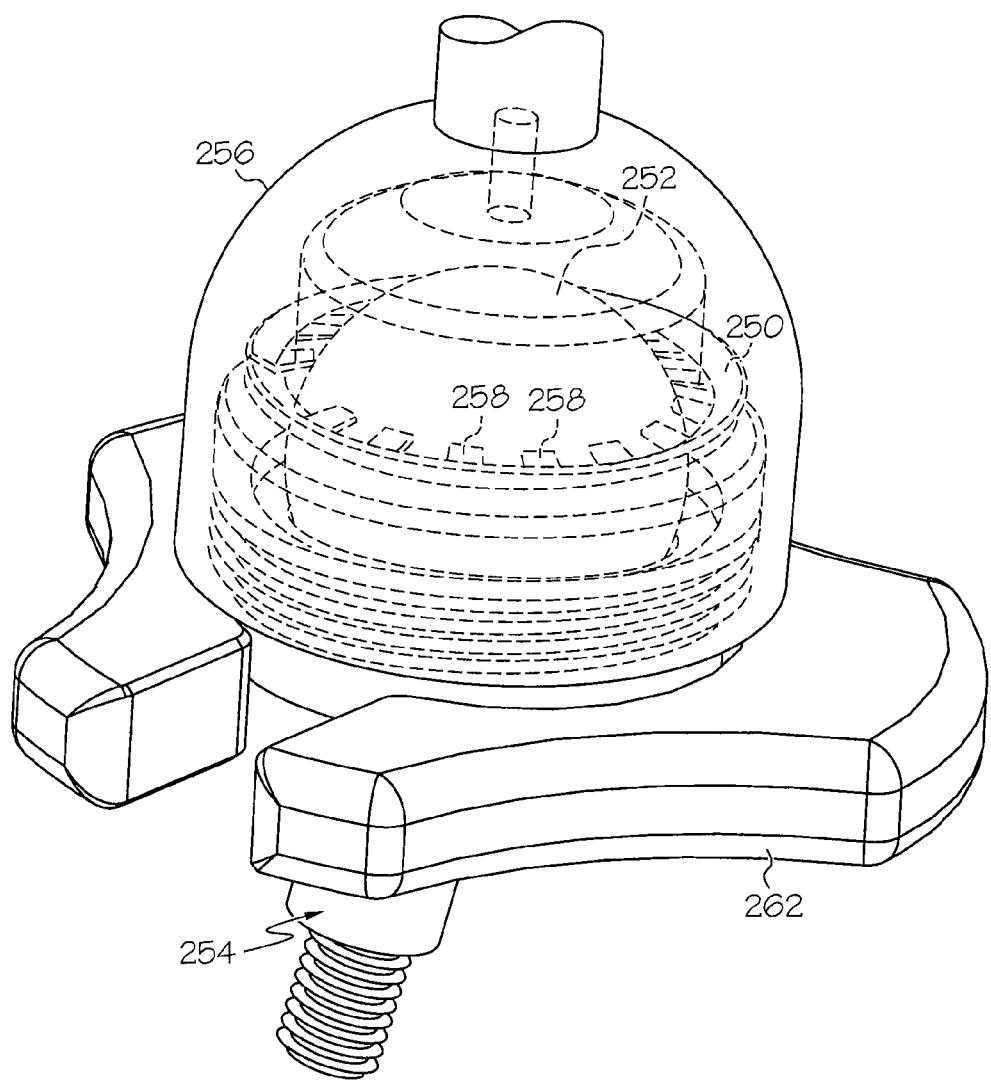
FIG. 17A is a perspective view of an external fixation polyaxial pivot housing in accordance with one illustrative embodiment of the present teachings and having internal locking rings shown in phantom.
Figure 17B:
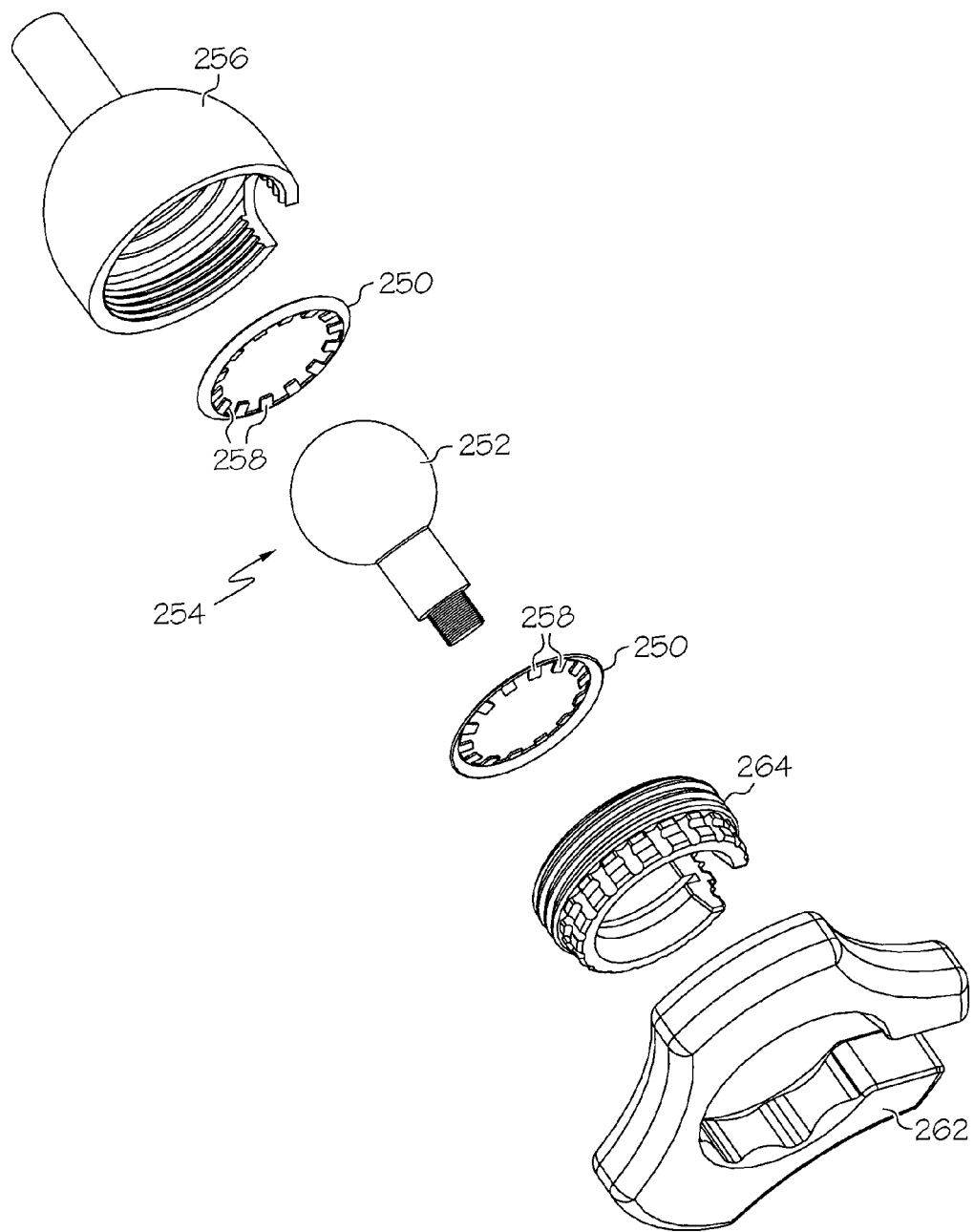
FIG. 17B is an exploded perspective view of the external fixation polyaxial pivot housing of FIG. 17A.
Figure 17C:
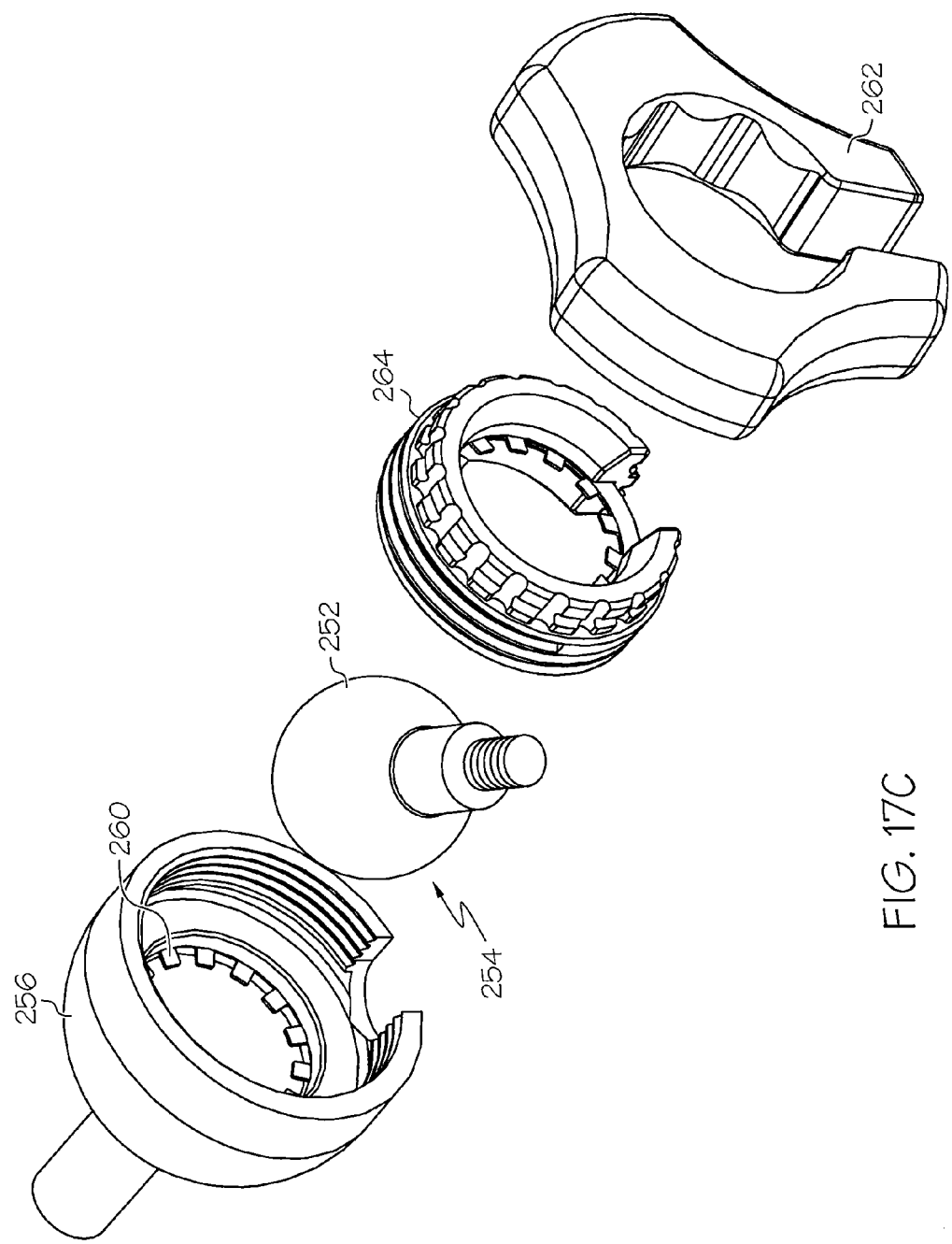
FIG. 17C is another exploded perspective view of an external fixation polyaxial pivot housing in accordance with the present teachings.

As those of skill in the art will understand and appreciate herein, various different means can be utilized for provisionally and definitively locking any of the poly polyaxial pivot housings (e.g., 120, 160, 161 and 220) disclosed within of the present application. For instance, as shown in FIGS. 17A-17C, one or more self-locking retaining rings 250 can be mated with a top and/or bottom surfaces of the spherical ball portion 252 of the sphere/post assembly 254. In accordance with this illustrative aspect of the present disclosure, the spherical ball portion 252 is able to rotate freely inside the housing 256 until an axial force drives the ball 252 into the socket. As this force is applied to the ball, the teeth 258 of the one or more retaining rings 250 are caused to dig into the ball, thereby preventing it from further rotation. While the use of a retaining ring or rings may be desirable to arrest movement of the ball 252 in accordance with certain aspects of the present disclosure, it should be understood and appreciated herein that in accordance with other embodiments, a series of teeth or ridges 260 can be fabricated into the inner periphery of the housing 256 to arrest movement of the ball in lieu of (or in addition to) a retaining ring (see FIG. 17C). Despite the means chosen to arrest movement of the ball 252 (e.g., retaining ring or fabricated ridges), to allow a threaded member (not shown) to apply additional compression to the ball 252 and thereby achieve a permanent or definitive lock, a removable wrench 262 can be connected to the compression collar 264 and tightened as explained above to compress the ball 252 within the housing 256.

Figure 18:
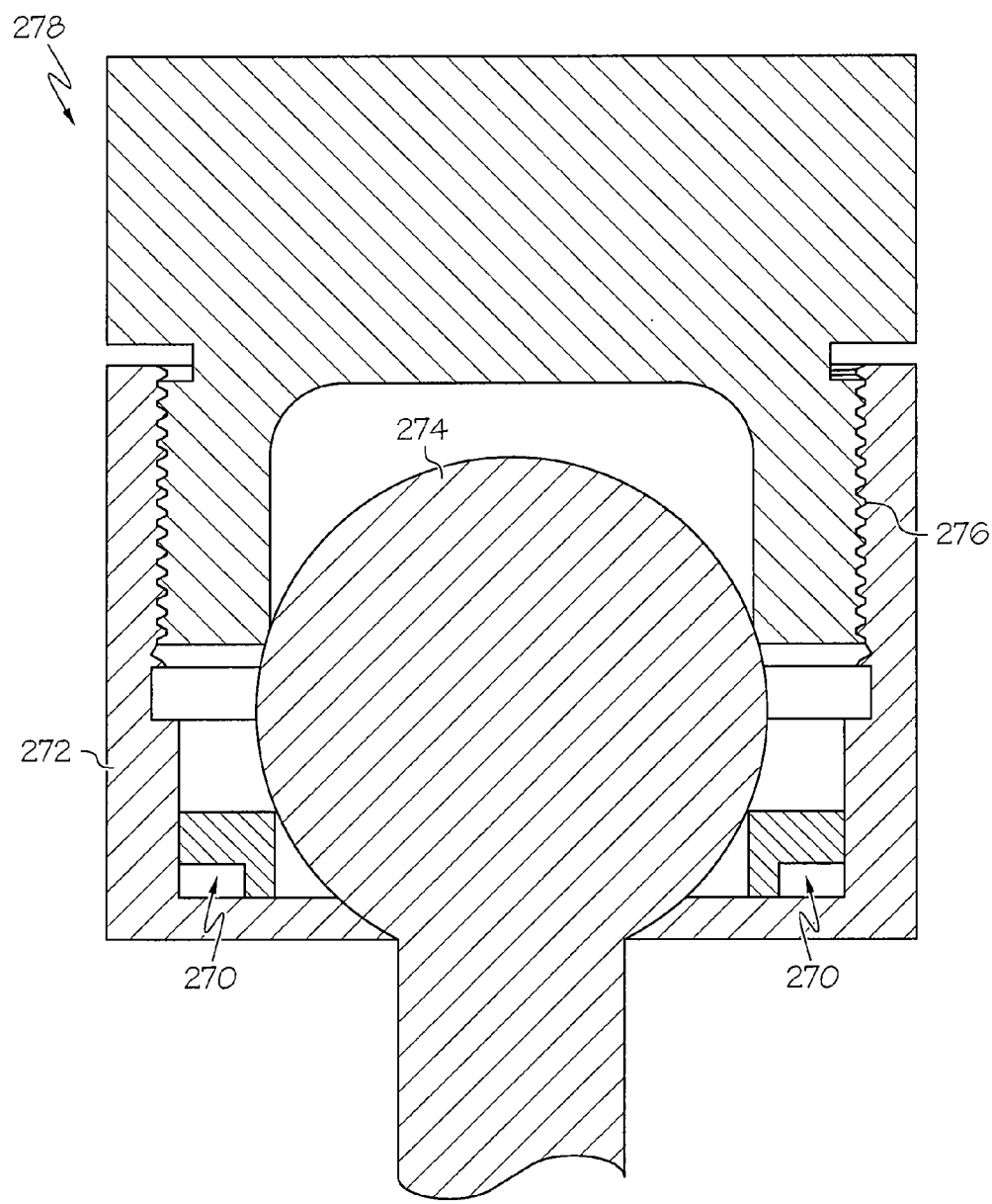
FIG. 18 is a cross-sectional view of an external fixation polyaxial pivot housing in accordance with another illustrative embodiment of the present teachings and having a wave spring locking assembly.

In accordance with yet another embodiment, and as is specifically shown in FIG. 18, a wave spring 270 can be inserted into the housing 272 such that it pinches the ball 274 on each side of its equator to achieve the provisional lock. More particularly, as tension is applied to the frame via a strut, the ball 274 compresses the wave spring 270 so that there is no longer contact with the edge of the socket. Permanent (definitive) fixation can be achieved by tightening the outer threads 276 of the housing 278 until the ball 274 is tightly fixed.

Figure 19B:
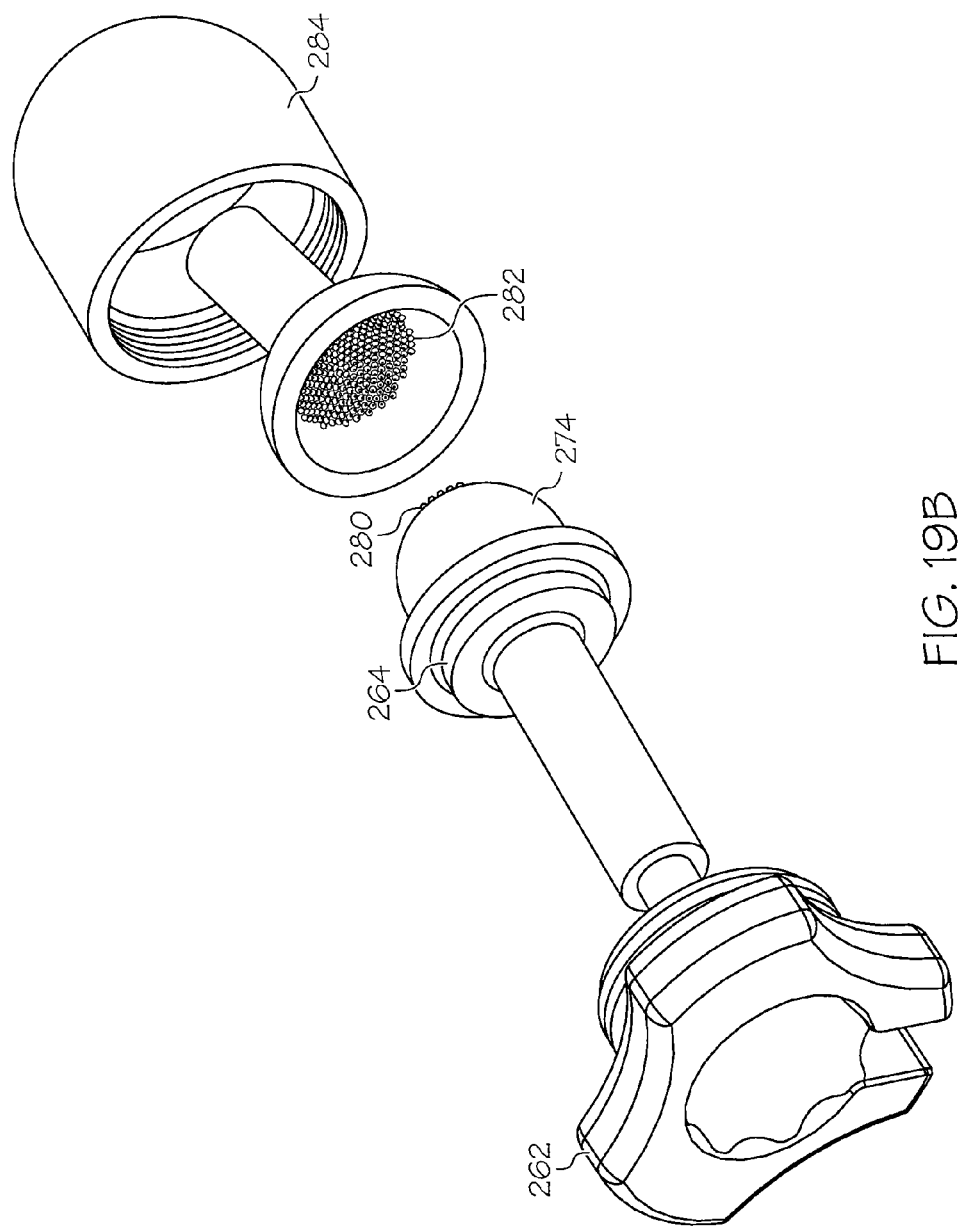
FIG. 19B is another exploded perspective view of the external fixation polyaxial pivot housing of FIG. 19A.

As shown in FIGS. 19A and 19B, instead of pinching the ball 274 with a wave spring, those of skill in the art will understand and appreciate that it is also possible to include protrusions 280 from the ball that are configured to matably engage corresponding recessed portions 282 of the socket 284 to prevent rotation. While not shown specifically herein, it is also possible to prevent rotation by including sharp spikes on the socket that are designed to cut into a semi-soft ball.

In accordance with certain fixation procedures of the present disclosure, it may be desirable to position or stack one or more clamping assemblies on top of each other. While it may be desirable to allow these stacked components to freely articulate with respect to one another in certain situations, in accordance with other aspects of the present teachings, it may be desirable to establish a fixed relationship between these parts. While there are numerous ways to establish a fixed relationship between any of the disclosed clamping assemblies discussed herein, in accordance with certain aspects of the present teachings, the clamping assemblies may have one or more serrated surfaces (see serrated surface 222 of FIG. 3C, for instance) that are configured to structurally mesh with one another when desired such that rotational independence of the stacked assemblies is not possible.

Figure 20:
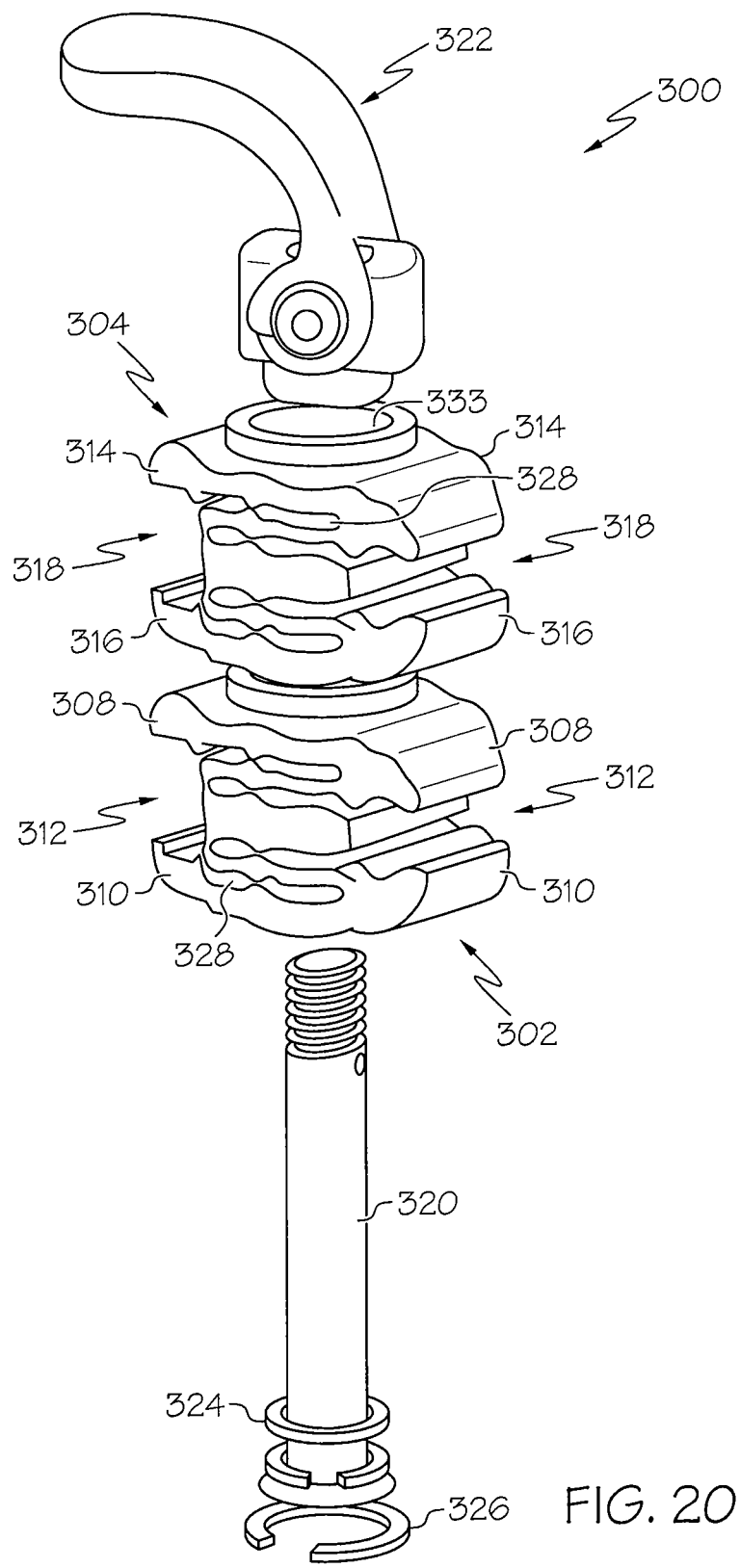
FIG. 20 is an illustrative external fixation stacked rod/pin clamping assembly in accordance with the teachings of the present disclosure.

An illustrative embodiment of a stacked or combination rod/pin clamping assembly 300 in accordance with the present disclosure is shown with particular reference to FIG. 20. The clamping assembly 300 in accordance with this aspect of the present disclosure is operative for connecting various elongated members having a cylindrical shape, such as, for instance rods and pins. The clamp assembly 300 is illustrated to include a first or lower clamp member 302 and a second or upper clamp member 304. As used herein, terms of orientation, including but not limited to such as "upper" and "lower" are included merely for purposes of referencing the drawings and are not to be considered limiting in nature.

Explaining further, it will be readily apparent to those skilled in the art that any of the disclosed clamping assemblies (including clamp assembly 300, for instance) are contemplated to be equally operative in any conceivable orientations with respect to one another, and as such, the various illustrative orientations shown within the drawings are not intended to serve as an all-inclusive list of the available orientations to which these components can be used in conjunction with the presently disclosed external fixation frame systems.

The first clamp member 302 includes a pair of upper jaw portions 308 and a pair of lower jaw portions 310 which cooperate to define respective openings 312 for receiving cylindrical rods and/or pins that are needed to assemble the external fixation system. Similarly, the second clamp member 304 includes a pair of upper jaw portions 314 and a pair of lower jaw portions 316 which cooperate to define respective openings 318 for receiving cylindrical rods and/or pins inserted therein as well.

Figure 21:
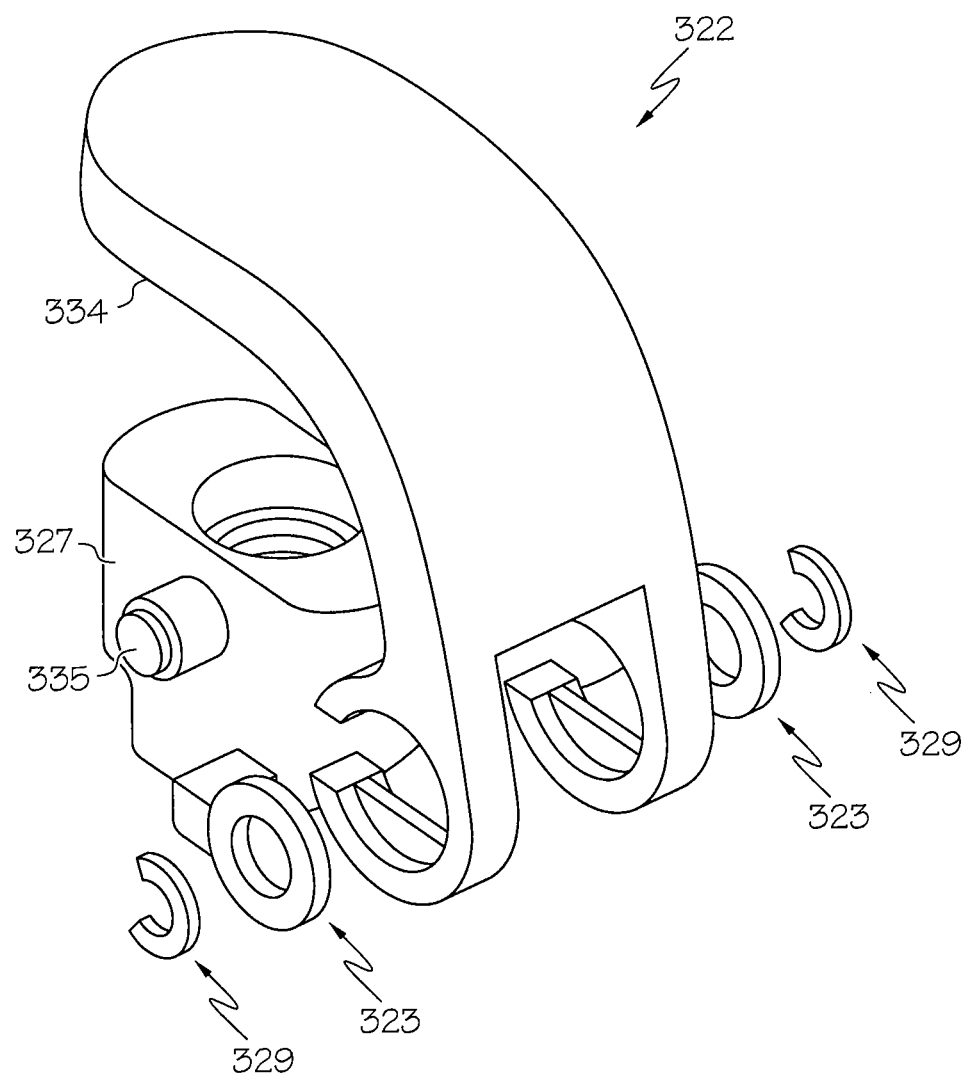
FIG. 21 is an illustrative cam nut locking assembly in accordance with the teachings of the present disclosure.

In accordance with this illustrative embodiment, the first and second clamp members 302, 304 are connected to one another by a threaded clamp bolt 320 that passes through a common aperture 333 of the clamp members in such a manner that it compresses the first and second clamp members 302, 304 against one another, as well as the rods and/or pins held therein. The threaded clamp bolt 320 is configured to thread into a cam locking nut assembly 322 that is housed within an opening on the top surface of the second clamp member 304. As shown in FIG. 21, the cam locking nut assembly 322 includes a body 327 that interfaces with the threaded clamp bolt 320 to provide provisional locking, as well as a pivot arm 334 which actuates the definitive lock with movement of a pair of offset cam rings 323. The offset cam rings 323 in turn transmit motion of the pivot arm 334 around pivot posts 335 to a definitive locking force against the first and second clamp members 302, 304 as they are centered by the threaded clamp bolt 320. The offset cam rings 323 and the cam lock pivot arm 334 are held on the pivot posts 335 and into the cam locking nut body 327 by way of a pair of external locking rings 329.

Once the various rods and/or pins are positioned within the first and second clamp members 302, 304, the clamps may be provisionally locked by turning (rotating) the cam locking nut assembly 322 around the threaded clamp bolt rod 320 until the assembly 300 is finger tight. As the threaded clamp bolt 320 is tightened, an O-ring 324 acts as a spring, while an internal snap ring 326 holds the clamp bolt 320 and O-ring 324 inside of the lower section of the first clamp member 302. Once the surgeon is satisfied with the position and fixation of the bone fragments, the assembly 300 can be definitively locked by rotating the pivot arm 334 of the cam locking nut assembly 322 in a direction that moves the offset cam rings 323 into contact with the opposing items, thereby creating an additional offset distance and additional locking load.

In accordance with certain aspects of the present teachings, the first and second clamp members 302, 304 may have a series of axial slots 328 formed into their respective bodies. According to certain aspects of this embodiment, the axial slots may be positioned adjacent to and/or at least partially terminating into the openings 312, 318 to thereby allow the jaw portions of the clamp members to be elastically displaced in response to a cylindrical rod, pin or the like being introduced therein. In other words, as a rod, pin, etc. is laterally introduced into one of the openings 312, 318, the upper and lower jaw portions of that clamping member are urged apart from one another. Once the cylindrical object is fully seated within the upper and lower jaw portions of the clamping member, a counter-force snappingly retains the object temporarily in place, particularly as the upper and lower jaw portions return to their original position prior to being displaced. As those of skill in the art will understand and appreciate herein, by fabricating such axial slots 328 into the clamping assembly, the elastic deformation properties associated with such a design inherently allows the upper and lower jaw portions to function much like a leaf spring, and as a result, cylindrical items placed therein can be snappingly retained within the defined opening.

To provide means for arresting rotational movement of the first clamp member 302 relative to the second clamp member 304 about a longitudinal axis of the clamp bolt 320, the first and second clamp members 302 and 304 may be formed to include cooperating serrations. As shown by reference numeral 222 in FIG. 3C for instance, an upper surface of the first clamp member 302 can similarly include a serrated portion having a plurality of serrations radially extending from a common aperture. The serrated portion can be adapted to engage a substantially identical serrated portion provided on an adjacent lower surface of the second clamp member 304. When the clamp bolt 320 compresses the first and second clamp member 302, 304 against each other as the cam locking nut assembly 322 is initially tightened, the serrated portions of the first and second clamp members 302 and 304 are drawn together to prevent relative movement therebetween.

Figure 22:
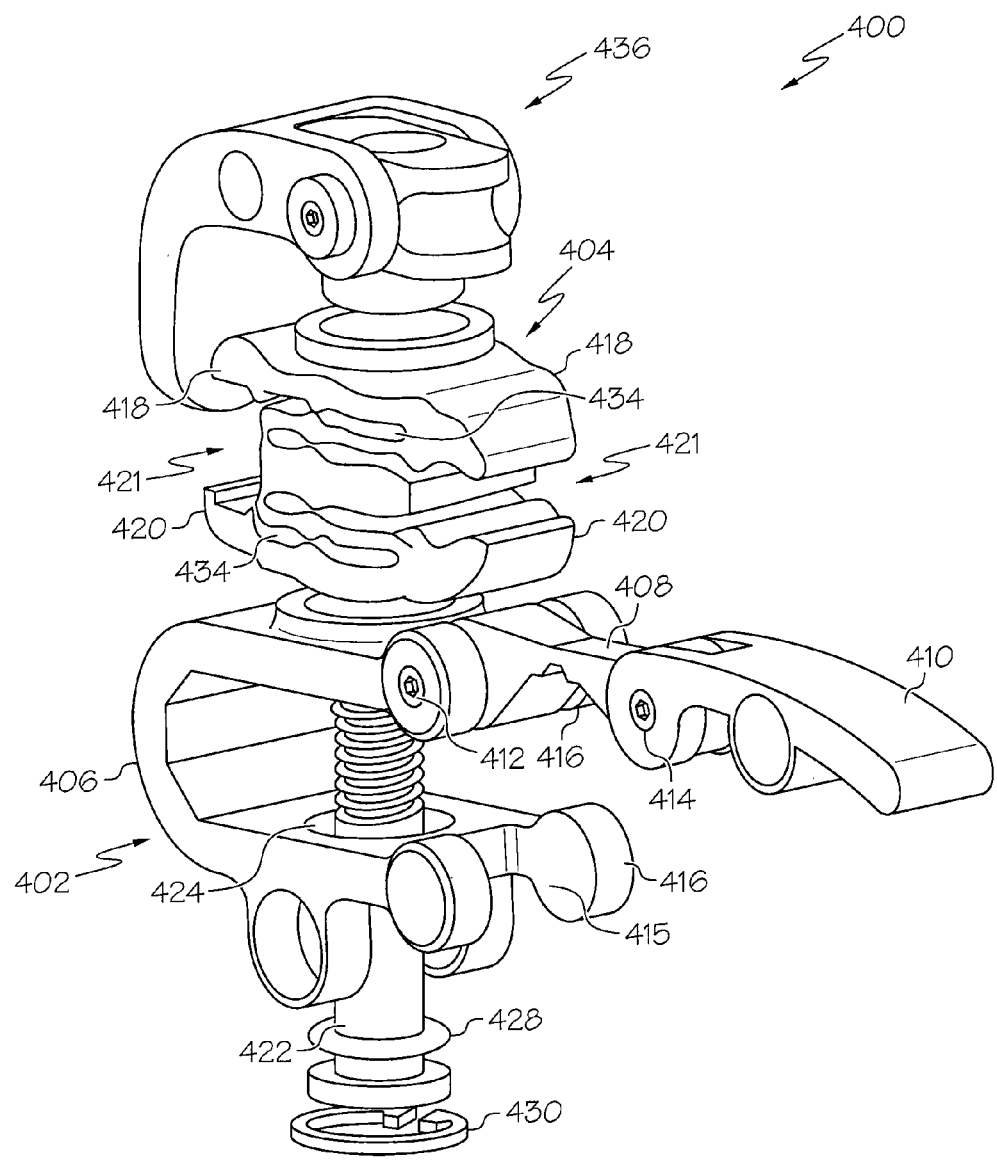
FIG. 22 is an illustrative frame to rod/pin external fixation clamping assembly in accordance with the teachings of the present disclosure.

Moving now to FIG. 22, a universal ring frame to rod/pin clamp assembly 400 in accordance with another teaching of the present disclosure is depicted. The clamp assembly 400 is illustrated to include a first or lower clamp member 402 and a second or upper clamp member 404. The first clamp member 402 includes a clamp body 406, a locking arm 408, a cam arm 410, a locking arm pivot pin 412 and a cam arm pivot pin 414. The first clamp member 402 is configured to be snapped onto a ring frame 102, 104 or a rod by positioning the clamp body 406 substantially perpendicular to the ring leg or rod and applying pressure to force end jaws 416 open and over the ring or rod. Alternatively, the first clamp member 402 can be snapped onto the ring frame or rod by positioning the clamp body 406 at the end of a ring leg or rod and applying pressure to slide the body onto the ring or rod.

The second clamp member 404 includes a pair of upper jaw portions 418 and a pair of lower jaw portions 420 which cooperate to define openings 421 for receiving cylindrical rods and/or pins that are needed to assemble the external fixation system.

Figure 23:
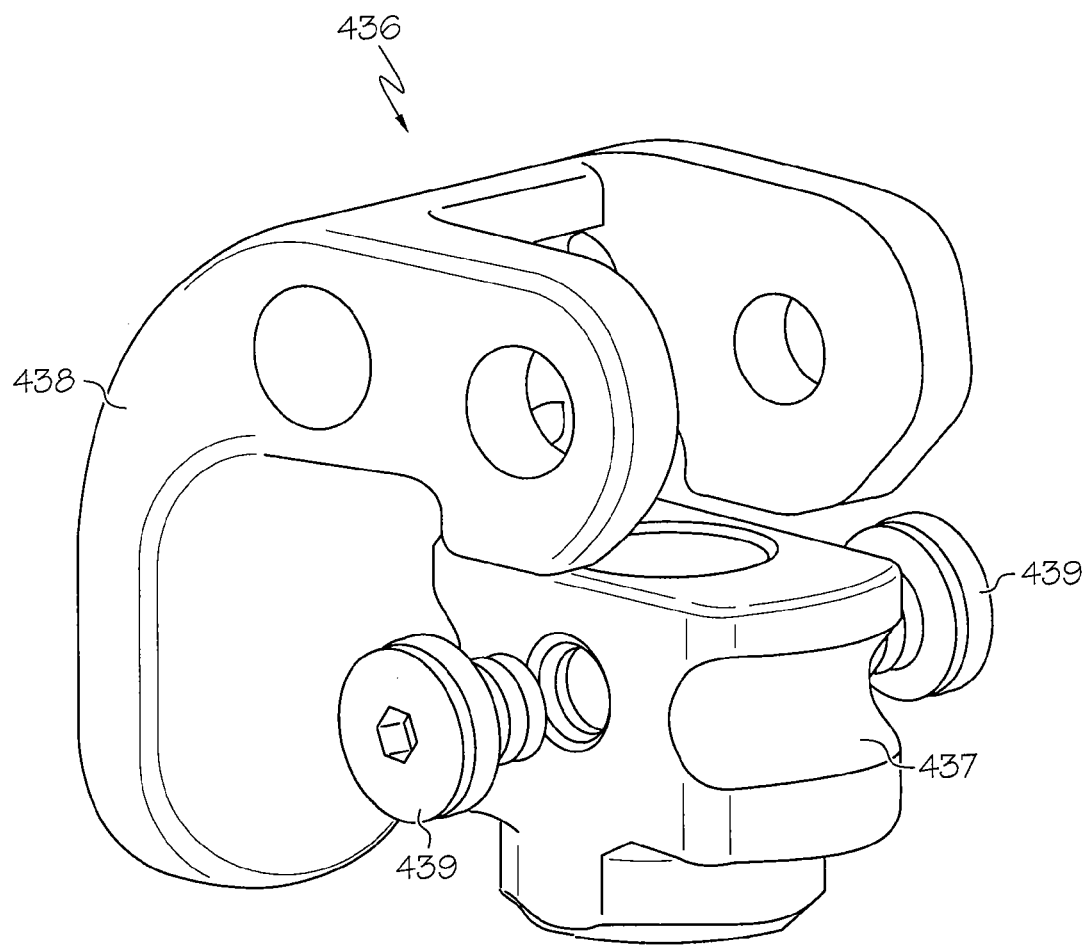
FIG. 23 is an illustrative cam nut locking assembly in accordance with the teachings of the present disclosure.

In accordance with this illustrative embodiment, the first and second clamp members 402, 404 are connected to one another by a threaded clamp bolt 422 that passes through a common aperture 424 of the clamp members in such a manner that it compresses the first and second clamp members 402, 404 against one another, as well as the rings, rods and/or pins held therein. The threaded clamp bolt 422 is configured to thread into a cam locking nut assembly 436. As shown in FIG. 23, the cam locking nut assembly 436 includes a body 437 that interfaces with the threaded clamp bolt 422 to provide provisional locking, as well as an off-set cam pivot arm 438 which pivots around a pair of low profile or bottom head cap screws 439.

Once the various rods, pins and/or rings are positioned within the first and second clamp members 402, 404, the clamps may be provisionally locked by turning the cam locking nut assembly 436 around the threaded clamp bolt rod 422 until the assembly 400 is finger tight. As the threaded clamp bolt 422 is tightened, an O-ring 428 acts as a spring, while an internal snap ring 430 holds the clamp bolt 422 and O-ring 428 inside of the lower section of the first clamp member 402. Moreover, the locking arm 408 of the first clamp member 402 is rotated (via the locking arm pivot pin 412) towards and into a cam arm pocket 415 to further create a provisional lock with respect to the first clamp member.

Once the surgeon is satisfied with the position and fixation of the bone fragments, the assembly can be definitively locked by rotating the pivot arm 438 of the cam locking nut assembly 436 to create an additional offset distance and additional locking load, as well as by rotating the cam arm 410 of the first clamp member 402 towards the clamp body 406 via the cam arm pivot pin 414 located at the center of the cam arm 410 until it touches the clamp body 406.

In accordance with certain aspects of the present teachings, the second clamp member 404 may have a series of axial slots 434 formed into its body. According to certain aspects of this embodiment, the axial slots may be positioned adjacent to and/or at least partially terminating into the openings 421 to thereby allow the jaw portions 418, 420 to be elastically displaced in response to a cylindrical rod, pin or the like being introduced therein. In other words, as a rod, pin, etc. is laterally introduced into one of the openings 421, the upper and lower jaw portions defining that opening are urged apart from one another. Once the cylindrical object is fully seated within the upper and lower jaw portions, a counter-force snappingly retains the object temporarily in place, particularly as the upper and lower jaw portions return to their original position prior to being displaced. As those of skill in the art will understand and appreciate herein, by fabricating such axial slots 434 into the clamp member, the elastic deformation properties associated with such a design inherently allows the upper and lower jaw portions to function much like a leaf spring, and as a result, cylindrical items placed therein can be snappingly retained within the defined opening.

To provide means for arresting rotational movement of the first clamp member 402 relative to the second clamp member 404 about a longitudinal axis of the clamp bolt 422, the first and second clamp members 402 and 404 may be formed to include cooperating serrations as described above with respect to assembly 201.

Figure 24:
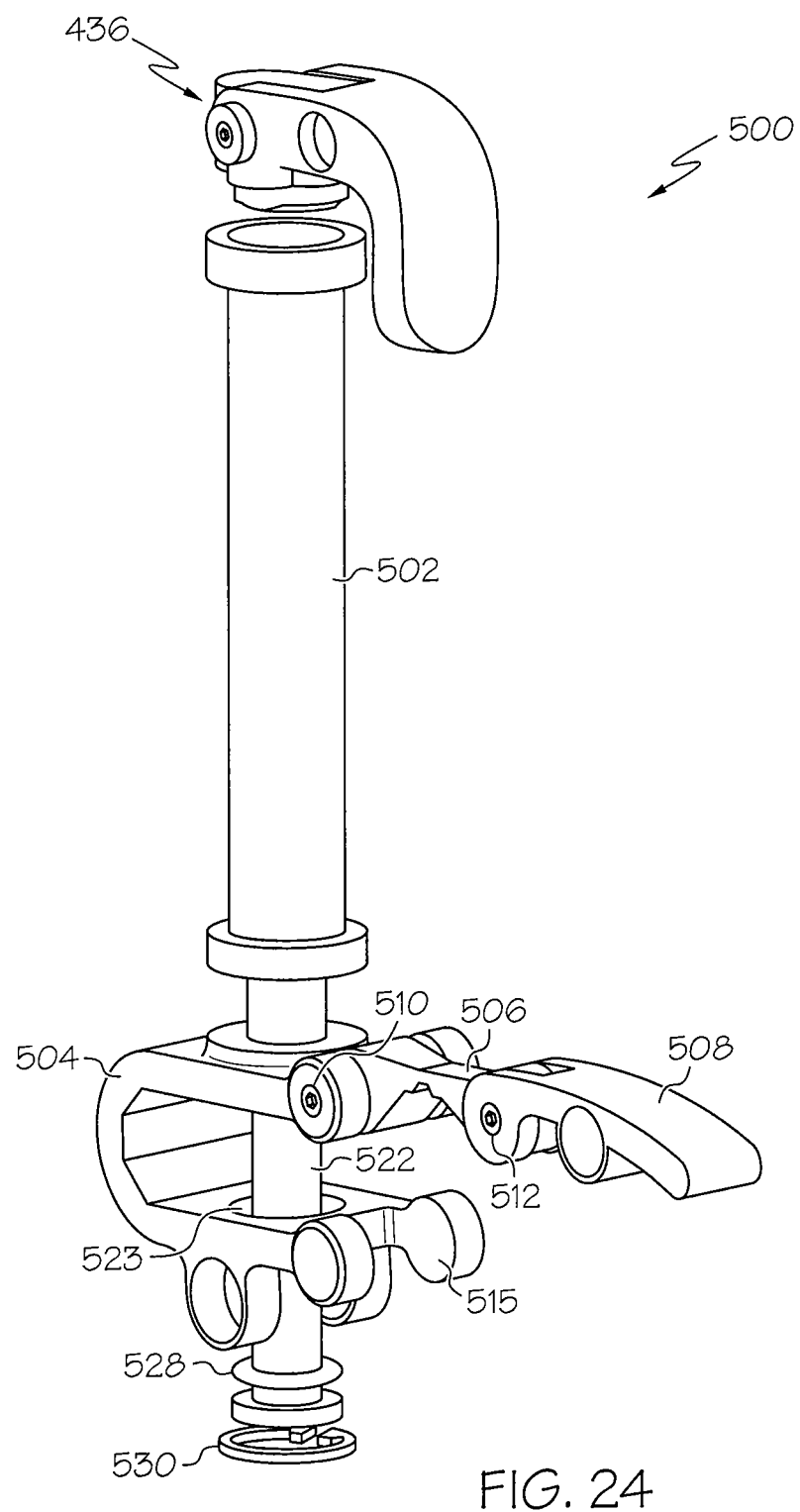
FIG. 24 is an illustrative ring-to-post external fixation clamping assembly in accordance with the teachings of the present disclosure.

Referring to FIG. 24, a universal ring-to-post clamp assembly 500 is provided. In accordance with this embodiment, the assembly 500 comprises a post body 502 that interfaces with the ring clamp body 504. More particularly, the clamping assembly 500 includes a clamp body 504, a locking arm 506, a cam arm 508, a locking arm pivot pin 510, a cam arm pivot pin 512, and a post body 502 that interfaces with the clamp body 504.

In accordance with this illustrative embodiment, the universal post body 502 and the ring clamp body 504 are connected to one another by a threaded clamp bolt 522 that passes through a common aperture 523 of the bodies 502, 504 in such a manner that it compresses the bodies against one another, as well as the ring held therein. The threaded clamp bolt 522 is configured to thread into a cam locking nut assembly 436 that is housed within an opening on the top surface of the universal post body 502.

Once the ring frame is positioned within the ring clamp body 504, the clamp may be provisionally locked by turning the cam locking nut assembly 436 around the threaded clamp bolt rod 522 until the assembly 500 is finger tight. As the threaded clamp bolt 522 is tightened, an O-ring 528 acts as a spring, while an internal snap ring 530 holds the clamp bolt 522 and O-ring 528 inside of the lower section of the clamp body 504. Moreover, the locking arm 506 of the ring clamp body 502 is rotated (via the locking arm pivot pin 510) towards and into a cam arm pocket 515 to further create a provisional lock with respect to the first clamp member.

Once the surgeon is satisfied with the position and fixation of the bone fragments, the assembly can be definitively locked by rotating the pivot arm 438 of the cam locking nut assembly 436 to create an additional offset distance and locking load, as well as by rotating the cam arm 508 towards the ring clamp body 502 via the cam arm pivot pin 512 located at the center of the cam arm 508 until it touches the clamp body 502.

To provide means for arresting rotational movement of the first and second bodies, 502, 504 relative to one another about a longitudinal axis of the clamp bolt 522, the first and second bodies 502, 504 may be formed to include cooperating serrations as described above with respect to assembly 201.

Figure 25:
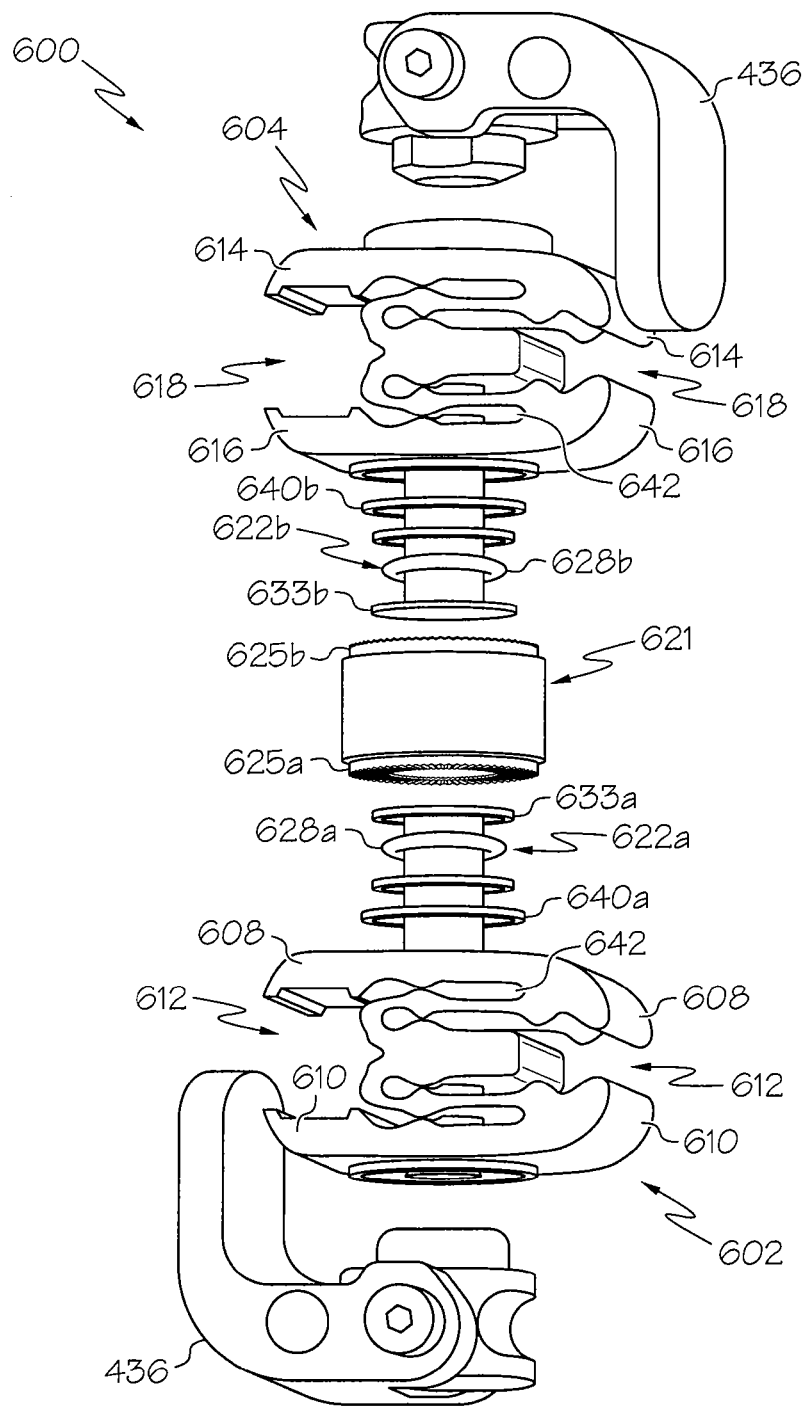
FIG. 25 is another illustrative rod/pin clamp external fixation clamping assembly in accordance with the teachings of the present disclosure.

Referring to FIG. 25, another illustrative clamping assembly 600 in accordance with the present disclosure is illustrated. This illustrative assembly is similar to clamping assembly 300 illustrated in FIG. 20 yet includes two cam locking nut assemblies in conjunction with a centralized serrated washer component. In accordance with this aspect of the present disclosure, the clamping assembly 600 is operative for connecting various elongated members having a cylindrical shape, such as, for instance rods and pins. The clamp assembly 600 is illustrated to include a first or lower clamp member 602 and a second or upper clamp member 604. The first clamp member 602 includes a pair of upper jaw portions 608 and a pair of lower jaw portions 610 which cooperate to define respective openings 612 for receiving cylindrical rods and/or pins that are needed to assemble the external fixation system. Similarly, the second clamp member 604 includes a pair of upper jaw portions 614 and a pair of lower jaw portions 616 which cooperate to define respective openings 618 for receiving cylindrical rods and/or pins inserted therein as well.

In accordance with this illustrative embodiment, the first and second clamp members 602, 604 are spaced apart or separated from one another by a serrated washer assembly 621 that holds and contains first and second threaded clamp bolts 622A, 622B that are each configured to independently pass through an aperture formed within one of the respective clamp members 602, 604. In particular, the serrated washer assembly 621 has a first serrated surface 625A and an opposing second serrated surface 625B, the first and second serrated surfaces being substantially parallel to one another. The first and second serrated surfaces 625A, 625B each include a substantially circular recessed portion or cavity (not particularly shown) that is configured to receive an O-ring 633A, 633B associated with the respective first and second threaded clamp bolts 622A, 622B. The O-rings 633A, 633B are in turn compressed against the threaded clamp bolts 622A, 622B by washers 628A, 628B.

The first and second threaded clamp bolts 622A, 622B are each configured to thread into a cam locking nut assembly 436 that is respectively housed within an opening of the first and second clamp members 602, 604. As shown in FIG. 23, the cam locking nut assemblies 436 include a body 437 that interfaces with the threaded clamp bolts 622A, 622B to provide provisional locking, as well as a locking pivot arm 438 which pivots around a low profile or button head cap screws 439 and has an off-set cam that adds distance for tightening the threaded clamp bolts 622A, 622B.

Once the various rods and/or pins are positioned within the first and second clamp members 602, 604, the clamps may be provisionally locked by turning the respective cam locking nut assemblies 436 around the threaded clamp bolts 622A, 622B until the assembly 600 is finger tight. As the threaded clamp bolts 622A, 622B are tightened, the O-rings 633A, 633B act as springs, while internal snap rings 640a, 640b hold the clamp bolts 622A, 622B, O-rings 633A, 633B and washers 628a, 628b inside of the serrated washer assembly 621. Once the surgeon is satisfied with the position and fixation of the bone fragments, the assembly 600 can be definitively locked by rotating the locking pivot arms 638 of the cam locking nut assemblies 436 in a direction that moves the offset cam rings into contact with the opposing item, thereby creating an additional offset distance and additional locking load.

In accordance with certain aspects of the present teachings, the first and second clamp members 602, 604 may have a series of axial slots 642 formed into their respective bodies. According to certain aspects of this embodiment, the axial slots may be positioned adjacent to and/or at least partially terminating into the openings 612, 618 to thereby allow the jaw portions of the clamp members to be elastically displaced in response to a cylindrical rod, pin or the like being introduced therein. In other words, as a rod, pin, etc. is laterally introduced into one of the openings 612, 618, the upper and lower jaw portions of that clamping member are urged apart from one another. Once the cylindrical object is fully seated within the upper and lower jaw portions of the clamping member, a counter-force snappingly retains the object temporarily in place, particularly as the upper and lower jaw portions return to their original position prior to being displaced. As those of skill in the art will understand and appreciate herein, by fabricating such axial slots 642 into the clamping assembly, the elastic deformation properties associated with such a design inherently allows the upper and lower jaw portions to function much like a leaf spring, and as a result, cylindrical items placed therein can be snappingly retained within the defined opening.

To provide means for arresting rotational movement of the first clamp member 602 relative to the second clamp member 604 about a longitudinal axis of the clamp bolts 622A, 622B, the first and second clamp members 602 and 604 may be formed to include cooperating serrated portions or surfaces that are configured to interact with the serrated surfaces 625A, 625B of the serrated washer assembly 621. The serrated portions of the first and second clamp members 602, 604 can be adapted to engage the serrated surfaces 625A, 625B of the serrated washer assembly 621 such that when the clamp bolts 622A, 622B compress the first and second clamp member 602, 604 against the serrated washer assembly 621 as the cam locking nut assemblies 636A, 636B are initially tightened, the serrated portions of the first and second clamp members 602 and 604 are drawn against the serrated surfaces 625A, 625B of the washer assembly such that relative movement between the first and second clamp members is prevented.

Figure 26:
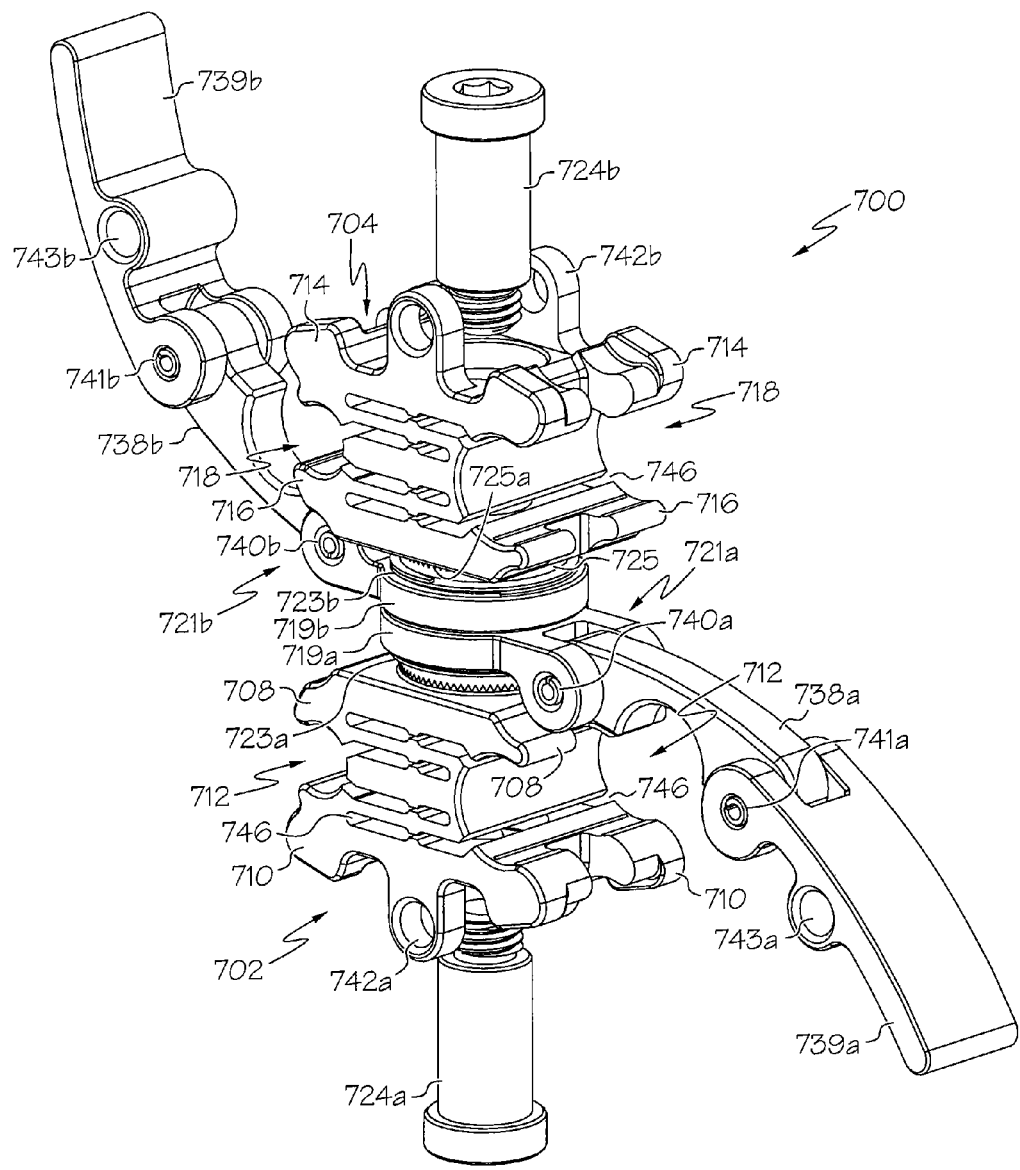
FIG. 26 is another illustrative rod/pin external fixation clamping assembly in accordance with the teachings of the present disclosure.

Referring to FIG. 26, an illustrative universal rod/pin clamping assembly 700 in accordance with the present disclosure is illustrated. The clamping assembly 700 is illustrated to include a first or lower clamp member 702 and a second or upper clamp member 704. The first clamp member 702 includes a pair of upper jaw portions 708 and a pair of lower jaw portions 710 which cooperate to define respective openings 712 for receiving cylindrical rods and/or pins that are needed to assemble the external fixation system. Similarly, the second clamp member 704 includes a pair of upper jaw portions 714 and a pair of lower jaw portions 716 which cooperate to define respective openings 718 for receiving cylindrical rods and/or pins inserted therein as well.

In accordance with this illustrative embodiment, the first and second clamp members 702, 704 are coupled to one another by a pair of locking assemblies 721A, 721B that are each independently configured to pivot with respect to one another, as well as with respect to the clamp members 702, 704. In accordance with this aspect of the present disclosure, the bottom surface of a second pivot body 719B of the second locking assembly 721B is configured to rest upon the top surface of a first pivot body 719A of the first locking assembly 721A. Both the first and second pivot bodies 719A, 719B each have a through-hole (not shown) such that when they are stacked on top of each other, a common through-hole is created. Within this common through-hole is housed a universal serrated washer 725. The universal serrated washer 725 has a pair of opposing serrated surfaces 725A (only one surface shown), as well as a pair of retaining ring grooves (not shown). When assembled, a pair of retaining rings 723A, 723B is inserted within the grooves and serve as a means for preventing the first and second pivot bodies 719A, 719B from disengaging from one another.

The first and second clamp members 702, 704 are coupled to first and second threaded clamp bolts 724A, 724B that are each configured to independently pass through apertures which are formed in the respective clamp members 702, 704. The first and second threaded clamp bolts 724A, 724B are each configured to thread into a threaded aperture (not shown) of the serrated washer 725.

Once the various rods and/or pins are positioned within the first and second clamp members 702, 704, the clamps may be provisionally and independently locked by rotating their respective locking pivot arm 738A, 738B (via the locking arm pivot pins 740A, 740B) towards and into cam arm pockets. Once the surgeon is satisfied with the position and fixation of the bone fragments, the frame or fixator can be definitively locked without the use of additional tools or equipment. To achieve the definitive lock, the cam arms 739A, 739B are rotated towards the clamp members 702, 704 via the cam arm pivot pins 741A, 741B located at the center of the respective cam arms 739A, 739B until it touches the clamp member.

Once the cam arms 739A, 739B are positioned within the clamp members 702, 704 during a definitive locking process, in accordance with certain aspects of the present disclosure, the cam arms 739A, 739B can be further locked into place by utilizing a locking pin (not shown) that is configured to be inserted through apertures 743A, 743B of the cam arms 739A, 739B. According to this embodiment, the clamp members 702, 704 each have a pair of upwardly projecting tabs 742A, 742B, each having a through-hole formed therein. When the cam arms 739A, 739B are positioned within the clamp members 702, 704, the through-holes align with apertures 743A, 743B formed into the cam arms 739A, 739B such that a common through-hole is created. The locking pin can then be inserted through this common through-hole, thereby preventing the cam arms 739A, 739B from being individually lifted away from the clamp members 702, 704 until the locking pin is first removed.

To provide means for arresting rotational movement of the first clamp member 702 relative to the second clamp member 704 about a longitudinal axis of the clamp bolts 724A, 724B, the first and second clamp members 702 and 704 may be formed to include cooperating serrated portions or surfaces that are configured to interact with serrated surface 725A of the serrated washer assembly 725. The serrated portions of the first and second clamp members 702, 704 can be adapted to engage the serrated surfaces of the serrated washer 725 such that when the clamp bolts 724A, 724B compress the first and second clamp member 702, 704, the serrated portions of the first and second clamp members 702 and 704 are drawn against the serrated surface of the serrated washer 725 such that relative movement between the first and second clamp members is prevented.

In accordance with certain aspects of the present teachings, the first and second clamp members 702, 704 may have a series of axial slots 746 formed into their respective bodies. According to certain aspects of this embodiment, the axial slots may be positioned adjacent to and/or at least partially terminating into the openings 712, 718 to thereby allow the jaw portions of the clamp members to be elastically displaced in response to a cylindrical rod, pin or the like being introduced therein. In other words, as a rod, pin, etc. is laterally introduced into one of the openings 712, 718, the upper and lower jaw portions of that clamping member are urged apart from one another. Once the cylindrical object is fully seated within the upper and lower jaw portions of the clamping member, a counter-force snappingly retains the object temporarily in place, particularly as the upper and lower jaw portions return to their original position prior to being displaced. As those of skill in the art will understand and appreciate herein, by fabricating such axial slots 746 into the clamping assembly, the elastic deformation properties associated with such a design inherently allows the upper and lower jaw portions to function much like a leaf spring, and as a result, cylindrical items placed therein can be snappingly retained within the defined opening.

Figure 27:
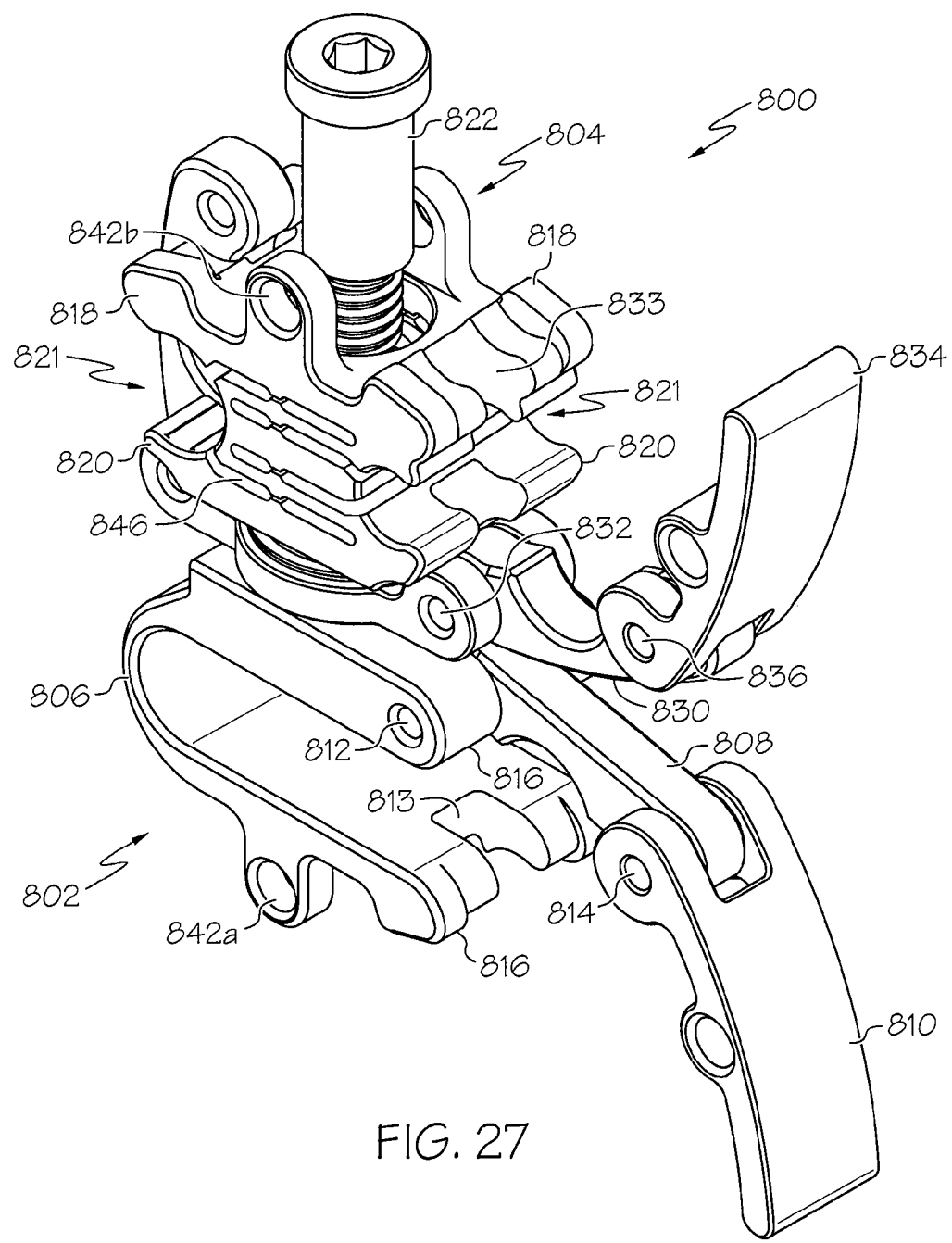
FIGS. 27 and 28 depict an illustrative ring frame to rod/pin external fixation clamping assembly in accordance with the teachings of the present disclosure.
Figure 28:
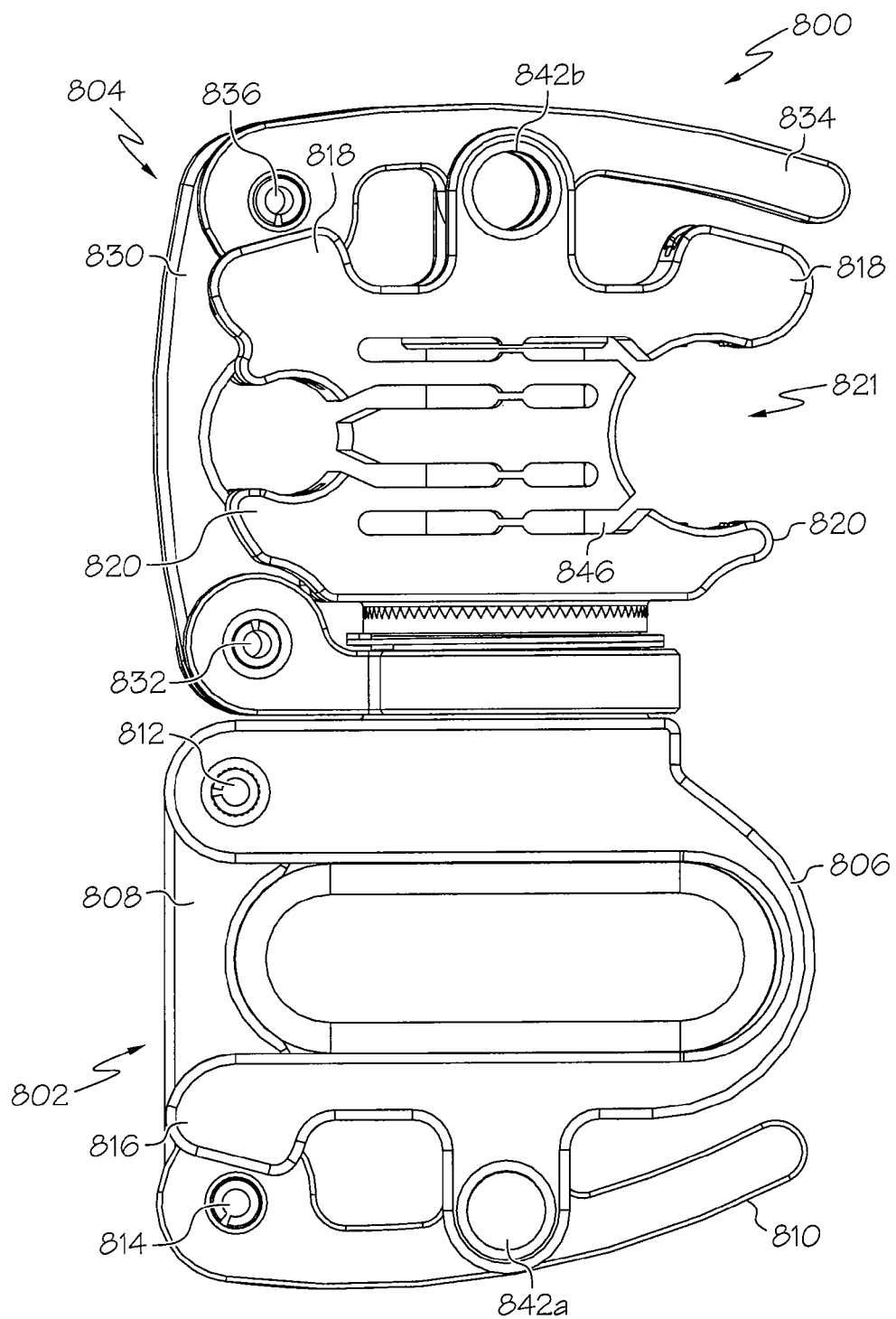

Referring to FIGS. 27 and 28, another illustrative clamping assembly 800 in accordance with the present disclosure is illustrated. In accordance with this aspect of the present disclosure, the illustrative clamping assembly 800 is a universal ring frame to rod/pin clamp assembly. According to this aspect of the present disclosure, the clamp assembly 800 is illustrated to include a first or lower clamp member 802 and a second or upper clamp member 804. The first clamp member 802 includes a clamp body 806, a locking arm 808, a cam arm 810, a locking arm pivot pin 812 and a cam arm pivot pin 814. The first clamp member 802 is configured to be snapped onto a ring frame or a rod (e.g., ring frames 102, 104) by positioning the clamp body 806 substantially perpendicular to the ring leg or rod and applying pressure to force end jaws 816 open and over the ring or rod. Alternatively, the first clamp member 802 can be snapped onto the ring frame or rod by positioning the clamp body 806 at the end of a ring leg or rod and applying pressure to slide the body onto the ring or rod.

The second clamp member 804 includes a pair of upper jaw portions 818 and a pair of lower jaw portions 820 which cooperate to define openings 821 for receiving cylindrical rods and/or pins that are needed to assemble the external fixation system.

In accordance with this illustrative embodiment, the first and second clamp members 802, 804 are connected to one another by a threaded clamp bolt 822 that passes through a common aperture of the clamp members in such a manner that it compresses the first and second clamp members 802, 804 against one another, as well as the rings, rods and/or pins held therein.

Once the various rings, rods and/or pins are positioned within the first and second clamp members 802, 804, first and second locking assemblies compress and hold the rings, rods and/or pins therein. To achieve this, the clamp members may be provisionally and independently locked. To provisionally lock the first clamp member 802, the locking arm 808 is rotated (via the locking arm pivot pin 812) towards and into a cam arm pocket 813. Once the surgeon is satisfied with the position and fixation of the bone fragments, the frame or fixator can be definitively locked without the use of additional tools or equipment. To achieve the definitive lock, the cam arm 810 is rotated towards the clamp body 806 via the cam arm pivot pin 814 located at the center of the cam arm 810 until it touches the clamp body.

Similarly, to independently and provisionally lock the second clamp member 804, a locking arm 830 that is coupled to the second clamp member is rotated (via the locking arm pivot pin 832) towards and into a cam arm pocket 833. Once the surgeon is satisfied with the position and fixation of the bone fragments, the frame or fixator can be definitively locked without the use of additional tools or equipment. To achieve the definitive lock, the cam arm 834 is rotated towards the second clamp member 804 via a cam arm pivot pin 836 located at the center of the cam arm 834 until it touches the second clamp member.

Once the cam arms 810, 834 are positioned within their respective clamp members 802, 804 during a definitive locking process, in accordance with certain aspects of the present disclosure, the cam arms 810, 834 can be further locked into place by utilizing a locking pin (not shown) that is configured to be inserted through the cam arms 810, 834. According to this embodiment, the clamp members 802, 804 each have a pair of upwardly projecting tabs 842A, 842B with through-holes formed therein. When the cam arms 810, 834 are positioned within the clamp members 802, 804, the through-holes align with a through-hole formed into the cam arms 810, 834 such that a common through-hole is created. The locking pin can then be inserted through this common through-hole, thereby preventing the cam arms 810, 834 from being individually lifted away from the clamp members 802, 804 until the locking pin is first removed.

While clamping assembly 800 can be configured such that the first and second clamp members 802, 804 are able to independently rotate with respect to one another, in accordance with certain aspects of the present disclosure, it may be desirable to arrest angular or rotational movement between such components. To provide means for arresting such movement of the first clamp member 802 relative to the second clamp member 804 about an a longitudinal axis of the clamp bolt 822, the first and second clamp members 802 and 804 may be formed to include cooperating serrated portions or surfaces that are configured to interact with each other such that relative movement between the first and second clamp members is prevented.

In accordance with certain aspects of the present teachings, the second clamp member 804 may have a series of axial slots 846 formed into its body. According to certain aspects of this embodiment, the axial slots may be positioned adjacent to and/or at least partially terminating into the openings 821 to thereby allow the jaw portions of the clamp member to be elastically displaced in response to a cylindrical rod, pin or the like being introduced therein. In other words, as a rod, pin, etc. is laterally introduced into one of the openings 821, the upper and lower jaw portions of that clamping member are urged apart from one another. Once the cylindrical object is fully seated within the upper and lower jaw portions of the clamping member, a counter-force snappingly retains the object temporarily in place, particularly as the upper and lower jaw portions return to their original position prior to being displaced. As those of skill in the art will understand and appreciate herein, by fabricating such axial slots 846 into the clamping assembly, the elastic deformation properties associated with such a design inherently allows the upper and lower jaw portions to function much like a leaf spring, and as a result, cylindrical items placed therein can be snappingly retained within the defined opening.

Figure 29:
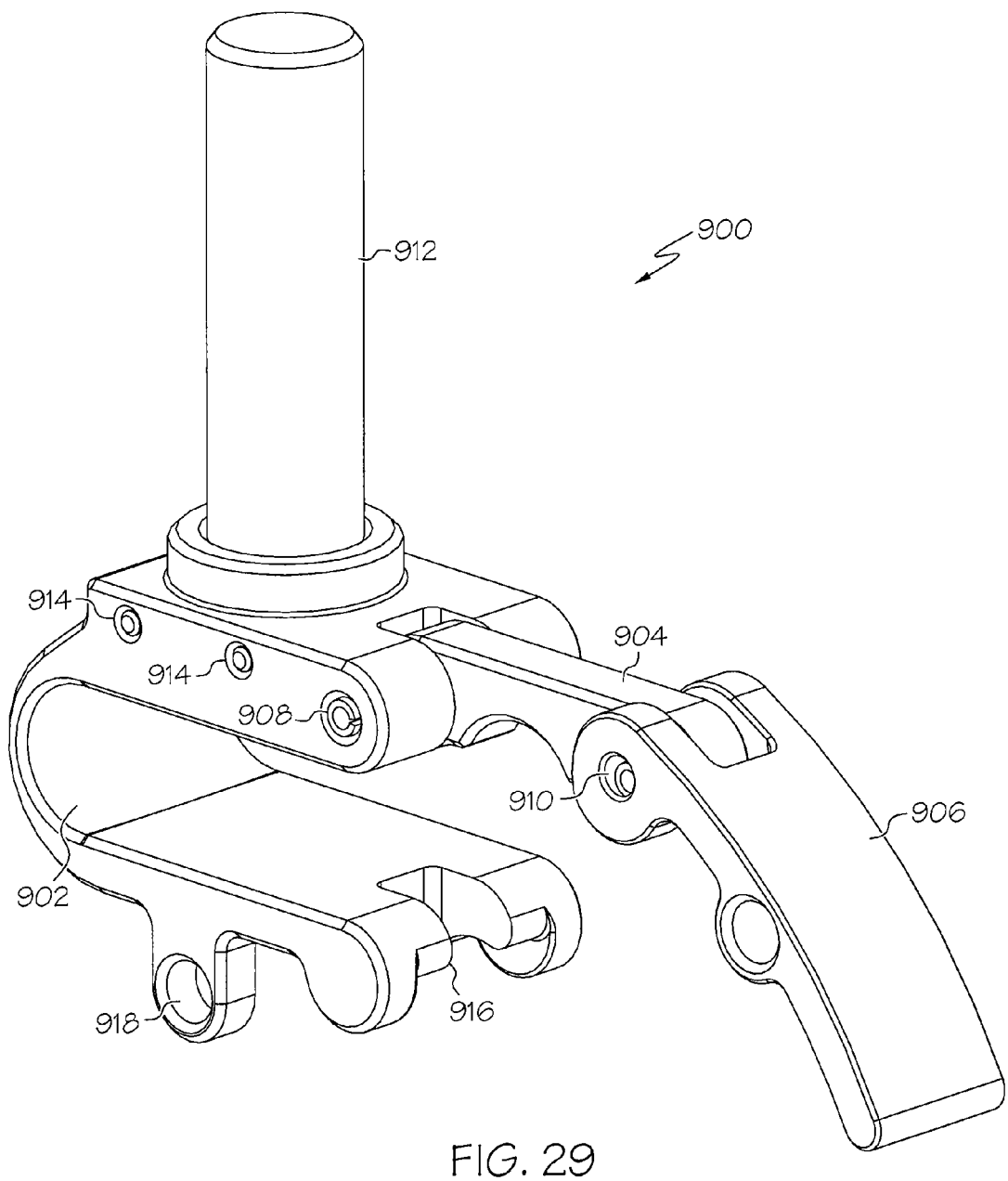
FIG. 29 is another illustrative ring-to-post clamping assembly in accordance with the teachings of the present disclosure.

FIG. 29 depicts an illustrative universal ring-to-post clamping assembly 900 in accordance with one embodiment of the present teachings. In accordance with this aspect of the present disclosure, the clamping assembly 900 includes a clamp body 902, a locking arm 904, a cam arm 906, a locking arm pivot pin 908, a cam arm pivot pin 910, a universal post 912 (which is configured to interface with a universal rod/pin clamp assembly) and a retaining pin 914 that retains the universal post into the clamp body 902.

Once the clamp body 902 is positioned on a ring frame, the locking arm 904 compresses and centers the ring frame inside the clamp body 902. To achieve this, the clamp may be provisionally locked by rotating the locking arm 904 (via the locking arm pivot pin 908) towards and into a cam arm pocket 916. Once the surgeon is satisfied with the position and fixation of the bone fragments, the frame or fixator is definitively locked without the use of additional tools or equipment. To achieve the definitive lock, the cam arm 906 is rotated towards the clamp body 902 via the cam arm pivot pin 910 located at the center of the cam arm 906 until it touches the clamp body 902.

Once the cam arm 906 is positioned against the clamp body 902 during a definitive locking process, in accordance with certain aspects of the present disclosure, the cam arm 906 can be further locked into place by utilizing a locking pin (not shown) that is configured to be inserted through the cam arm 906. According to this embodiment, the clamp body 902 has a pair of upwardly projecting tabs 918, each having a through-hole formed therein. When the cam arm 906 is positioned against the clamp body 902, the through-holes align with a through-hole formed into the cam arm 906 such that a common through-hole is created. The locking pin can then be inserted through this common through-hole, thereby preventing the cam arm 906 from being lifted away from the clamp body 902 until the locking pin is first removed.

While an exemplary embodiment incorporating the principles of the present application has been disclosed hereinabove, the present application is not limited to the disclosed embodiments. Instead, this application is intended to cover any variations, uses, or adaptations of the application using its general principles. Further, this application is intended to cover such departures from the present disclosure as come within known or customary practice in the art to which this present application pertains and which fall within the limits of the appended claims.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations).

The invention claimed is:

1. A polyaxial pivot housing for an external fixation system comprising:
   a first plate;
   a second plate substantially parallel to the first plate;
   a spherical member positioned between the first and second plates, the spherical member having a threaded post that is configured to attach to a support member of an external fixation frame; and
   a pivotably rotatable locking arm, the locking arm being configured to rotate about a longitudinal axis of the spherical member upon being pulled directionally toward the spherical member in order to orientationally lock the threaded post with respect to the external fixation frame by compressing the first and second plates against the spherical member.

2. The polyaxial pivot housing of claim 1, wherein the first plate includes a threaded bore hole configured to attach to an external fixation clamping assembly.

3. The polyaxial pivot housing of claim 1, wherein the first and second plates are connected by a locking bolt.

4. The polyaxial pivot housing of claim 1, further including a locking pin that is configured to prevent movement of the locking arm.

5. The polyaxial pivot housing of claim 1, wherein the first plate includes a first substantially circular recessed cavity that is dimensioned to receive a top portion of the spherical member.

6. The polyaxial pivot housing of claim 5, wherein the second plate includes a second substantially circular recessed cavity that is dimensioned to accept a bottom portion of the spherical member.

7. The polyaxial pivot housing of claim 1, wherein the housing includes a provisional locking feature that allows the alignment of bone fragments held by the external fixation frame to be slightly adjusted by overcoming a friction fit that is caused by compressive forces and soft tissue tension, the provisional locking feature being actuatable without the use of a tool.

8. The polyaxial pivot housing of claim 1, wherein the housing includes a definitive locking feature that allows bone fragments held by the external fixation frame to be secured in a defined alignment orientation, the definitive locking feature being manually actuatable without the use of a tool.

9. The polyaxial pivot housing of claim 8, wherein the definitive locking feature is actuated by moving the pivotably rotatable locking arm towards the spherical member about the longitudinal axis, the movement causing the second plate to compress the spherical member against the first plate.

10. The polyaxial pivot housing of claim 9, further comprising a set screw associated with the pivotably rotatable locking arm, the set screw being configured to prevent a locking bolt that passes through the first and second plates from moving independently of the pivotably rotatable locking am as the locking arm is moved about the longitudinal axis.

11. A polyaxial pivot housing for an external fixation system, comprising:
    a first plate;
    a second plate substantially parallel to the first plate;
    a locking screw connecting the first and second plates;
    a spherical member positioned between the first and second plates, the spherical member having a threaded post that is configured to attach to a support member of an external fixation frame; and
    a pivotably rotatable locking arm, the locking arm being configured to rotate about a longitudinal axis of the spherical member upon being pulled directionally toward the spherical member in order to orientationally lock the threaded post with respect to the external fixation frame by compressing the first and second plates against the spherical member;
    wherein the polyaxial pivot housing has a provisional locking feature and a definitive locking feature, each locking feature being manually actuatable without the use of a tool.

12. The polyaxial pivot housing of claim 11, wherein the first plate includes a threaded bore hole configured to attach to an external fixation clamping assembly.

13. The polyaxial pivot housing of claim 11, further including a locking pin that is configured to prevent movement of the locking arm.

14. The polyaxial pivot housing of claim 11, wherein the first plate includes a first substantially circular recessed cavity that is dimensioned to receive a top portion of the spherical member.

15. The polyaxial pivot housing of claim 14, wherein the second plate includes a second substantially circular recessed cavity that is dimensioned to accept a bottom portion of the spherical member.

16. The polyaxial pivot housing of claim 11, wherein the provisional locking feature is configured to allow the alignment of bone fragments held by the external fixation frame to be slightly adjusted by overcoming a friction fit that is caused by compressive forces and soft tissue tension.

17. The polyaxial pivot housing of claim 11, wherein the definitive locking feature is configured to allow bone fragments held by the external fixation frame to be secured in a defined alignment orientation.

18. The polyaxial pivot housing of claim 17, wherein the definitive locking feature is actuated by moving the pivotably rotatable locking arm towards the spherical member about the longitudinal axis, the movement causing the second plate to compress the spherical member against the first plate.

19. The polyaxial pivot housing of claim 18, further comprising a set screw associated with the pivotably rotatable locking arm, the set screw being configured to prevent a locking bolt that passes through the first and second plates from moving independently of the pivotably rotatable locking am as the locking arm is moved about the longitudinal axis.

* * * * *

UNITED STATES PATENT AND TRADEMARK OFFICE
CERTIFICATE OF CORRECTION

PATENT NO. : 9,463,045 B2
APPLICATION NO. : 14/212596
DATED : October 11, 2016
INVENTOR(S) : Cresina et al.

Page 1 of 1

It is certified that error appears in the above-identified patent and that said Letters Patent is hereby corrected as shown below:

In the Claims

In Column 24, Line 36, in Claim 10, delete "am" and insert --cam--, therefor

In Column 25, Line 25, in Claim 19, delete "am" and insert --cam--, therefor

Signed and Sealed this
Fifth Day of June, 2018

Andrei Iancu
*Director of the United States Patent and Trademark Office*